US011841369B2

(12) United States Patent
Kang et al.

(10) Patent No.: US 11,841,369 B2
(45) Date of Patent: *Dec. 12, 2023

(54) METHOD FOR IMPROVING QUALITY OF THERAPEUTIC CELL THROUGH REAL-TIME GLUTATHIONE MEASUREMENT

(71) Applicant: CELL2IN, INC., Seoul (KR)

(72) Inventors: Heun Soo Kang, Seoul (KR); Hye Mi Kim, Seoul (KR); Ji Eun Song, Seoul (KR); Gwang Mo Yang, Seoul (KR); Ji Woong Shin, Seoul (KR); Hye Won Kang, Seoul (KR); Yong Hwan Kim, Gyeonggi-do (KR); Myung Jin Kim, Seoul (KR)

(73) Assignee: Cell2In, Inc., Seoul (KR)

( * ) Notice: Subject to any disclaimer, the term of this patent is extended or adjusted under 35 U.S.C. 154(b) by 624 days.

This patent is subject to a terminal disclaimer.

(21) Appl. No.: 16/767,985

(22) PCT Filed: Nov. 28, 2018

(86) PCT No.: PCT/KR2018/014815
§ 371 (c)(1),
(2) Date: May 28, 2020

(87) PCT Pub. No.: WO2019/107913
PCT Pub. Date: Jun. 6, 2019

(65) Prior Publication Data
US 2021/0003582 A1 Jan. 7, 2021

(30) Foreign Application Priority Data

Nov. 28, 2017 (KR) .................. 10-2017-0160563
Aug. 14, 2018 (KR) .................. 10-2018-0094878

(51) Int. Cl.
*G01N 33/68* (2006.01)
*G01N 21/64* (2006.01)
*G01N 33/50* (2006.01)
*A61K 38/06* (2006.01)

(52) U.S. Cl.
CPC ........... *G01N 33/68* (2013.01); *A61K 38/063* (2013.01); *G01N 21/6428* (2013.01); *G01N 33/5005* (2013.01); *G01N 33/5044* (2013.01); *G01N 33/5076* (2013.01); *G01N 33/6815* (2013.01); *G01N 33/6893* (2013.01); *G01N 2021/6439* (2013.01); *G01N 2800/7009* (2013.01)

(58) Field of Classification Search
CPC ..... G01N 2333/91177; G01N 33/5005; C12N 2500/00; C12N 5/00
See application file for complete search history.

(56) References Cited

U.S. PATENT DOCUMENTS 11,499,978 B2 * 11/2022 Kang ................ G01N 33/5005
2017/0307624 A1 10/2017 Kim

FOREIGN PATENT DOCUMENTS

| JP | 5466842 B2 | 4/2014 |
| KR | 20160059978 A | 5/2016 |
| WO | WO 2017-016631 | 2/2017 |
| WO | 2017/032811 A1 | 3/2017 |

OTHER PUBLICATIONS

Dumaswala et al., "Glutathione loading prevents free radical injury in red blood cells after storage," Free Radic. Res. Nov. 2000;33(5):517-29. PMID: 11200085. (Year: 2000).*
Anderson, "Glutathione: an overview of biosynthesis and modulation," Chem. Biol. Interact. Apr. 24, 1998;111-112:1-14. PMID: 9679538. (Year: 1998).*
W. Zeng et al., "Antioxidant treatment enhances human mesenchymal stem cell anti-stress ability and therapeutic efficacy in an acute liver failure model," Scientific Reports, 5:11100, 17 pages (2015).
Yahata et al., "Accumulation of oxidative DNA damage restricts the self-renewal capacity of human hematopoietic stem cells," Blood, 118(11), 2941-50 (2011).
Kim et al., "Converging Translational Research Center for the Development of Pulmonary Fibrosis Therapeutics", Final Report, Seoul National University R&Db Foundation, Apr. 2014, pp. 1-41.
Cho et al., "A Coumarin-based Fluorescence Sensor for the Reversible Detection of Thiols", Chemistry Letters, 2012, vol. 41, pp. 1611-1612.
Jeong et al., "Real-time monitoring of Glutathione in Living Cells Reveals that High Glutathione Levels are Required to maintain Stem Cell Function", Stem Cell reports, (electronic publication) Jan. 4, 2018, vol. 10, pp. 600-614, Supplemental Information (pp. 1-16).
Cayman Chemical, Glutathione Cell-Based Detection Kit (Blue Fluorescence), Item No. 600360, copyrighted Oct. 24, 2016, pp. 3-19.
International Search Report dated Mar. 11, 2019 for International Application No. PCT/KR2018/014815, 4 pages.
Don-Sup Lee et al., "Airway epithelial cells initiate the allergen response through transglutaminase 2 by inducing IL-33 expression and a subsequent Th2 response", Respiratory Research, 2013, 14:35; https://respiratory-research.com/content/14/1/35.
Keunhee Oh et al., "Epithelial transglutaminase 2 is needed for T cell interleukin-17 production and subsequent pulmonary inflammation and fibrosis in bleomycin-treated mice", Exp. Med. vol. 208, No. 8, 1707-1719; www.em.org.cgl/doi/10.1084/jem20202457.
Dong-Sup Lee et al., "Transglutaminase 2 exacerbates experimental autoimmune encephalomyelitis throughh positive regulation of encephalitogenic T cell differentiation and inflammation", Clinical Immunology (2012) 145, 122-132.

(Continued)

*Primary Examiner* — Theodore R. Howell
(74) *Attorney, Agent, or Firm* — McDonnell Boehnen Hulbert & Berghoff LLP

(57) ABSTRACT

The present invention relates to a method of improving the quality of therapeutic cells by real-time glutathione monitoring.

9 Claims, 56 Drawing Sheets
Specification includes a Sequence Listing.

(56) References Cited

OTHER PUBLICATIONS

Dong-Sup Lee et al., "OP-690550 Treatment Ameliorates Established Disease and provides long-Term Therapeutic Effects in an SKG Arthritis Model", Immune Network, vol. 13, No. 6257-263, Dec. 2013.

In-Gyu Kim et al., "Endoplasmic reticulum stress activates transglutaminase 3 leading to protein aggregation", International Journal of Molecular Medicine, Oct. 28, 2013, 2 pages.

In-Gyu Kim et al., "Intimal Hyperplasia in Loop-Injured Carotid Arteries is Attenuuated in Transglutaminase 2-Null Mice", The Korean Academy of Medical Science, Aug. 8, 2013, 2 pages.

Hyun Ho Park et al., "Structural and Functional Studies of Casein Kinase I-Like Portein from Rice", Plant Cell Physiol 53(2): 304-311 (2012).

Hyun Ho Park et al., "Crystallization and preliminary X-ray crystallographic studies of cPOP1", Acta Cryst. (2013) F69, 292 294.

Hyun Ho Park et al., "General interaction mode of CIDE:CIDE complex revealed by a mutation studay of the Drep2 CIDE domain", FEBS Letters 587 (2013) 854 859.

Hyun Ho Park et al., "A putative role of Drep1 in apoptotic DNA fragmentation system in fly is mediated by direct interaction with Drep2 and Drep4", published onlin Feb. 16, 2013, 2 pages.

Hyun Ho Park et al., "Crystallization and preliminary X-ray crystallographic studies of transglutaminase 2 in complex with Ca2", Acta Cryst (2014) F70, 513 516, 2 pages.

Tae-ho Jang et al., "Crystallization and preliminary X-ray crystallographic studies of the N-terminal domain of human ribosomal protein L7a (RPL7a)", Acta Cryst (2011) F67, 510-512.

Tae-ho Jang et al., "Inhibition of genotoxic stress induced apoptosis by novel TAT-fused peptides targeting PIDDosome", Biochemical Pharmacology 83 (2012) 218-227.

\* cited by examiner

METHOD FOR IMPROVING QUALITY OF THERAPEUTIC CELL THROUGH REAL-TIME GLUTATHIONE MEASUREMENT

CROSS-REFERENCE TO RELATED APPLICATIONS

This application is a U.S. National Stage application of International Patent Application PCT/KR2018/014815, filed Nov. 28, 2018, which claims the benefit of priority of Korean Patent Application no. 10-2017-0160563, filed Nov. 28, 2017, and of Korean Patent Application no. 10-2018-0094878, filed Aug. 14, 2018.

REFERENCE TO AN ELECTRONIC SEQUENCE LISTING

This application contains a Sequence Listing which has been submitted electronically and is hereby incorporated by reference in its entirety. The Sequence Listing was created on Jun. 8, 2023, is named "20-890-WO-US_SequenceListing_ST25.txt" and is 1,906 bytes in size.

TECHNICAL FIELD

The present invention relates to a method of improving the quality of therapeutic cells through real-time glutathione monitoring.

BACKGROUND ART

Although the human body properly eliminates reactive oxygen species (ROS) through the action of the antioxidant system to maintain homeostasis, when the balance between ROS production and the antioxidant action is broken, oxidative stress increases, and the oxidative stress have recently attracted attention as an important common causative factor for the onset of a metabolic syndrome such as diabetes, obesity or a cardiovascular disease as well as aging, an age-related degenerative disease such as degenerative arthritis, cataracts or Alzheimer's disease, various types of cancer and fibrotic diseases. As one of the main mechanisms of aging, ROS are instable and highly reactive to oxidize biomolecules and thus cause biochemical and physiological damage. Therefore, an antioxidation degree or antioxidation capacity, in addition to the oxidation degree of the human body, may be a critical biomarker for calculating biological age.

ROS are important signaling molecules that regulate cellular metabolism, proliferation, and survival. An increase of ROS induces the thiol oxidation of cysteine residues on signaling proteins, resulting in changes in protein activity to regulate cellular functions. Particularly, ROS-mediated oxidation plays an important role in regulating various signaling proteins of stem cells (SCs) that affect self-renewal capacity, pluripotency, viability and genomic stability, including OCT4, NRF2, FoxOs, APE1/Ref-1, ATM, HIF-1, p38, and p53 (Wang et al., 2013).

Meanwhile, there are various methods used to evaluate the quality, consistency and efficacy of stem cells and cell cultures. Stem cells are defined by self-renewal capacity and the expression of a specific marker. The identity of a desired cell population should be defined. A current hESC cell line is characterized by the absence of measurable microbiological infection using a series of standardized metrics, i.e., in vitro (the formation of an embryonic body) and in vivo differentiation (the formation of teratoma-like xenografts) potentials, as well as surface antigens, the expression of a specific enzyme activity (e.g., alkaline phosphatase), gene expression, epigenetic markers, evaluation of genomic stability, cytology and morphology (Japanese Patent No. 5185443). However, although the procedures used to evaluate the characteristics of these stem cells require skilled personnel, they provide relatively little information, and are time consuming and costly. In addition, these procedures do not provide critical information about the safety profile and/or objective suitability of the produced cells. In the case of stem cells, in addition to the expansion of a cell population under conditions of supporting proliferation of undifferentiated cells, it is necessary to provide information on the quality and consistency of a stem cell line in an induction stage and to improve cell quality under continuous subculture in cell culture.

DISCLOSURE

Technical Problem

The present invention is directed to providing a method of improving the quality of therapeutic cells through real-time glutathione monitoring. In addition, the present invention is directed to characterizing cells and/or improving the quality and safety profile of an in vitro cell culture system.

Technical Solution

Hereinafter, various exemplary embodiments described in the present invention are described with reference to drawings. In the following description, for complete understanding of the present invention, various specific details, such as specific forms, compositions and processes are described. However, specific embodiments may be accomplished without one or more of these specific details, or with other known methods and forms. In another example, known processes and manufacturing techniques are not described in any detail so as not to unnecessarily obscure the present invention. The reference throughout the specification to "one embodiment" or "embodiments" means that special features, forms, compositions or characteristics described in connection with the embodiment(s) are included in one or more embodiments of the present invention. Therefore, the context of the "one embodiment" or "embodiments" expressed at various locations throughout the specification does not necessarily represent the same embodiment of the present invention. In addition, special features, forms, compositions or characteristics may be combined in any suitable manner in one or more embodiments. Unless defined otherwise, in the specification, all scientific and technical terms used herein have the same meaning as commonly understood by one of ordinary skill in the art to which the present invention belongs.

In one exemplary embodiment of the present invention, the term "Fluorescent Real-time SH group (FreSH)-Tracer" or "FreSH" refers to a compound including a compound represented by Formula A below or a salt thereof, and is used as a fluorescent material for detecting a thiol without limitation to a cell organelle. Therefore, FreSH-Tracer includes both a compound specific to a cell organelle and a compound not limited thereto.

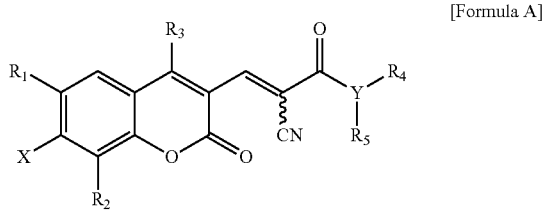

[Formula A]

In Formula A above, $R_1$ and $R_2$ are each independently hydrogen, $C_{1-4}$ linear or branched alkyl, or heterocycloalkyl or heterocycloalkenyl with a 5- or 6-membered ring, which is formed of $R_1$, $R_2$ and X; $R_3$ is hydrogen or $C_{1-4}$ linear or branched alkyl; $R_4$ and $R_5$ are each independently hydrogen, $C_{1-5}$ linear or branched alkyl, or —$(CH_2)_m$—COO—$C_{1-5}$ linear or branched alkyl (m is an integer of 1 to 5), or $R_4$, $R_5$ and Y form $C_{3-7}$ heterocycloalkyl, and the heterocycloalkyl is unsubstituted or $R_6$-substituted heterocycloalkyl; $R_6$ is —COO($CH_2)_n$—OCO—$C_{1-5}$ linear or branched alkyl (n is an integer of 1 to 5), —(CONH)—$(CH_2)_o$—$PPh_3{}^+Cl^-$ (o is an integer of 1 to 5) or —(CONH)—$CHR_7$—COO $(CH_2)_p$—OCO—$C_{1-5}$ linear or branched alkyl (p is an integer of 1 to 5); $R_7$ is —$(CH_2)_q$—COO$(CH_2)_r$—OCO—$C_{1-5}$ linear or branched alkyl (each of q and r is an integer of 1 to 5); and X and Y are each independently N or O.

In one exemplary embodiment of the present invention, the term "Mitochondria Fluorescent Real-time SH group-Tracer (MitoFreSH-Tracer)" or "Golgi Fluorescent Real-time SH group-Tracer (GolgiFreSH-Tracer)" refers to a compound including a compound represented by Formula B below or a salt thereof, and is used to measure an amount of thiols in the mitochondria or Golgi complex, but the present invention is not limited thereto. In addition, as an example, particularly, a compound represented by Formula B-8 is used as GolgiFreSH-Tracer, and a compound represented by Formula B-4 is used as MitoFreSH-Tracer. By using these compounds, it can be demonstrated that a fluorescence intensity is continuous, ratiometric, and reversibly increased/decreased according to an amount of thiols in the mitochondria or Golgi complex.

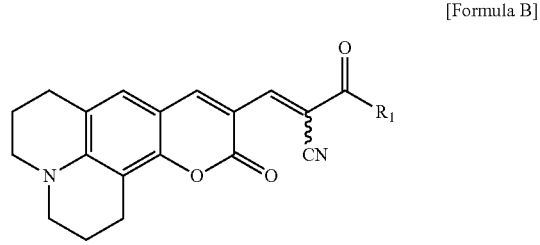

[Formula B]

In Formula B above, $R_1$ is heterocycloalkyl, which is a 3- to 7-membered ring including one or more N atoms.

The term "ratiometric" used herein means that an output is directly proportional to an input. Specifically, in one exemplary embodiment of the present invention, the "ratiometric" means that a fluorescence intensity or a ratio of the fluorescence intensity of the composition of the present invention increases or decreases directly proportionally to a thiol input.

The term "detection" used herein refers to the detection of presence of chemical species or biological materials in samples or the measurement of an amount thereof.

The term "reversible" used herein refers to a state in which a mixture of a reactant and a product can make a mixture in equilibrium in a chemical reaction.

The term "thiol" used herein refers to an organic compound including a carbon-bound sulfhydryl group, and is used interchangeably with "sulfhydryl".

In an exemplary embodiment of the present invention, the mitochondria of the present invention are included in living cells. In terms of measurement of thiol levels in the mitochondria, the composition of the present invention is not limited to measurement of thiol levels in the mitochondria isolated from the cells, and thiol levels in the mitochondria being included in the cells can be measured. Particularly, thiol levels in the mitochondria in living cells may be specifically detected.

In the specification, GolgiFreSH-Tracer refers to a coumarin derivative having a cyanoacrylamide electrophile, which is the compound represented by Formula B of the present invention, and it is used as a fluorescent material for detecting a thiol in the Golgi complex according to the present invention. The inventors developed GolgiFreSH-Tracer, which is a biosensor capable of quantitatively or qualitatively detecting a thiol amount in the Golgi complex in cells in real time. As a result, it was demonstrated that the fluorescence intensity of GolgiFreSH-Tracer of the present invention represented by Formula B-5 of the present invention is continuously, ratiometrically and reversibly increased or decreased according to a thiol amount in the Golgi complex in cells, and it was proved that GolgiFreSH-Tracer of the present invention can be effectively used as a biosensor with significant sensitivity in quantitatively or qualitatively detecting a thiol amount in the Golgi complex in cells in real time.

In one exemplary embodiment of the present invention, regarding the "safety" and "quality" of cells or stem cells, there is a difference in phenotype between an unsafe (e.g., tumorigenic) cell or cells and/or cells of poor quality (perhaps a lack of expression of a specific marker). The difference in phenotype may not be detected by a standard method. The present invention provides a highly sensitive and elaborate means for determining whether a cell or a cell system (e.g., a cell population of cell culture) conforms with a series of predetermined standards and improving cell characteristics to conform with the standards. Previously, to investigate a cell quality characteristic, one skilled in the art was able to establish microRNA profiles of cells known to conform with a series of predetermined safety and/or quality standards, and evaluate whether they correspond to the predetermined quality and/or characteristic by comparing microRNA against other cells of the same type.

In one exemplary embodiment of the present invention, "buthionine-sulfoximine (BSO)" irreversibly inhibits γ-glutamylcysteine synthase, which is an essential enzyme for synthesizing glutathione (GSH), to induce oxidative stress in cells. It is known that oxidative stress induced by GSH depletion can induce genome rearrangement such as DNA deletion, and when oxidation-promoting conditions are blocked by N-acetyl-L-cysteine (NAC), which is an exogenous antioxidant, DNA deletion can be inhibited.

The term "stem cells" used herein refers to undifferentiated cells having a self-replication capacity and a differentiation/proliferation capacity. The stem cells include subpopulations of pluripotent stem cells, multipotent stem cells, and unipotent stem cells according to differentiation capacity. The pluripotent stem cells refer to cells having a capacity of differentiating into all tissues or cells constituting a living body. In addition, multipotent stem cells refer to cells having a capacity of differentiating into multiple types, not all types, of tissues or cells. The unipotent stem cells refer to cells having a capacity of differentiating into specific tissues or cells. The pluripotent stem cells may include embryonic stem cells (ES cells), undifferentiated embryonic germ cells (EG cells), and induced pluripotent stem cells (iPS cells). The multipotent stem cells may include adult stem cells such as mesenchymal stem cells (derived from adipose, bone marrow, cord blood or umbilical cord), hematopoietic stem cells (derived from bone marrow or peripheral blood), nervous system stem cells and reproductive stem cells. In addition, the unipotent stem cells may include committed stem cells which are usually present with a low division capacity, but once activated, they are vigorously divided, producing only hepatocytes. Particularly, in the present invention, it is preferable that the mesenchymal stem cells (MSCs) be human embryonic stem cell-derived mesenchymal stroma cells (hES-MSCs), bone marrow mesenchymal stem cells (BM-MSCs), umbilical cord mesenchymal stem cells (UC-MSCs), and adipose-derived stem cells (ADSCs), but the present invention is not limited thereto.

The term "embryonic stem cells (ESCs)" used herein refers to cells obtained by isolating the inner cell mass of a blastocyst immediately before the implantation of fertilized eggs and culturing the inner cell mass in vitro, and the ESCs have pluripotency such that they can differentiate into cells of all tissues of an individual. In a broad sense, the ESCs include an embryonic body derived from embryonic stem cells. The term "embryonic body or embryoid body (EB)" used herein refers to the spherical mass of stem cells produced in suspension culture, and since the EB has the potential to differentiate into endoderm, mesoderm and ectoderm, it is used as a precursor in most differentiation-inducing processes for securing tissue-specific differentiated cells.

The term "extract" used herein refers to an agent prepared by squeezing herbal medicine into a suitable leaching solution, and concentrating the leaching solution through evaporation, but the present invention is not limited thereto, and may refer to a liquid extract obtained by extraction, a diluent or concentrate of the liquid extract, a dry product obtained by drying the liquid extract, or a partially-purified or purified component. As an extraction method, preferably, boiling extraction, hot water extraction, cold-immersion extraction, reflux cooling extraction, or ultrasonic extraction may be used, but the present invention is not limited thereto.

In the present invention, the extract may be prepared through extraction with an extraction solvent or through fractionation by applying a fractionation solvent to an extract prepared by extraction with an extraction solvent. The extraction solvent may be, but is not limited to, water, an organic solvent, or a mixed solvent thereof, and the organic solvent may be a polar solvent such as an alcohol having 1 to 4 carbon atoms, ethyl acetate or acetone, a non-polar solvent such as hexane or dichloromethane, or a mixed solvent thereof.

A GSH amount according to entire cells or cell organelles may be measured by a glutathione probe. The FreSH-Tracer of the present invention is a newly-synthesized fluorescent dye for rapidly and easily measuring an amount of glutathione (GSH) in living cells. FreSH-Tracer is a small molecular probe that can easily enter cells and cell organelles, and it binds to a thiol (—SH) group of GSH (see FIG. 1). When FreSH-Tracer binds to GSH, fluorescence is observed at a wavelength range including 510 nm (F510), and when FreSH-Tracer does not bind to GSH, fluorescence is observed at a wavelength range including 580 nm (F580). With the measured fluorescence value of F510/F580, a GSH amount in cells may be measured. A reaction between FreSH-Tracer and GSH is reversible, and does not consume GSH in cells in measurement.

The term "glutathione mean or median level (GM)" used herein is a parameter for measuring an antioxidation capacity of cells by measuring the mean or median of GSH in cultured cells, by the method of monitoring glutathione.

The term "glutathione heterogeneity (GH)" used herein is a parameter for measuring an antioxidation capacity of cells by measuring a distribution pattern of GSH in cultured cells using the method of monitoring glutathione. The heterogeneity is the coefficient of variation or the robust coefficient of variation, and a method of calculating the coefficient of variation is shown in FIG. 8.

The term "glutathione regeneration capacity (GRC)" used herein is a parameter which can objectively analyze the antioxidation capacity of cells, which is measured by treating diamide to induce a condition for reducing GSH to GSSG and evaluating a cell capacity of recovering GSH through real-time monitoring of a GSH concentration of cells. That is, GRC is a value obtained by real-time monitoring of a FR or F510 after living cells are treated with an oxidizing agent, calculated by dividing a value obtained by subtracting a second area under the curve (AUC) of a second oxidizing agent-treated group from a first AUC of a first oxidizing agent-treated group by a value obtained by subtracting the second AUC of the second oxidizing agent-treated group from a third AUC of a naive control and multiplying the resulting value by 100.

The term "reversible oxidizing agent" or "first oxidizing agent" used herein may include hydroperoxides such as $H_2O_2$, and tert-butyl peroxide; thiol oxidizing agents such as diamide, GSSG (oxidized GSH), 5,5'-dithiobis(2-nitrobenzoic acid), maleimide, N-ethyl maleimide, 4-maleimidobutyric acid, 3-maleimidopropionic acid and iodoacetamide; glutathione reductase inhibitors such as bis-chloroethylnitrozourea; thioredoxin inhibitors such as PX-12; mitochondrial electron transport chain inhibitors such as antimycin A, rotenone, oligomycin and carbonyl cyanide m-chlorophenyl hydrazone; NADPH oxidase activators such as phorbol 12-myristate 13-acetate; gpx4 inhibitors such as 1S,3R-RAS-selective lethal 3 (1S,3R-RSL3), DPI19, DPI18, DPI17, DPI13, DPI12, DPI10 (ML210), DPI7 (ML162), and altretamine; system $x^-_c$ inhibitors such as erastin, sulfasalazine, sorafenib, glutamate, piperazine erastin, imidazole ketone erastin, and an erastin analog; inducers for reducing GPX4 protein and CoQ10 levels, such as ferroptosis inducer 56 (FIN56); lipid peroxidation inducers such as caspase-independent lethal 56 (CIL56) and endoperoxide ($FINO_2$), which is a ferroptosis inducer; glutamate-cysteine ligase (GCL) inhibitors such as buthionine-(S,R)-sulfoximine; GSH reduction inducers such as diethyl maleate; DPI2, cisplatin, cysteinase, statin, iron ammonium citrate, trigonelline, carbon tetrachloride, silica-based nanoparticles and specific heat plasma. The oxidative stress level may be 0.05 to 20 μM.

The term "irreversible thiol oxidizing agent," "irreversible oxidizing agent" or "second oxidizing agent" used herein refers to an agent that can be used to ensure that any unreacted group (e.g., thiol) in a cytotoxic agent is deactivated. This agent may help prevent the dimerization of a cytotoxic agent, particularly, a cytotoxic agent with an unreacted thiol group (e.g., DM1). That is, the irreversible thiol oxidizing agent is a material for forming a blank group that completely eliminates GSH. For example, the material may be maleimide, 4-maleimidobutyric acid, 3-maleimidopropionic acid, ethylmaleimide, N-ethylmaleimide, iodoacetamide, 5,5'-dithiobis(2-nitrobenzoic acid), or iodoacetamidopropionic acid, but the present invention is not limited thereto, and the material is preferably ethylmaleimide.

In one exemplary embodiment, the quality of stem cells may be determined with a range of GM, GH and GRC reference values, and may be determined by comparing GM, GH and GRC values of target cells and values of standard stem cells of the target cells.

The term "oxidizing agent" used herein generally includes treatment causing oxidative stress in cells, in addition to a material which causes oxidation. Preferably, the oxidizing agent includes a first oxidizing agent or a second oxidizing agent.

The term "oxidative stress resistance capacity (ORC)" is a value of cell counts with the variation in GHS expression, obtained by comparing the GSH levels quantified after living cells are treated with a first oxidizing agent with the GSH levels quantified in control cells which are not treated with an oxidizing agent or in control cells which have not been treated with an oxidizing agent yet. For example, ORC can be monitored to see whether a mitochondria glutathione (mGSH) expression level can be maintained at a normal level after oxidative stress is applied to cells. In addition, in one exemplary embodiment, the quality of stem cells may be determined as having an ORC value of 10% to 100%, preferably 30% to 90%, and more preferably 40% to 90%.

In the present invention, in ORC, the term "oxidative stress" used herein refers to application of a first oxidizing agent to cells.

The present invention provides a method of improving the quality of cells, which includes: isolating desired cells; measuring a glutathione level in the isolated cells; determining cell quality according to the glutathione level; and adding a material capable of improving a glutathione evaluation parameter into the isolated cells.

In one exemplary embodiment of the present invention, the determination of cell quality according to a glutathione level is performed based on any one or more evaluation parameters as follows: i) GM of cells; ii) GH of cells; iii) GRC of cells; and iv) ORC. Here, GM is calculated as the mean or median value of a cellular FreSH-tracer ratio (FR) or F510, GH is calculated as the coefficient of variation or the robust coefficient of variation of cellular FR or F510, GRC is obtained by real-time monitoring of FR or F510 after cells are treated with an oxidizing agent, as calculated by dividing a value obtained by subtracting a second area under the curve (AUC) of a second oxidizing agent-treated group from a first AUC of a first oxidizing agent-treated group by a value obtained by subtracting the second AUC of the second oxidizing agent-treated group from a third AUC of a naive control and multiplying the resulting value by 100, and ORC is a value of cell counts with the variation in GSH expression, obtained by comparing the GSH levels quantified after living cells are treated with a first oxidizing agent with the GSH levels quantified in control cells which are not treated with an oxidizing agent or in control cells which have not been treated with an oxidizing agent yet. In another exemplary embodiment of the present invention, the improvement of cell quality is achieved by raising GM and GRC, which are glutathione evaluation parameters, lowering GH, or reducing a ratio of cells with decreased GSH by treatment with an oxidizing agent, as compared with cells not treated with an oxidizing agent in ORC measurement. In still another exemplary embodiment of the present invention, a material capable of improving a glutathione evaluation parameter is any one or more selected from the group consisting of glutathione ethyl ester, ascorbic acid 2-glucoside, glutathione, N-acetylcysteine, 2-mercaptoethanol, dithiothreitol (DTT), cysteine, γ-glutamyl cysteine (GGC), GGC esters, oxo-4-thiazolidinecarboxylic acid (OTC), L-2-oxo-4-thiazolidinecarboxylic acid, lipoic acid, Ferrostatin-1, Liproxstatin-1, vitamin D3, 1-alpha, 25-dihydroxy VitD3, vitamin E, coenzyme Q10, an iron or copper ion chelator such as deferoxamine, deferiprone or deferasirox, baicalin, baicalein, luteolin, quercetin, butein, flower extracts of *Chrysanthemum morifolium* Ramat, leaf extracts of *Cedela sinensis* A. Juss, extracts of *Oenothera stricta* Ledeb., extracts of *Equisetum arvense* L., leaf extracts of *Ipomoea batatas*, tomato extracts and homocysteine. In yet another exemplary embodiment of the present invention, before the step of improving a glutathione evaluation parameter, a step of measuring a glutathione level is further included. In yet another exemplary embodiment of the present invention, after the step of adding a material capable of improving a glutathione evaluation parameter, a step of confirming an increase in a glutathione level by measuring the glutathione level is further included. In yet another exemplary embodiment of the present invention, desired cells may be any one type of stem cells selected from the group consisting of adult stem cells, embryonic stem cells and induced pluripotent stem cells; any one type of immune cells selected from the group consisting of dendritic cells, natural killer cells, T cells, B cells, regulatory T cells (Treg cells), natural killer T cells, innate lymphoid cells, macrophages, granulocytes, chimeric antigen receptor-T (CAR-T) cells, lymphokine-activated killer (LAK) cells and cytokine induced killer (CIK) cells; any one type of somatic cells selected from the group consisting of fibroblasts, chondrocytes, synovial cells, keratinocytes, adipocytes, osteoblasts, osteoclasts and peripheral blood mononuclear cells; any one type of cell line used in production of a protein agent, selected from the group consisting of CHO cells, NS0 cells, Sp2/0 cells, BHK cells, C127 cells, HEK293 cells, HT-1080 cells, and PER.C6 cells; or any one type of a human microbiome selected from the group consisting of microorganisms originating from the mouth, nasal cavity, lungs, skin, gastric intestinal tract and urinary tract of a human or animal. In yet another exemplary embodiment of the present invention, the T cells exclude regulatory T cells (Treg cells). In yet another exemplary embodiment of the present invention, the first oxidizing agent includes hydroperoxides such as $H_2O_2$ and tert-butyl peroxide; thiol oxidizing agents such as diamide, GSSG (oxidized GSH), 5,5'-dithiobis(2-nitrobenzoic acid), maleimide, N-ethyl maleimide, 4-maleimidobutyric acid, 3-maleimidopropionic acid and iodoacetamide; glutathione reductase inhibitors such as bis-chloroethylnitrozourea; thioredoxin inhibitors such as PX-12; mitochondrial electron transport chain inhibitors such as antimycin A, rotenone, oligomycin and carbonyl cyanide m-chlorophenyl hydrazone; NADPH oxidase activators such as phorbol 12-myristate 13-acetate; gpx4 inhibitors such as 1S,3R-RAS-selective lethal 3 (1S,3R-RSL3), DPI19, DPI18, DPI17, DPI13, DPI12, DPI10 (ML210), DPI7 (ML162), and altretamine; system $x^-_c$ inhibitors such as erastin, sulfasalazine, sorafenib, glutamate, piperazine erastin, imidazole ketone erastin, and an erastin analog; inducers for reducing GPX4 protein and CoQ10 levels, such as ferroptosis inducer 56 (FIN56); lipid peroxidation inducers such as caspase-independent lethal 56 (CIL56) and endoperoxide ($FINO_2$), which is a ferroptosis inducer; glutamate-cysteine ligase (GCL) inhibitors such as buthionine-(S,R)-sulfoximine; GSH reduction inducers such as diethyl maleate; DPI2, cisplatin, cysteinase, statin, iron ammonium citrate, trigonelline, carbon tetrachloride, silica-based nanoparticles and specific heat plasma. In yet another exemplary embodiment of the present invention, the second oxidizing agent includes maleimide, 4-maleimidobutyric acid, 3-maleimidopropionic acid, ethylmaleimide, N-ethylmaleimide, iodoacetamide, 5,5'-dithiobis(2-nitrobenzoic acid), or iodoacetamidopropionic acid.

The present invention provides a composition for improving cell quality, added after cell quality according to a glutathione level is determined in desired cells, wherein the determination of the cell quality according to a glutathione level is performed based on evaluation parameters as follows: i) GM of cells; ii) GH of cells; iii) GRC of cells; and iv) ORC. Here, GM is calculated as the mean or median value of cellular FR or F510, GH is calculated as the coefficient of variation or the robust coefficient of variation of cellular FR or F510, GRC is obtained by real-time monitoring of FR or F510 after living cells are treated with an oxidizing agent, as calculated by dividing a value obtained by subtracting a second area under the curve (AUC) of a second oxidizing agent-treated group from a first AUC of a first oxidizing agent-treated group by a value obtained by subtracting the second AUC of the second oxidizing agent-treated group from a third AUC of a naive control and multiplying the resulting value by 100, and ORC is a value of cell counts with the variation in GSH expression, obtained by comparing the GSH levels quantified after living cells are treated with a first oxidizing agent with the GSH levels quantified in control cells which are not treated with an oxidizing agent or in control cells which have not been treated with an oxidizing agent yet.

In one exemplary embodiment of the present invention, the improvement of cell quality is achieved by raising a GM and GRC, which are the glutathione evaluation parameters, lowering GH, or reducing a ratio of cells with decreased GSH by treatment with an oxidizing agent, as compared with cells not treated with an oxidizing agent in ORC measurement. In another exemplary embodiment of the present invention, a material capable of improving a glutathione evaluation parameter is any one or more selected from the group consisting of glutathione ethyl ester, ascorbic acid 2-glucoside, glutathione, N-acetylcysteine, 2-mercaptoethanol, dithiothreitol (DTT), cysteine, γ-glutamyl cysteine (GGC), GGC esters, oxo-4-thiazolidinecarboxylic acid (OTC), L-2-oxo-4-thiazolidinecarboxylic acid, lipoic acid, Ferrostatin-1, Liproxstatin-1, vitamin D3, 1-alpha, 25-dihydroxy VitD3, vitamin E, coenzyme Q10, an iron or copper ion chelator such as deferoxamine, deferiprone or deferasirox, baicalin, baicalein, luteolin, quercetin, butein, flower extracts of *Chrysanthemum morifolium* Ramat, leaf extracts of *Cedela sinensis* A. Juss, extracts of *Oenothera stricta* Ledeb., extracts of *Equisetum arvense* L., leaf extracts of *Ipomoea batatas*, tomato extracts and homocysteine. In still another exemplary embodiment of the present invention, the desired cells may be any one type of stem cells selected from the group consisting of adult stem cells, embryonic stem cells and induced pluripotent stem cells; any one type of immune cells selected from the group consisting of dendritic cells, natural killer cells, T cells, B cells, regulatory T cells (Treg cells), natural killer T cells, innate lymphoid cells, macrophages, granulocytes, chimeric antigen receptor-T (CAR-T) cells, lymphokine-activated killer (LAK) cells and cytokine induced killer (CIK) cells; any one type of somatic cells selected from the group consisting of fibroblasts, chondrocytes, synovial cells, keratinocytes, adipocytes, osteoblasts, osteoclasts and peripheral blood mononuclear cells; any one type of cell line used in production of a protein agent, selected from the group consisting of CHO cells, NS0 cells, Sp2/0 cells, BHK cells, C127 cells, HEK293 cells, HT-1080 cells, and PER.C6 cells; or any one type of a human microbiome selected from the group consisting of microorganisms originating from the mouth, nasal cavity, lung, skin, gastric intestinal tract and urinary tract of a human or animal. In yet another exemplary embodiment of the present invention, the first oxidizing agent includes hydroperoxides such as $H_2O_2$ and tert-butyl peroxide; thiol oxidizing agents such as diamide, GSSG (oxidized GSH), 5,5'-dithiobis(2-nitrobenzoic acid), maleimide, N-ethyl maleimide, 4-maleimidobutyric acid, 3-maleimidopropionic acid and iodoacetamide; glutathione reductase inhibitors such as bis-chloroethylnitrozourea; thioredoxin inhibitors such as PX-12; mitochondrial electron transport chain inhibitors such as antimycin A, rotenone, oligomycin and carbonyl cyanide m-chlorophenyl hydrazone; NADPH oxidase activators such as phorbol 12-myristate 13-acetate; gpx4 inhibitors such as 1S,3R-RAS-selective lethal 3 (1S, 3R-RSL3), DPI19, DPI18, DPI17, DPI13, DPI12, DPI10 (ML210), DPI7 (ML162), and altretamine; system $x_c^-$ inhibitors such as erastin, sulfasalazine, sorafenib, glutamate, piperazine erastin, imidazole ketone erastin, and an erastin analog; inducers for reducing GPX4 protein and CoQ10 levels, such as ferroptosis inducer 56 (FIN56); lipid peroxidation inducers such as caspase-independent lethal 56 (CIL56) and endoperoxide ($FINO_2$), which is a ferroptosis inducer; glutamate-cysteine ligase (GCL) inhibitors such as buthionine-(S,R)-sulfoximine; GSH reduction inducers such as diethyl maleate; DPI2, cisplatin, cysteinase, statin, iron ammonium citrate, trigonelline, carbon tetrachloride, silica-based nanoparticles and specific heat plasma. In yet another exemplary embodiment of the present invention, the second oxidizing agent includes maleimide, 4-maleimidobutyric acid, 3-maleimidopropionic acid, ethylmaleimide, N-ethylmaleimide, iodoacetamide, 5,5'-dithiobis(2-nitrobenzoic acid), or iodoacetamidopropionic acid.

FR may be a ratio of a fluorescence intensity (F510) at 430-550 nm to a fluorescence intensity (F580) at 550-680 nm, but the present invention is not limited thereto.

Advantageous Effects

FreSH-Tracer can be used in real-time monitoring of an intracellular GSH level in living stem cells and differentiation of cells according to the GSH level, and the present invention relates to a novel method capable of evaluating the quality of a cell therapeutic agent and improving the quality thereof.

DESCRIPTION OF DRAWINGS

FIG. 3 illustrates graphs showing that FreSH-Tracer can be removed from cells, in which

FIG. 25A illustrates results of analyzing GM, GH and ORC of baicalin in hUC-MSCs, FIG. 25B illustrates results of analyzing GM, GH and ORC of baicalein in hUC-MSCs, FIG. 25C illustrates results of analyzing GM, GH and ORC of luteolin in hUC-MSCs, FIG. 25D illustrates results of analyzing GM, GH and ORC of quercetin in hUC-MSCs, and FIG. 25E illustrates results of analyzing GM, GH and ORC of butein in hUC-MSCs.

FIG. 26A illustrates results of analyzing GM, GH and ORC of a flower extract of *Chrysanthemum morifolium* Ramat in hUC-MSCs, FIG. 26B illustrates results of analyzing GM, GH and ORC of a leaf extract of *Cedela sinensis* A. Juss in hUC-MSCs, FIG. 26C illustrates results of analyzing GM, GH and ORC of an extract of *Oenothera stricta* Ledeb. in hUC-MSCs, FIG. 26D illustrates results of analyzing GM, GH and ORC of an extract of *Equisetum arvense* L. in hUC-MSCs, FIG. 26E illustrates results of analyzing GM, GH and ORC of a leaf extract of *Ipomoea batatas* in hUC-MSCs, and FIG. 26F illustrates results of analyzing GM, GH and ORC of a tomato extract (LYCOBEADS®) in hUC-MSCs.

MODES OF THE INVENTION

Figure 1A:
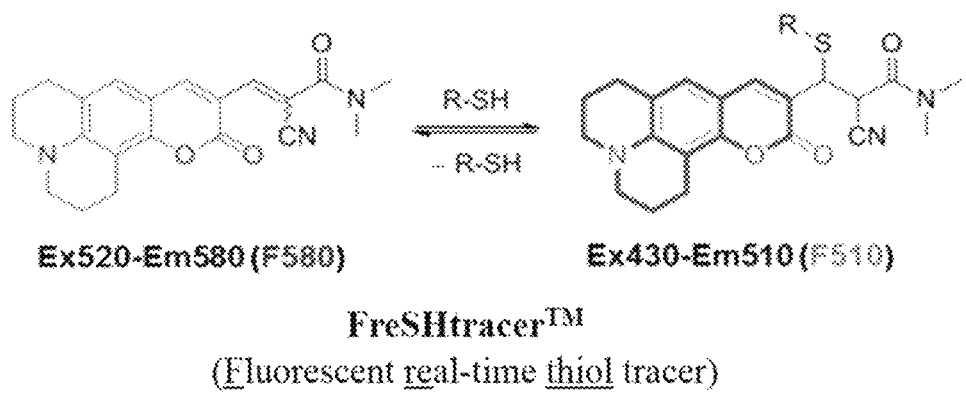
FIG. 1 illustrates a reaction scheme in which FreSH-Tracer of the present invention reversibly reacts with glutathione (GSH) (FIG. 1A), a result of measuring the reversible reaction of FreSH-Tracer by UV-visible absorption spectrometry (FIG. 1B), a result of monitoring the fluorescence emission spectra of FreSH-Tracer, generated by excitation at 430 nm and 520 nm, respectively, at 510 nm (F510) and 580 nm (F580), respectively (FIG. 1C), a graph showing the result of FIG. 1C (FIG. 1D), and an emission ratio which is calculated by dividing the F510 value by the F580 value, i.e., (F510/F580 (FR)) and adjusting the resulting value to an increased concentration of GSH (FIG. 1E).

By using FreSH-Tracer and evaluation parameters according to the present invention in real-time monitoring of an intracellular GSH level in living stem cells and differentiation of cells according to a GSH level, the quality of a cell therapeutic agent may be evaluated, and its quality may be improved.

EXAMPLES

Hereinafter, the present invention will be described in further detail with reference to examples. The examples are merely provided to more fully describe the present invention, and it will be obvious to those of ordinary skill in the art that the scope of the present invention is not limited to the following examples according to the gist of the present invention.

<Preparation of Compounds>

To be used as FreSH-Tracer, a composition including a compound represented by Formula A below or a salt thereof was prepared:

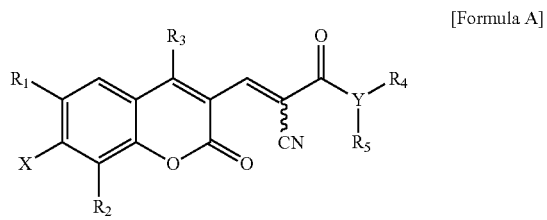

[Formula A]

In Formula A above, $R_1$ and $R_2$ are each independently hydrogen, $C_{1-4}$ linear or branched alkyl, or heterocycloalkyl or heterocycloalkenyl with a 5-membered or 6-membered ring, which is formed of $R_1$, $R_2$ and X; $R_3$ is hydrogen or $C_{1-4}$ linear or branched alkyl; $R_4$ and $R_5$ are each independently hydrogen, $C_{1-5}$ linear or branched alkyl, or —(CH$_2$)$_m$—COO—C$_{1-5}$ linear or branched alkyl (m is an integer of 1 to 5), or $R_4$, $R_5$ and Y form $C_{3-7}$ heterocycloalkyl, and the heterocycloalkyl is unsubstituted or $R_6$-substituted heterocycloalkyl; $R_6$ is —COO(CH$_2$)$_n$—OCO—C$_{1-5}$ linear or branched alkyl (n is an integer of 1 to 5), —(CONH)—(CH$_2$)$_o$—PPh$_3^+$Cl$^-$ (o is an integer of 1 to 5) or —(CONH)—CHR$_7$—COO(CH$_2$)$_p$—OCO—C$_{1-5}$ linear or branched alkyl (p is an integer of 1 to 5); $R_7$ is —(CH$_2$)$_q$—COO(CH$_2$)$_r$—OCO—C$_{1-5}$ linear or branched alkyl (each of q and r is an integer of 1 to 5); and X and Y are each independently N or O.

More preferably, to be used as FreSH-Tracer, the compound represented by Formula A was a compound selected from the group consisting of a compound represented by Formulas A-1 to A-6:

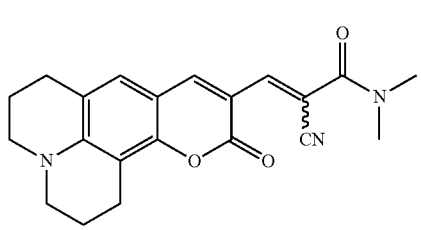

[Formula A-1]

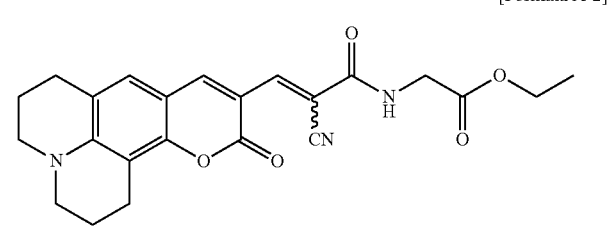

[Formula A-2]

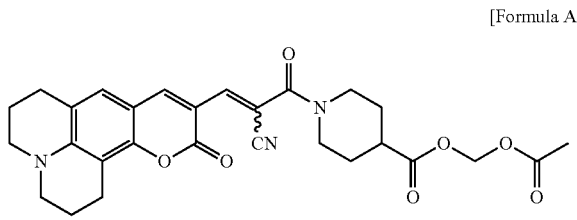

[Formula A-3]

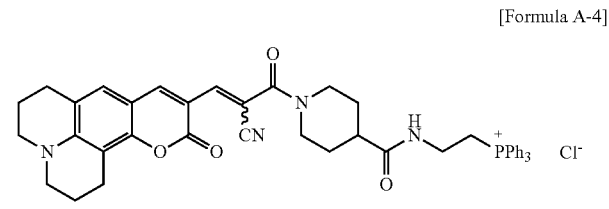

[Formula A-4]

[Formula A-5]

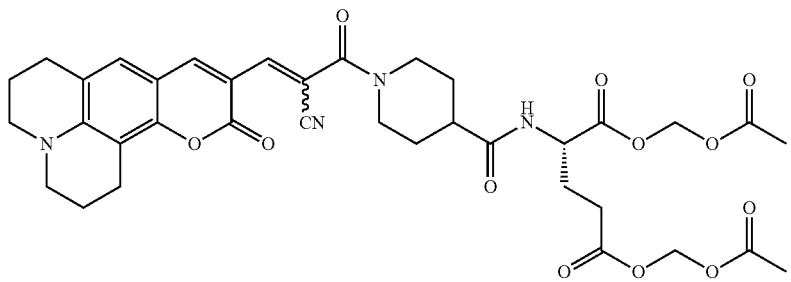

[Formula A-6]

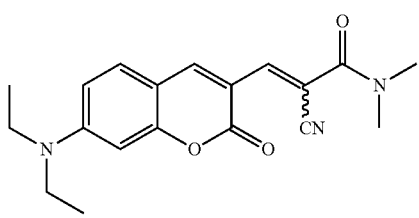

More preferably, as FreSH-Tracer, the compound of Formula A-1 was used.

Subsequently, to be used as MitoFreSH-Tracer, a composition including a compound represented by Formula B below or a salt thereof was prepared:

[Formula B]

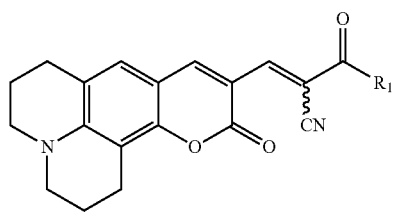

In Formula B above, $R_1$ is heterocycloalkyl, which is a 3 to 7-membered cycle including one or more N atoms, wherein the heterocycloalkyl has a $R_2$ substituent; wherein $R_2$ is —(C(=O)NH)—(CH$_2$)$_m$—PPh$_3^+$Cl$^-$ (m is an integer of 1 to 4), —(CH$_2$)$_n$—PPh$_3^+$Cl$^-$ (n is an integer of 1 to 6), or —(C(=O))—(CH$_2$)$_p$—R$_3$ (p is an integer of 1 to 4); and wherein $R_3$ is —C(NHC(=O)—R$_4$), wherein $R_4$ is a substituent represented by Formula B-1 below.

[Formula B-1]

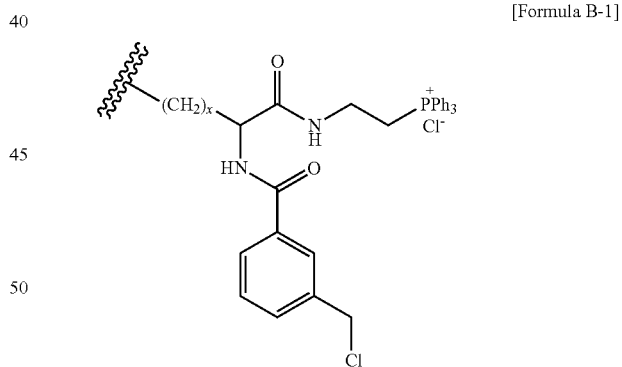

In Formula B-1 above, x is an integer of 1 to 4.

In addition, $R_1$ of the present invention is a 6-membered heterocycloalkyl ring including one or two N atoms. In the present invention, the term "6-membered ring" included in the term "6-membered heterocycloalkyl ring" refers to a single 6-membered ring, which is a monocyclic compound, rather than a ring compound in the form of several conjugated rings, such as a bicyclic compound or a spiro compound, and the "heterocycloalkyl" refers to non-aromatic cyclic alkyl, in which at least one of carbon atoms included in the ring is substituted with a heteroatom, for example, nitrogen, oxygen or sulfur. Preferably, $R_1$ is a 6-membered heterocycloalkyl ring, including one or two nitrogen atoms as heteroatoms included in the ring.

More preferably, to be used as MitoFreSH-Tracer, the compound represented by Formula B was a compound selected from the group consisting of compounds represented by Formulas B-2 to B-4:

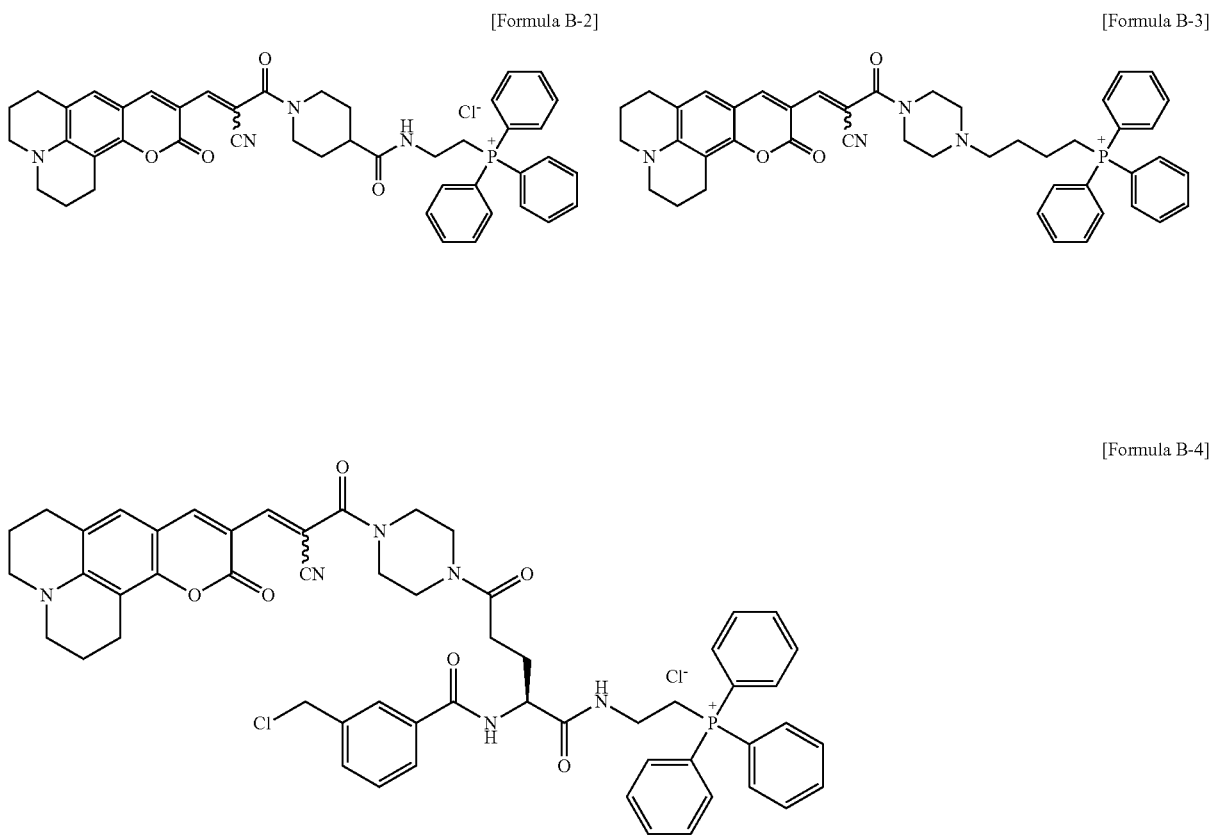

[Formula B-2]

[Formula B-3]

[Formula B-4]

More preferably, as MitoFreSH-Tracer, the compound of Formula B-4 was used.

Subsequently, to be used as GolgiFreSH-Tracer, a composition including a compound represented by Formula B-5 below or a salt thereof was prepared:

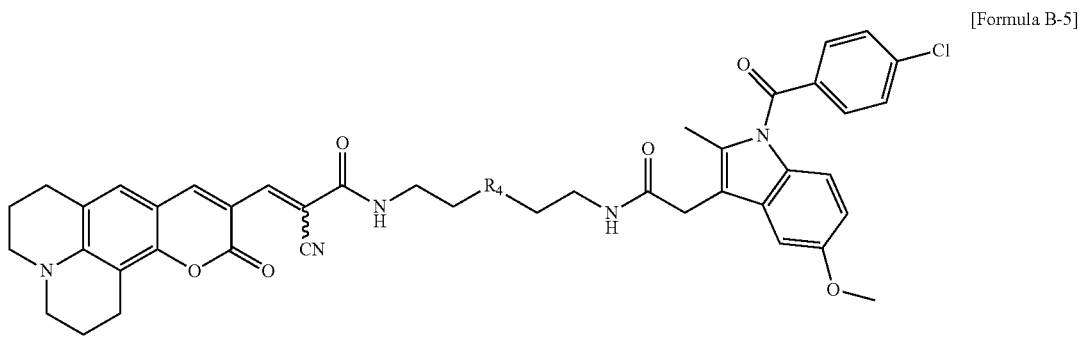

[Formula B-5]

In Formula B-5 above, $R_4$ is a compound of —$(CH_2)p$-$(OCH_2CH_2O)q$-$(CH_2)r$- or —$(CH_2CH_2)s$- (each of p, q, r and s is an integer of 1 to 5). More specifically, in Formula B-5 above, $R_4$ is any one of —$(OCH_2CH_2O)$—, —$(CH_2CH_2)$—, and —$(CH_2(OCH_2CH_2)_2OCH_2)$—.

More preferably, to be used as GolgiFreSH-Tracer, the compound represented by Formula B-5 was a compound selected from the group consisting of compounds represented by Formulas B-6 to B-8:

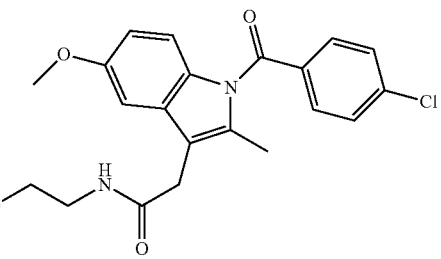
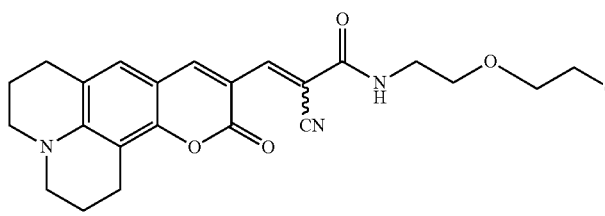

[Formula B-6]

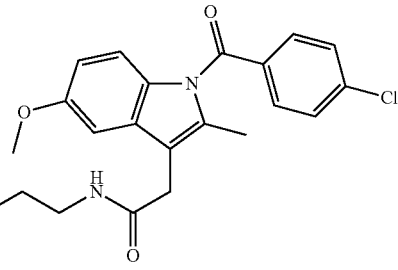
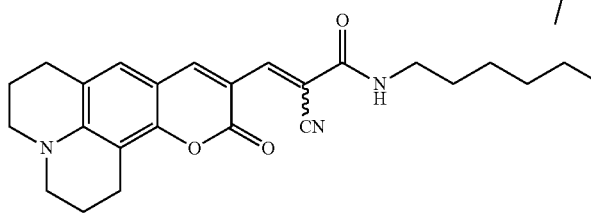

[Formula B-7]

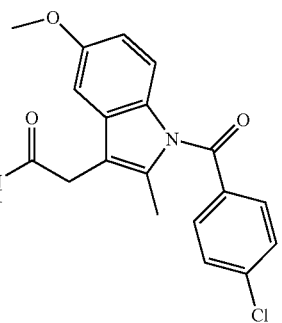
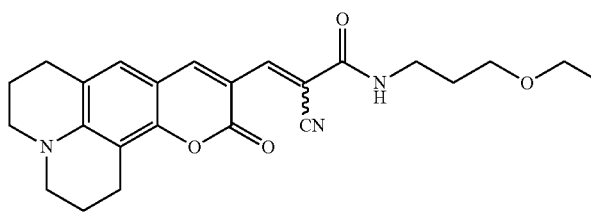

[Formula B-8]

More preferably, as GolgiFreSH-Tracer, the compound of Formula B-8 was used.

By using Compound A or B according to the present invention, or a composition including the same, the antioxidation capacity of a cell organelle such as the mitochondria or the Golgi complex of all cells including stem cells was measured, thereby accurately measuring cell activity related to the antioxidation capacity, and thus cells with high activity can be selected. The cell activity measurement using the composition of the present invention includes measurement of antioxidation capacity, but the present invention is not limited thereto.

In addition, a composition for measuring the antioxidation capacity of a cell organelle, which includes a compound represented by Formula A or B; a racemate thereof, an enantiomer thereof, a diastereomer thereof, a mixture of enantiomers thereof, or a mixture of diastereomers thereof; and a pharmaceutically acceptable salt thereof as an active ingredient, was provided.

EXAMPLES

Example 1: Establishment of Experimental Conditions Using FreSH-Tracer and Confirmation of Intracellular Expression Pattern Cell activity of living cells was measured using FreSH-Tracer, and to isolate cells with high cell activity, experimental conditions were established as follows.

Human bone marrow mesenchymal stem cells (hBM-MSCs, purchased from Lonza), human umbilical cord-derived mesenchymal stem cells (hUC-MSCs, derived from an umbilical cord sample provided by the Obstetrics and Gynecology Department of Seoul National University), and human embryonic stem cell-derived mesenchymal stem cells (hES-MSCs, provided by Prof. Hyung-Min Chung, Konkuk University, Korea) were used.

Here, the compound of Formula A-1 below was used as FreSH-Tracer, the compound of Formula B-4 below was used as MitoFreSH-Tracer, and the compound of Formula B-8 below was used as GolgiFreSH-Tracer.

Figure 1B:
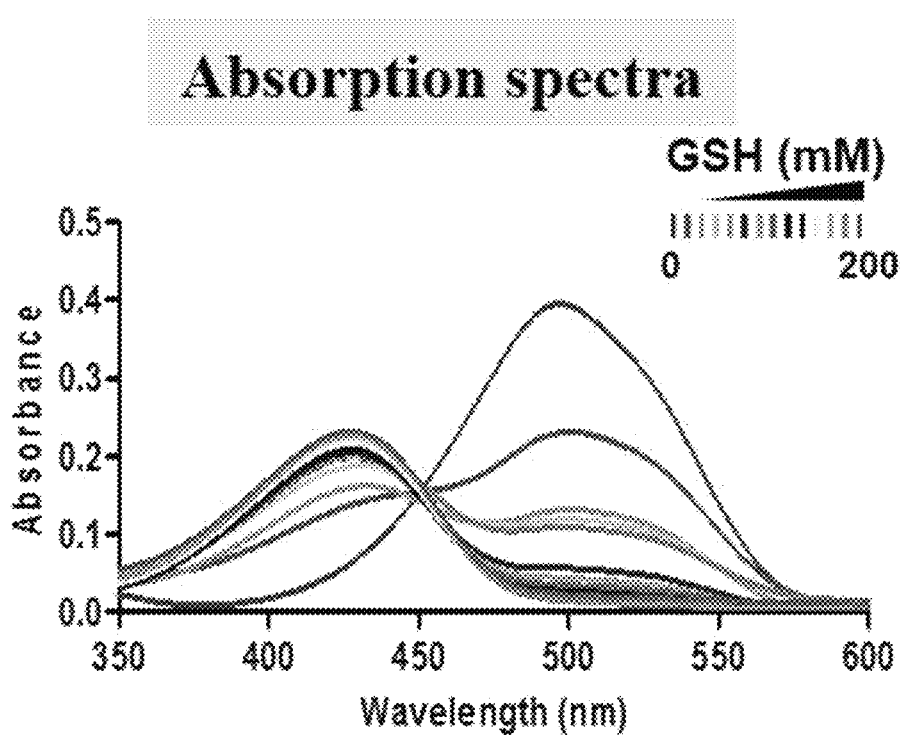
Figure 1C:
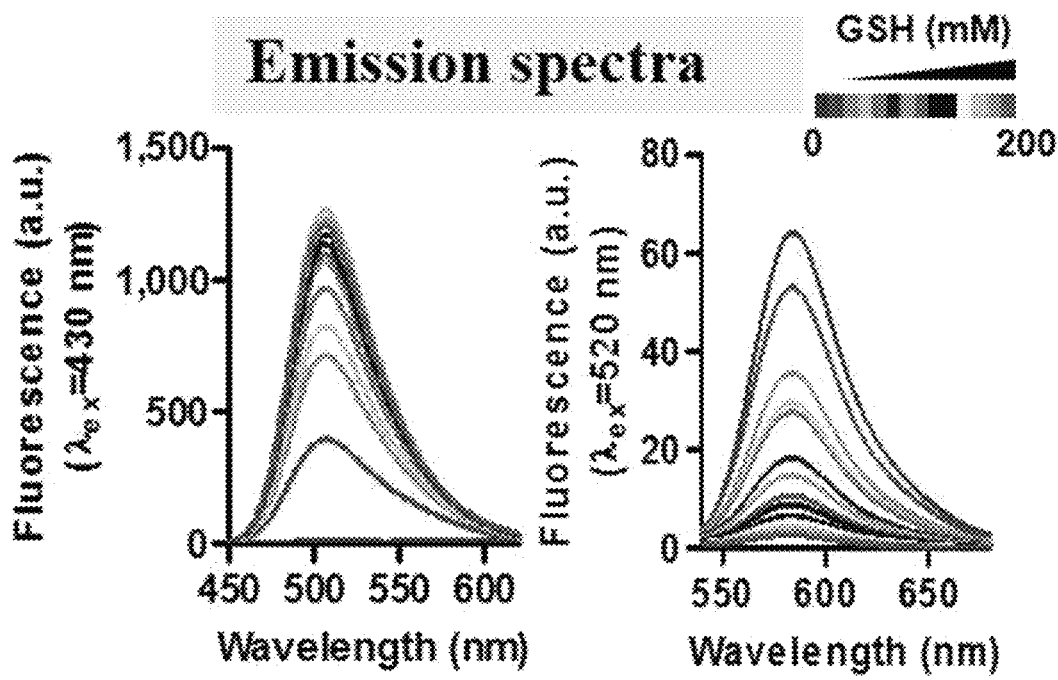
Figure 1D:
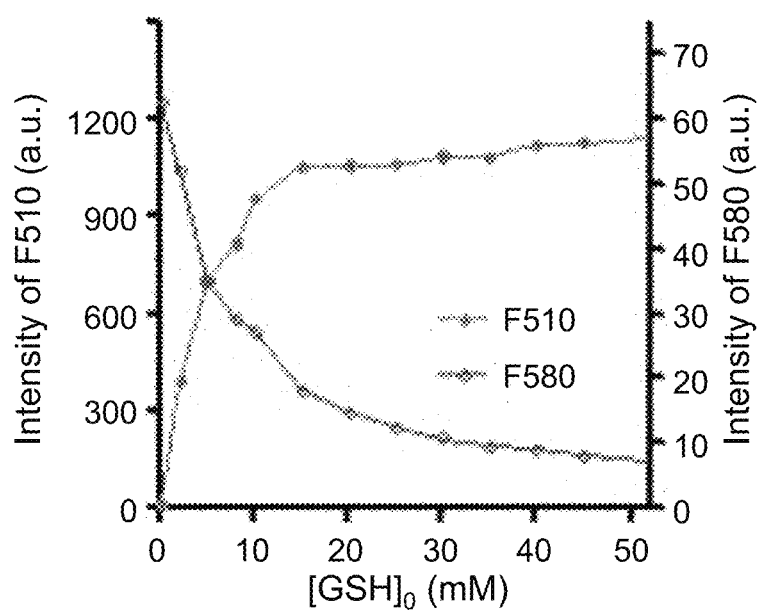
Figure 1E:
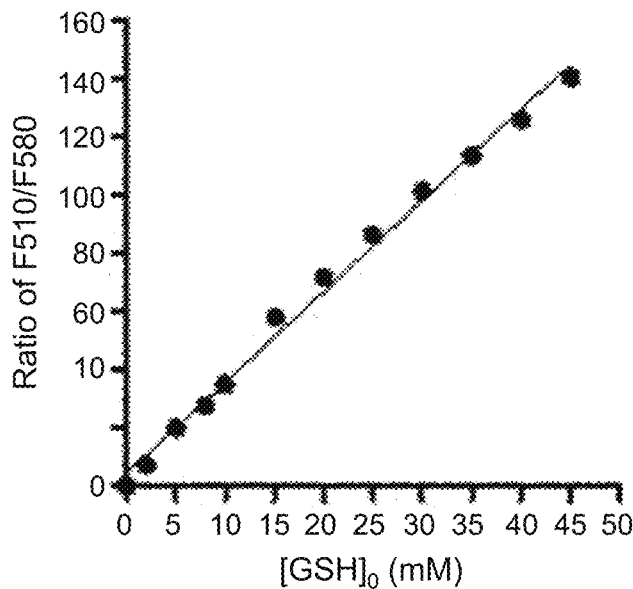

A buffer mixture (10 mM phosphate, 150 mM NaCl, pH 7.4, H2O:DMSO=98:2) was prepared by mixing GSH (0 to 200 mM) and FreSH-Tracer (10 μM), and time-dependent changes of the UV-visible light absorption spectrum and the fluorescence emission spectrum of the solution were measured using Scinco S-3100 and Hitachi F-7000 spectrophotometers, respectively. Specifically, when GSH was added to FreSH-Tracer while increasing the concentration thereof, absorbances with respect to UV and visible light increased at λmax=430 nm and decreased at λmax=520 nm (FIG. 1A), and a fluorescence emission intensity increased at approximately 510 nm (F510, λex=430 nm; λem=510 nm) and decreased at approximately 580 nm (F580, λex=520 nm; λem=580 nm) (FIGS. 1B and 1C). In addition, it was confirmed that a fluorescence emission intensity ratio of F510 to F580 (F510/F580, FR) of FreSH-Tracer is proportionally changed in a wide range of GSH concentrations (FIG. 1D). A regression curve obtained from the FR fluorescence ratio showed linearity (R2=0.9938) in a concentration range (0 to 50 mM) wider than the range of concentrations of GSH present in cells (FIG. 1E).

Moreover, absorbances with respect to UV and visible light of various derivatives (Compound A or B above) included in FreSH-Tracer also increased at λmax=430 nm and decreased at λmax=520 nm, and the fluorescence emission intensities thereof increased at F510, and decreased at F580. Likewise, it was confirmed that F510/F580 (FR) was also proportionally changed in a wide range of GSH concentrations, as in the case with Formula B-1 (data not shown). Detailed data can be referenced from Korean Patent Application Nos. 10-2015-0161745 and 10-2017-0107429.

[Formula A-1]

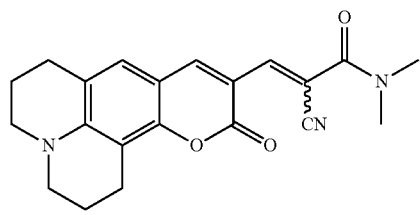

[Formula B-4]

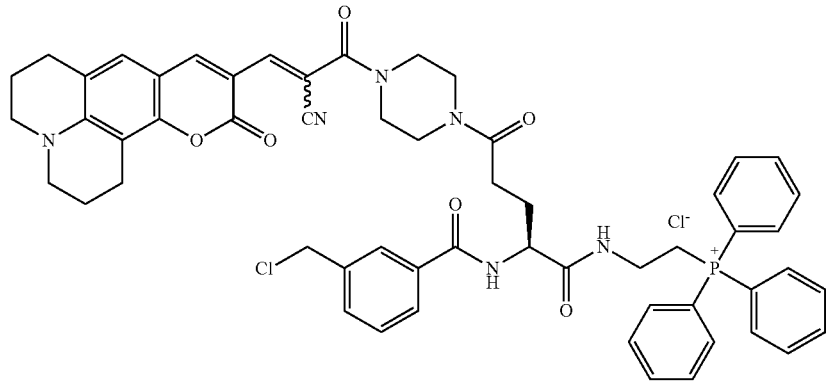

[Formula B-8]

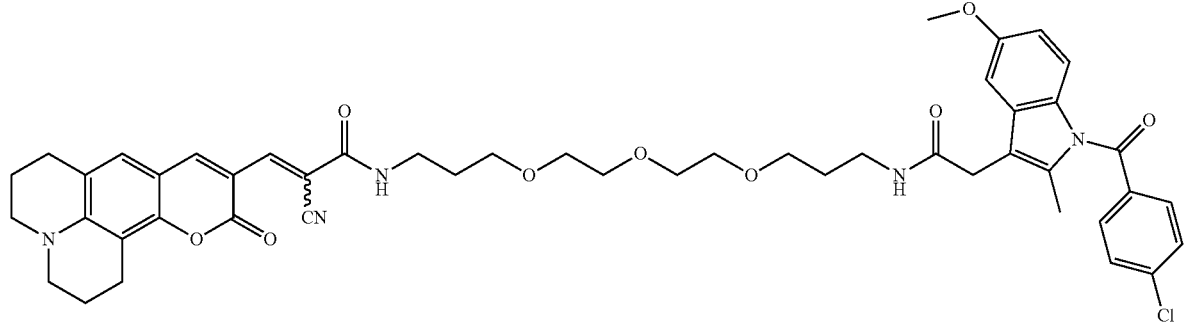

Therefore, such results show that FreSH-Tracer can monitor GSH changes induced by ROS in a cell homogenate.

Example 2: Isolation of Living Cells According to FreSH-Tracer-Based GSH Concentration Using FACS 2-1. Isolation of hBM-MSCs The hBM-MSCs were seeded in a culture medium (MSCGM Bullet Kit; Lonza #PT-3001) at a density of $1\times10^3$ cells/cm$^2$, and three days later, labeled in a culture medium containing 2 μM FreSH for 1.5 hours. The cells were washed with DPBS (WELGENE #LB 001-02) twice and detached with a TrypsinLE (Gibco #12604-013) solution, and trypsin was inactivated with a fresh medium containing 2 μM FreSH. Afterward, after centrifugation at 4° C. and 1800 rpm for 10 minutes, the cells were resuspended in a fresh medium containing 2 μM FreSH. The resulting suspension was diluted 1/5 with PBS containing 2 μM FreSH immediately before loading for FACS (diluted by approximately 1 mL at a time to maintain a temperature of 4° C.).

Afterward, under the following conditions, FACS Instruction (BD ARIAIII, laser at wavelengths of 405 (for measuring F510) and 488 (for measuring F580), nozzle size: 100 μm, 2,000-3,000 events/sec), FACS analysis was performed by gating the cells corresponding to the upper 3.9-35% and the lower 3.9-35% of total cells according to the F510/F580 ratio.

Figure 2:
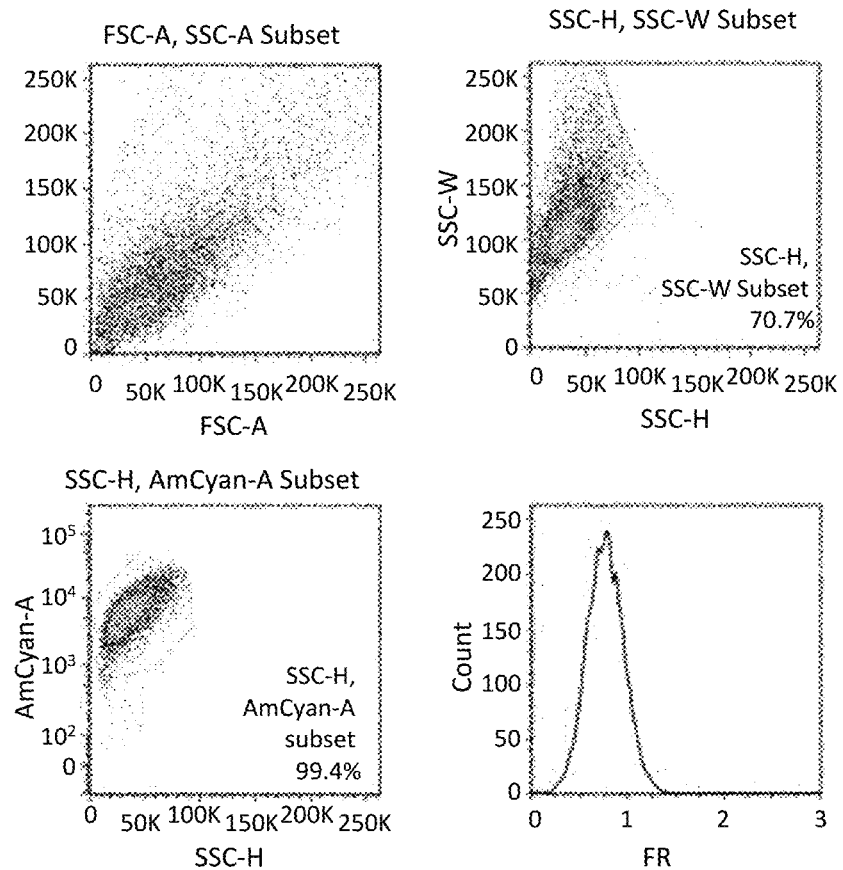
FIG. 2 illustrates graphs illustrating a step for FACS sorting of hBM-MSCs by F510/F580 (FR).
Figure 3A:
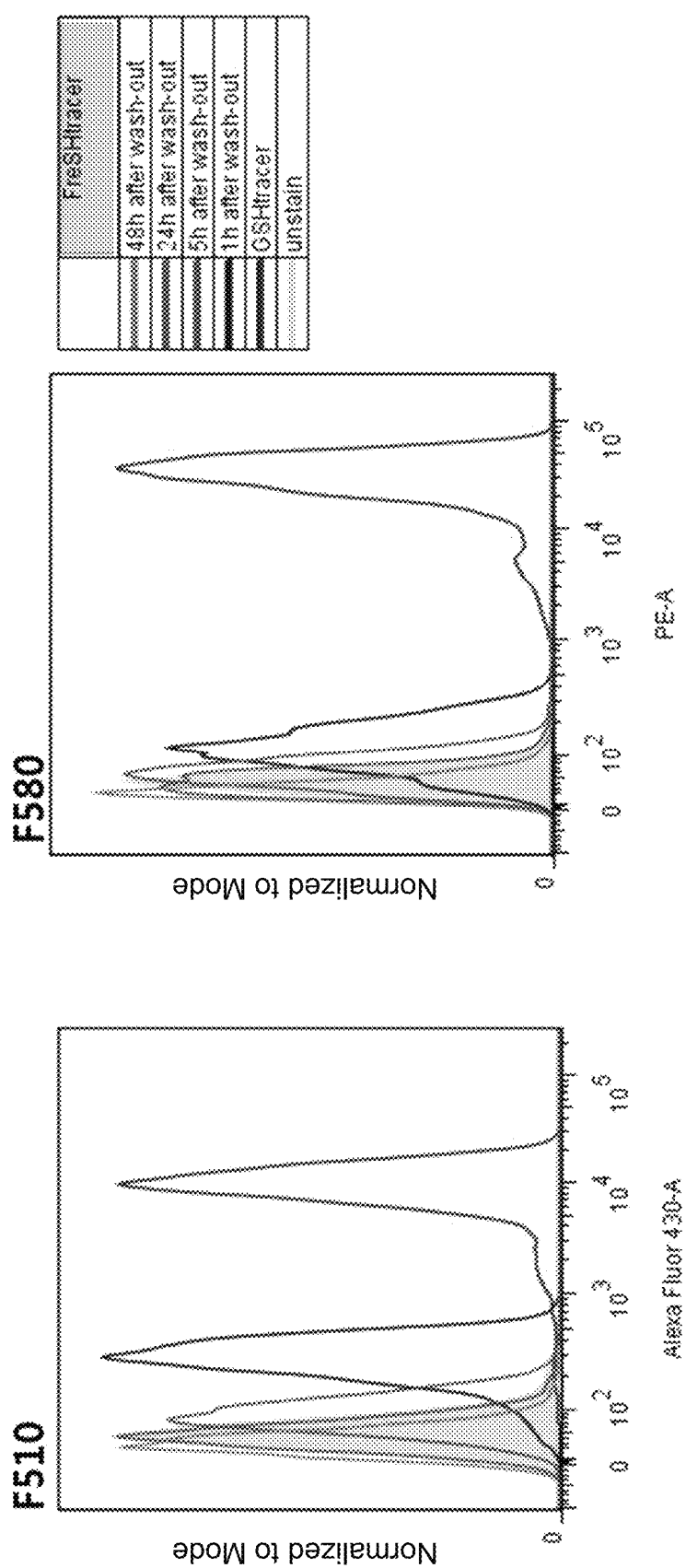
FIG. 3A illustrates a result of FACS analysis over time after FreSH-Tracer-stained cells are washed and then cultured in a new culture medium.
Figure 3B:
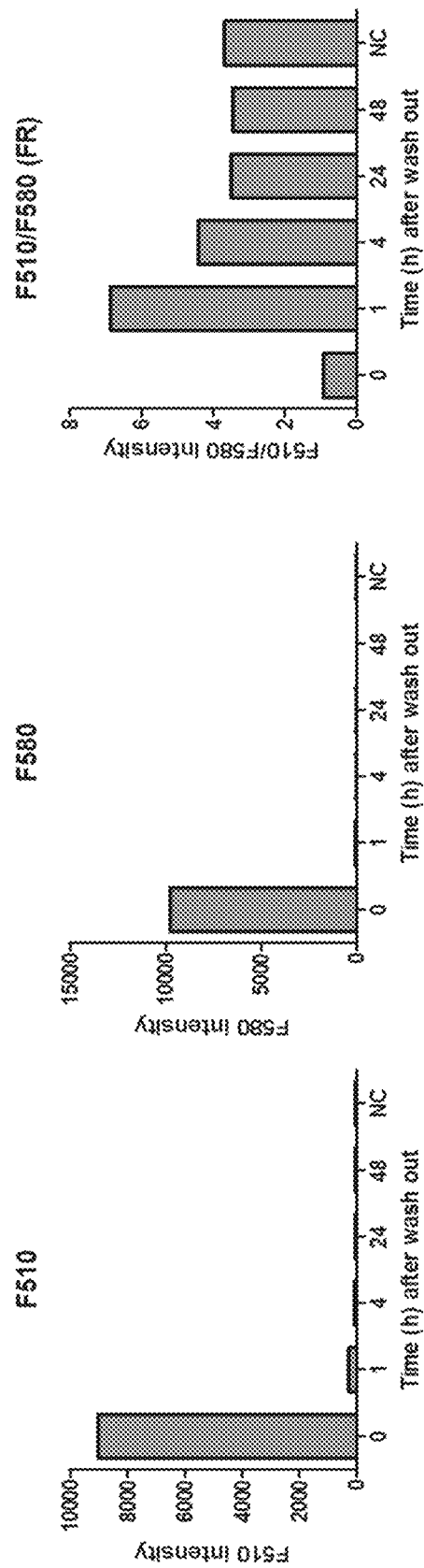
FIG. 3B illustrates a graph obtained by quantifying the result.

The cells were sorted into GSH$^{High}$ (cell population in the upper 1.9-35%), GSH$^{Middle}$ (GSH$^{Mid}$, cell population in the upper 30.2-62.5%) and GSH$^{Low}$ (cell population in the lower 1.9-35%), and then the culture medium was replaced with a fresh medium to remove FreSH-Tracer (FIG. 2). Since FreSH-Tracer reversibly binds to GSH, FreSH-Tracer is removed from the cells by replacing the culture medium (FIG. 3).

2-2. Isolation of Human Diploid Fibroblasts

HDFs isolated from the foreskin of a human penis were prepared as old cells (p32) [replicative aging models according to passage], seeded in 150 pi tissue culture media, and labeled with phenol red-free Dulbecco's Modified Eagle's Medium (DMEM) containing 10% fetal bovine serum containing 2 μM FreSH and 1% penicillin-streptomycin for 2 hours. After the 2 hours, the cells were washed with PBS twice, treated with a TrypsinLE solution (Invitrogen) to detach cells, treated with a fresh medium to inactivate trypsin, and then placed on ice for 5 minutes. Afterward, the cells were centrifuged at 4° C. and 1000 rpm for 10 minutes, and resuspended in a fresh medium containing 2 μM FreSH to have a density of $2\times10^7$ cells/mL.

Subsequently, under the following conditions, FACS Instruction (BD ARIAIII, laser at wavelengths of 405 (for measuring F510) and 488 (for measuring F580), nozzle size: 100 μm), FACS analysis was performed by gating the cells corresponding to GSH$^{High}$ (cell population in the upper 0.2-30.2%) and GSH$^{Low}$ (cell population in the lower 0.2-30.3%) of total cells according to the F510/F580 ratio. Afterward, FreSH was removed by replacing a culture medium with a fresh medium (FIG. 4). Since FreSH reversibly binds to GSH, FreSH is immediately removed from the cells by replacing the culture medium (data not shown).

2-3. Culture of Monocyte-Derived Human Dendritic Cells

Human blood was collected and diluted with DPBS (WELGENE #LB 001-02) to a 3-fold volume, and then only the nucleated cells were isolated by a density difference isolation method using a Ficoll-Paque Plus (GE Healthcare, 17-1440-02) solution. The number of the isolated cells was determined, 90 μL of 2% FBS-containing DPBS and 10 μL of CD14 MicroBead (Milteny Biotech #130-050-201) were added per $1\times10^7$ cells to allow a reaction for 15 minutes at 4° C., and then CD14+ monocytes were isolated using an LS column. The isolated cells were seeded in a 6-well plate at $1\times10^6$ cells/well to perform differentiation in 2 mL of dendritic cell differentiation medium (RPMI 1640, 2 mM L-Glutamine, 10% FBS, 1% penicillin-streptomycin, 100 PM 9-mercaptoethanol, 20 ng/mL hGMCSF, 20 ng/mL IL-4) for 6 days. After the 6 days, the differentiation-completed dendritic cells were considered as immature dendritic cells, and treated with 0.5 μg/mL of LPS for 24 hours to culture mature dendritic cells.

As described in Example 2-1, the cells were labeled with a FreSH-containing medium.

2-4. Isolation of Rat T Lymphocytes

A 24-well plate was coated with 5 μg/mL of CD3 antibodies (Biolegend #100340) at 37° C. for 4 hours, and washed with DPBS. T lymphocytes isolated from the spleen and lymph node of a mouse using Mouse Pan T Cell Isolation Kit II (Milteny Biotech #130-095-130) were added at $2\times10^6$ cells/well, and cultured in a 10% FBS-containing RPMI 1640 medium along with 1 μg/mL of CD28 antibodies (Biolegend #102112) for 3 days. FreSH was added to the culture medium to have a final concentration of 2 μM to label the cells for 2 hours, and the resulting culture solution was centrifuged at 4° C. and 1500 rpm for 5 minutes and resuspended in a fresh medium containing 2 μM FreSH to have a density of $2\times10^7$ cells/mL. Afterward, under the following conditions, FACS Instruction (BD ARIAIII, laser at wavelengths of 405 (for measuring F510) and 488 (for measuring F580) and a nozzle size of 70 μM), the cells were sorted into three types of cell populations according to a F510/F580 ratio.

2-5. Isolation of hES-MSCs

Twelve hours after hES-MSCs were seeded in 150 pi tissue culture media at a density of $3\times10^6$ cells/mL, the cells were washed two times with 30 mL of PBS, and labeled with an EGM-2 MV culture solution containing 2 μM FreSH for 2 hours. After the two hours, the cells were washed with 2 μM FreSH-containing PBS twice and treated with a TrypsinLE (Invitrogen) solution to detach the cells, and then trypsin was inactivated with a fresh EGM-2 MV medium containing 2 μM FreSH. Afterward, the cells were centrifuged at 4° C. and 2000 rpm for 20 minutes, and resuspended in a fresh EGM-2 MV medium containing 2 μM FreSH to have a density of $5\times10^7$ cells/mL. The suspension was diluted 1/5 with PBS containing 2 μM FreSH immediately before loading for FACS (diluted by approximately 1 mL at a time to maintain a temperature of 4° C.).

Afterward, under the following conditions, FACS Instruction (BD ARIAIII, laser at wavelengths of 405 (for measuring F510) and 488 (for measuring F580), nozzle size: 100 μm, 2,000-3,000 events/sec), FACS analysis was performed by gating the cells corresponding to the upper 3.9-35% and the lower 3.9-35% of total cells according to the F510/F580 ratio.

After the cells were sorted into GSH$^{High}$ (cell population in the upper 3.9-35%) and GSH$^{Low}$ (cell population in the lower 3.9-35%), the culture medium was replaced with a fresh culture medium (EGM-2-MV media, LONZA) to remove FreSH (FIG. 4). Since FreSH reversibly binds to GSH, FreSH was immediately removed from the cells by replacing the culture medium (data not shown).

Figure 4A:
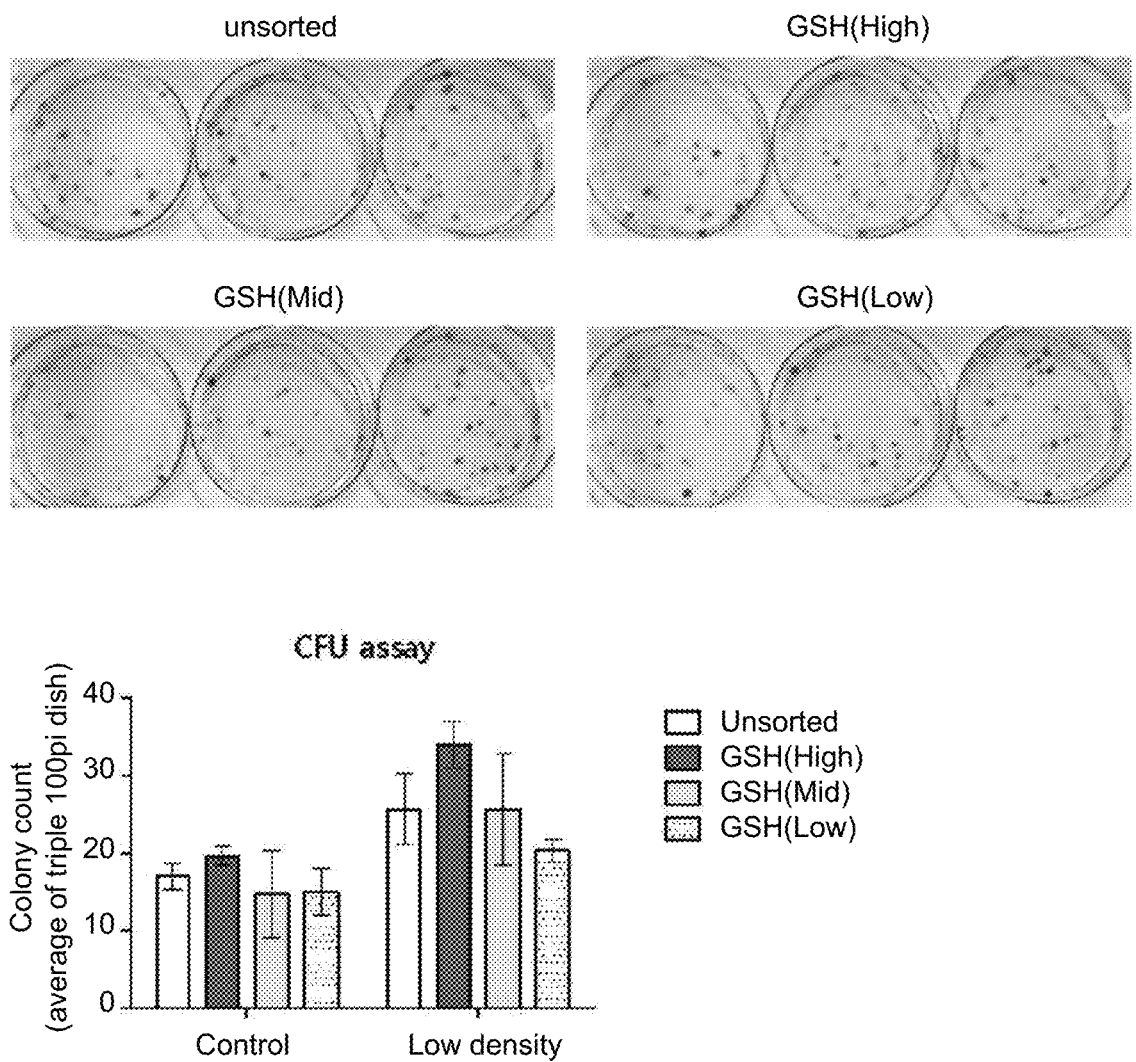
FIG. 4 illustrates the CFU-F of hBM-MSCs sorted by FACS based on FreSH-Tracer (FIG. 4A) and a result of measuring migration capacities by SDF-1α and PDGF-AA (FIG. 4B).
Figure 4B:
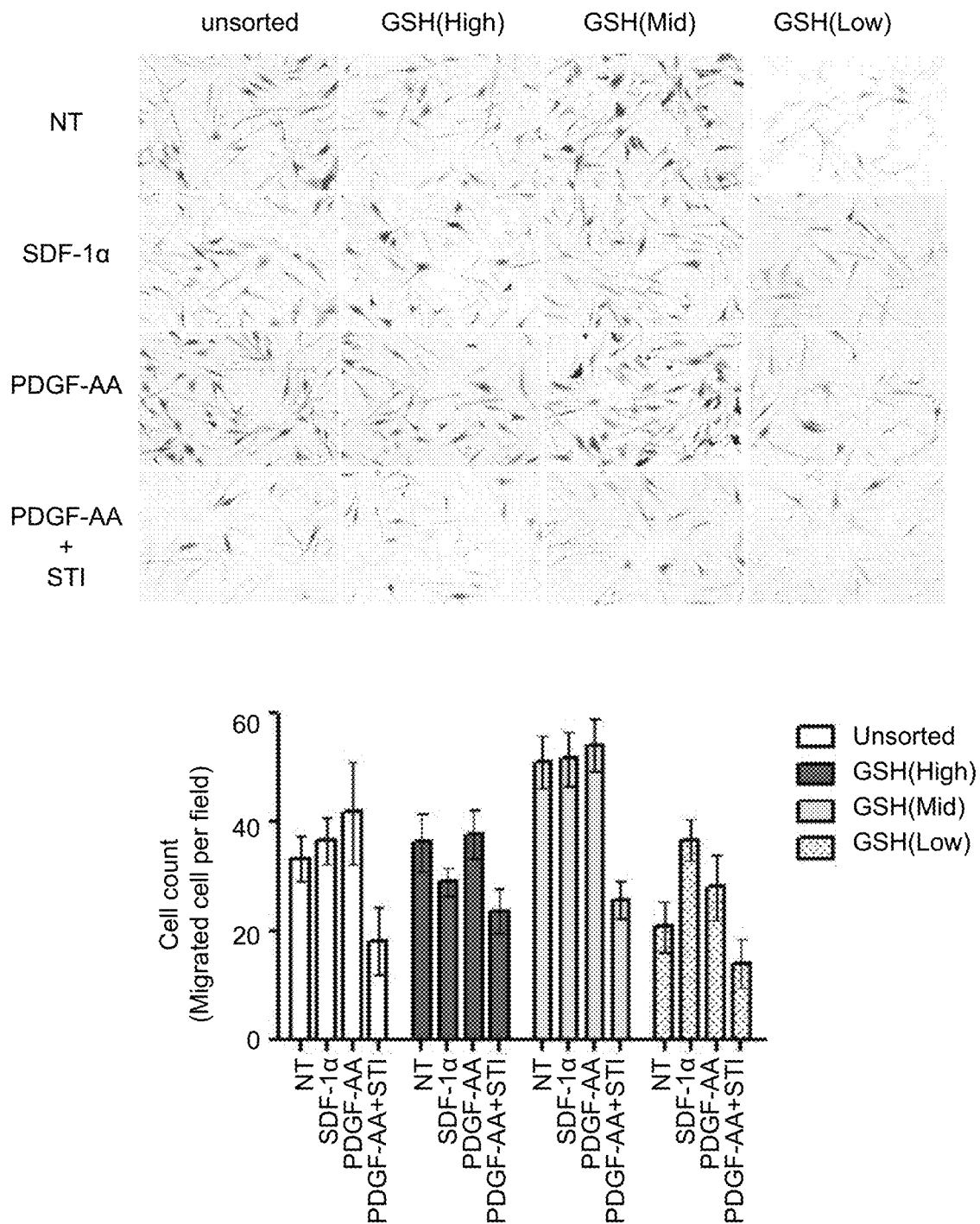

Example 3: Analysis of Characteristics of Sorted Cells 3-1: Analysis of Cytological Characteristic of FreSH-Tracer-Based Sorted Stem Cells Main factors for determining the therapeutic efficacy of hBM-MSCs, namely a colony forming unit-fibroblast (CFU- F) and a graft survival rate, were evaluated in cell culture models. Cells were seeded at 200 cells/100 pi dish and cultured for 14 days, and by subsequent crystal violet staining, it was confirmed that $GSH^{High}$ cells exhibit a considerably higher CFU-F level than $GSH^{Mid}$ or $GSH^{Low}$ cells (FIG. 4A). In addition, chemotaxis for SDF-1 (150 ng/mL) or PDGF-AA (10 ng/mL)±STI571 (0.5 μg/mL) was measured using Transwell culture, confirming that the $GSH^{High}$ cells exhibit a considerably higher cell migration than the $GSH^{Low}$ cells (FIG. 4B).

3-2: Analysis of Aging Characteristic in FreSH-Tracer-Based Sorted Fibroblasts

Figure 5A:
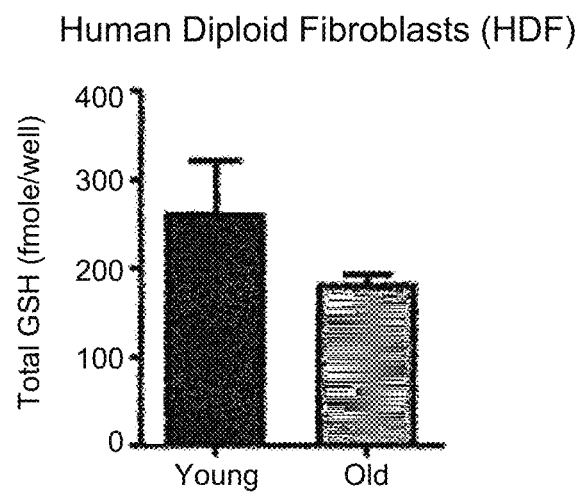
FIGS. 5A to 5F illustrate the anti-aging activity of fibroblasts sorted by FreSH-Tracer.

Human diploid fibroblasts (HDFs) isolated from the foreskin of a human penis were prepared as young cells (p6) and old cells (p32) [replicative aging models according to passage], and afterward, when a GSH level was measured using a GSH/GSSG-Glo™ analysis kit produced by Promega, it was confirmed that the GSH level of the young cells, compared with the old cells, was decreased by approximately 44% (FIG. 5A).

Figure 5B:
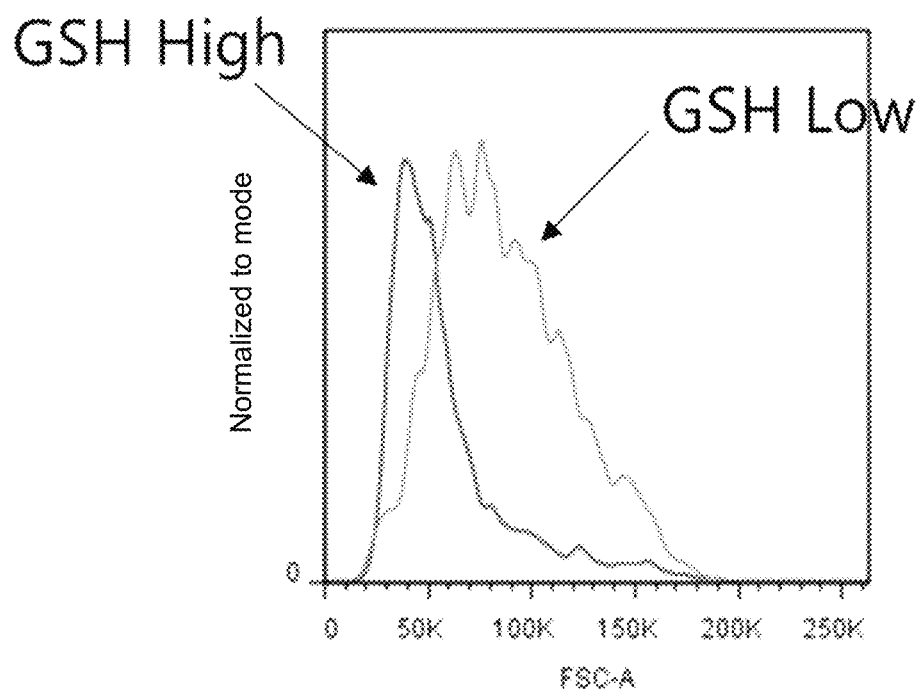
Figure 5C:
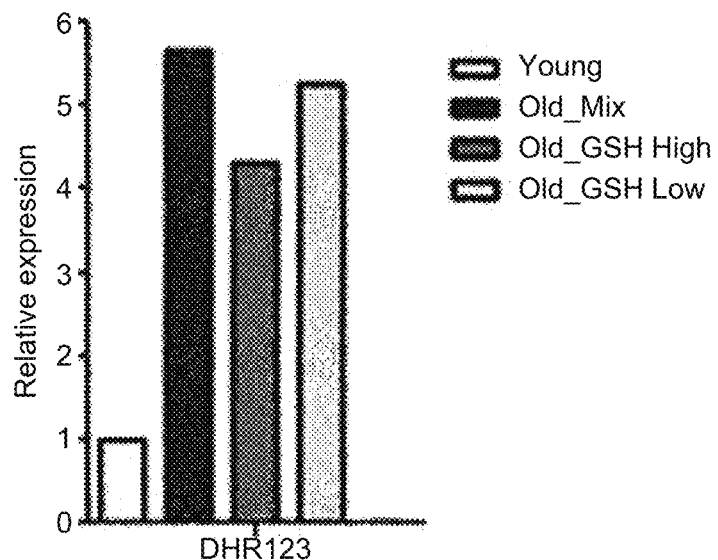

The HDFs were sorted into $GSH^{High}$ and $GSH^{Low}$ fibroblasts by the method described in Example 2-2. As a result of measuring a cell size, it was confirmed that the $GSH^{Low}$ cells have a 1.5-fold larger size compared with the $GSH^{High}$ cells, and it was confirmed that the result corresponds to a previous report (see Reference 1) in that as aging progresses, the cell size (forward scattering (FSC)) becomes larger (FIG. 5B). When the cells were treated with 5 μM dihydrorhodamine 123 (DHR123) and cultured for 30 minutes at 37° C. to measure an intracellular ROS level, it was confirmed that the $GSH^{Low}$ cells are better stained than the $GSH^{High}$ cells (FIG. 5C).

Figure 5D:
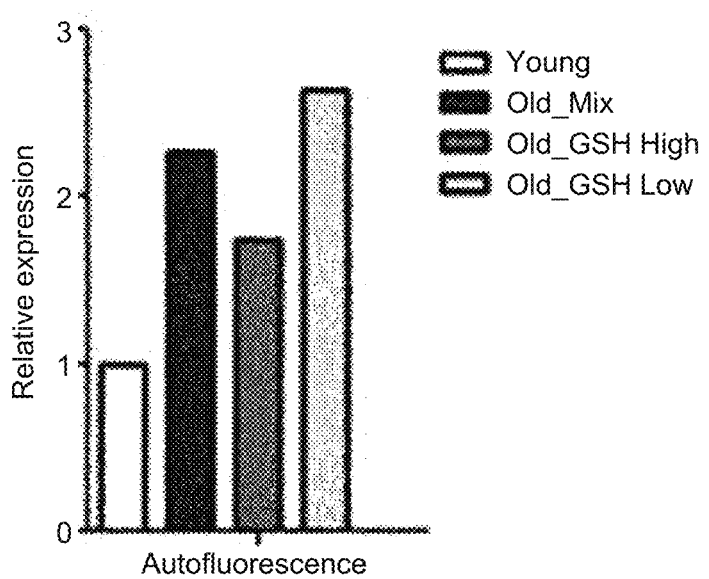
Figure 5E:
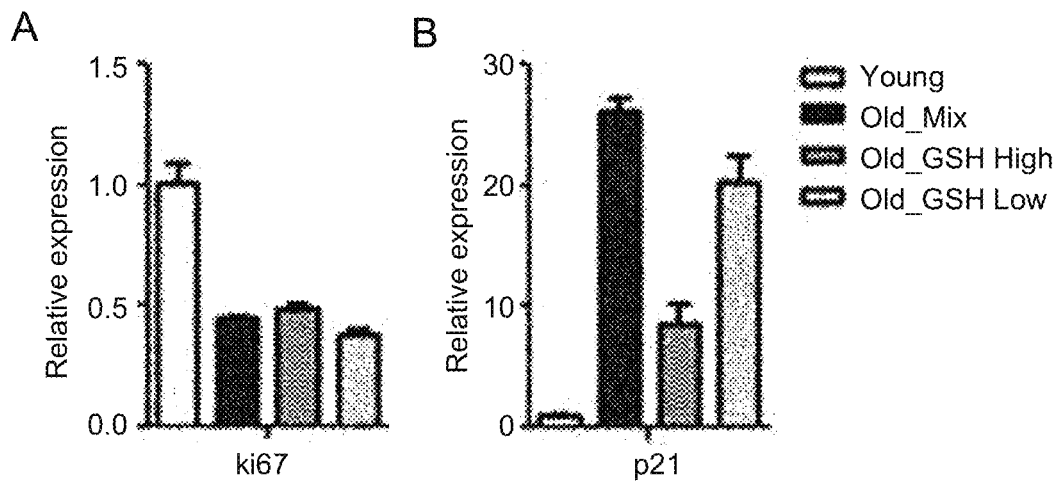
Figure 5F:
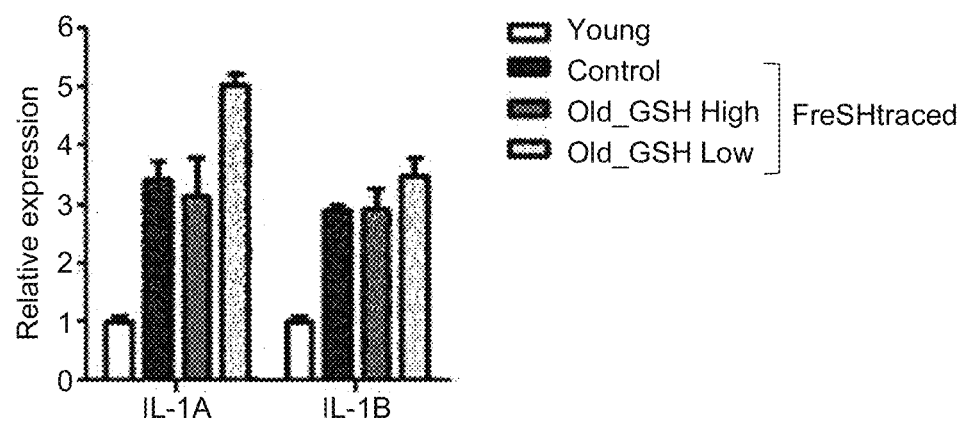

In addition, when a lipofuscin level was measured and quantified by autofluorescence using an Alexa488 fluorescence filter, the $GSH^{Low}$ cells were more strongly measured than the $GSH^{High}$ cells (FIG. 5D), and the $GSH^{Low}$ cells exhibited a lower ki67 mRNA expression level than the $GSH^{High}$ cells, but exhibited a higher mRNA expression level of p21 (FIG. 5E). In addition, when the expression level of SASP-related genes was analyzed by RQ-PCR as described above, it was confirmed that the $GSH^{Low}$ cells were increased in the expression of the IL-1A gene and IL-1B gene, compared with the $GSH^{High}$ cells (FIG. 5F). It has been known that, according to aging of the cells, the lipofuscin level increases (see Reference 2), the ki67 expression level decreases, the p21 expression level increases (see Reference 3), and the expression level of senescence-associated secretory phenotype (SASP)-related genes increases (see Reference 4), and in accordance therewith, the $GSH^{High}$ cells have higher anti-aging activity than the $GSH^{Low}$ cells. The gene expression in this example was measured using the above-described RQ-PCR analysis, and all primers used in this analysis were designed using QuantPrime, and the sequences of the primers are shown in Table 1 below.

TABLE 1

| Name of primer | Primer sequence (5' → 3') |
|---|---|
| IL1A_For | TGTGACTGCCCAAGATGAAGACC (SEQ ID NO: 01) |
| IL1A Rev | TTGGGTATCTCAGGCATCTCCTTC (SEQ ID NO: 02) |
| IL1B_For | GAACTGAAAGCTCTCCACCTCCAG (SEQ ID NO: 03) |

TABLE 1-continued

| Name of primer | Primer sequence (5' → 3') |
|---|---|
| IL1B Rev | AAAGGACATGGAGAACACCACTTG (SEQ ID NO: 04) |
| Ki67_For | AGCACCTGCTTGTTTGGAAGGG (SEQ ID NO: 05) |
| Ki67 Rev | ACACAACAGGAAGCTGGATACGG (SEQ ID NO: 06) |
| p21 For | GGCAGACCAGCATGACAGATTTC (SEQ ID NO: 07) |
| p21_Rev | AGATGTAGAGCGGGCCTTTGAG (SEQ ID NO: 08) |

3-3: Analysis of Immune Activity in FreSH-Tracer-Based Sorted Dendritic Cells

Figure 6:
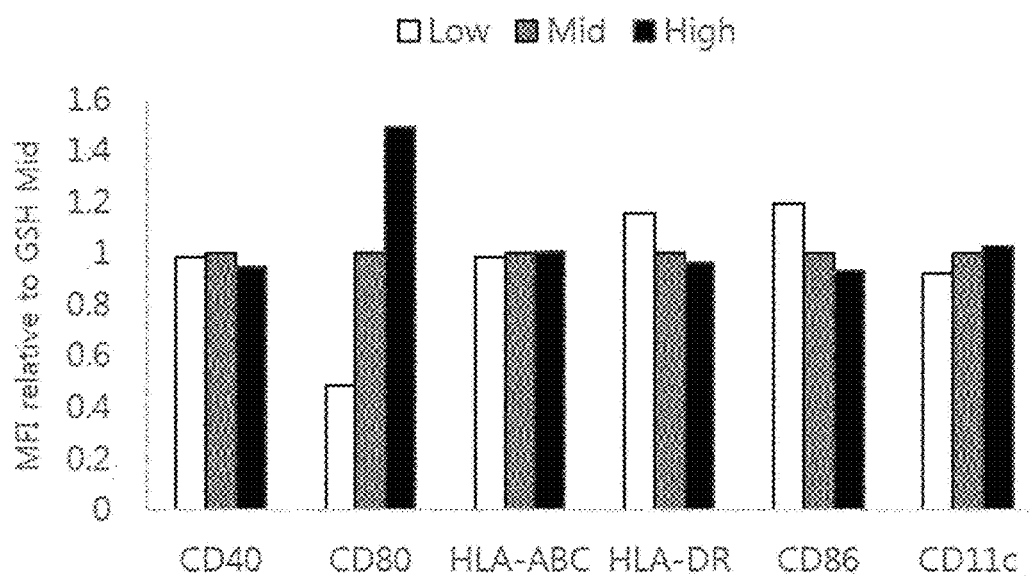
FIG. 6 illustrates the activity of dendritic cells sorted by FreSH-Tracer.
Figure 6:
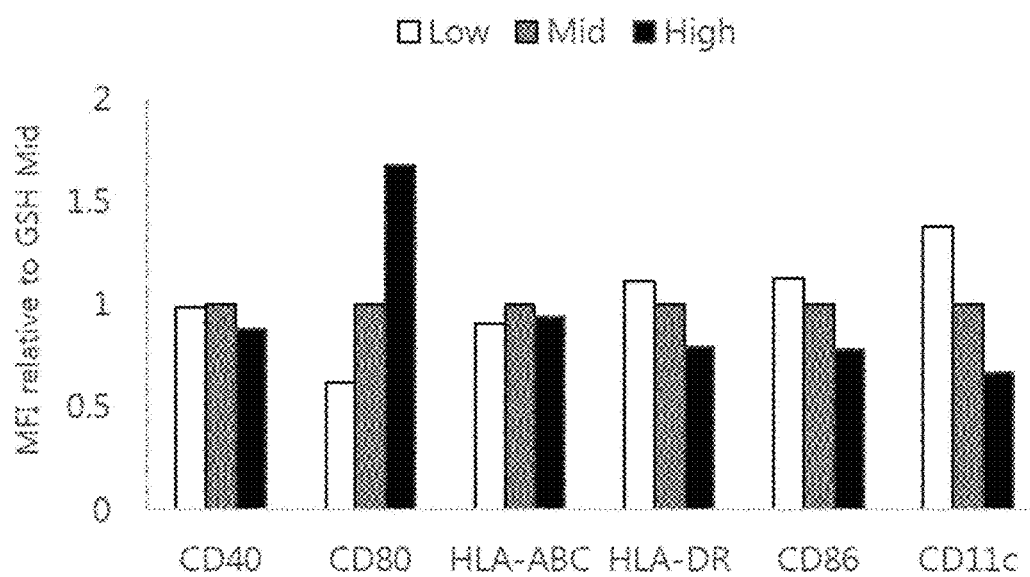

After antibodies against various surface proteins related to immune activity of human monocyte-derived dendritic cells and FreSH-Tracer were simultaneously stained, flow cytometry was performed by gating $GSH^{High}$ (cell population in the upper 0.2-30.2%), $GSH^{Mid}$ (cell population in the upper 30.2-62.5%) and $GSH^{Low}$ (cell population in the lower 0.3-32.7%), and an expression level of the surface protein in each cell population was confirmed. As a result, it was confirmed that an expression level of CD80, which has been known to play a critical role in T-lymphocyte activation, was highest in $GSH^{High}$, then $GSH^{Mid}$, and lowest in $GSH^{Low}$, regardless of maturation of dendritic cells (FIG. 6). Through this, it can be expected that the immune activity of the dendritic cells with a high level of GSH will be high. The surface protein antibodies used in this experiment are shown in Table 2 below.

TABLE 2

| Surface protein | Fluorescence | Manufacturer | Cat. No. |
|---|---|---|---|
| CD40 | AlexaFluor ® 700 | Biolegend | 334328 |
| CD80 | APC | Biolegend | 305220 |
| HLA-DR | BV650 | BD | 564231 |
| CD86 | PE/Cy7 | Biolegend | 305422 |
| HLA-A, B, C | APC/Cy7 | Biolegend | 311426 |
| CD11c | Brilliantviolet711 ™ | Biolegend | 301630 |

3-4: Analysis of Treg Cell Activity in FreSH-Tracer-Based Sorted T Cells

Figure 7:
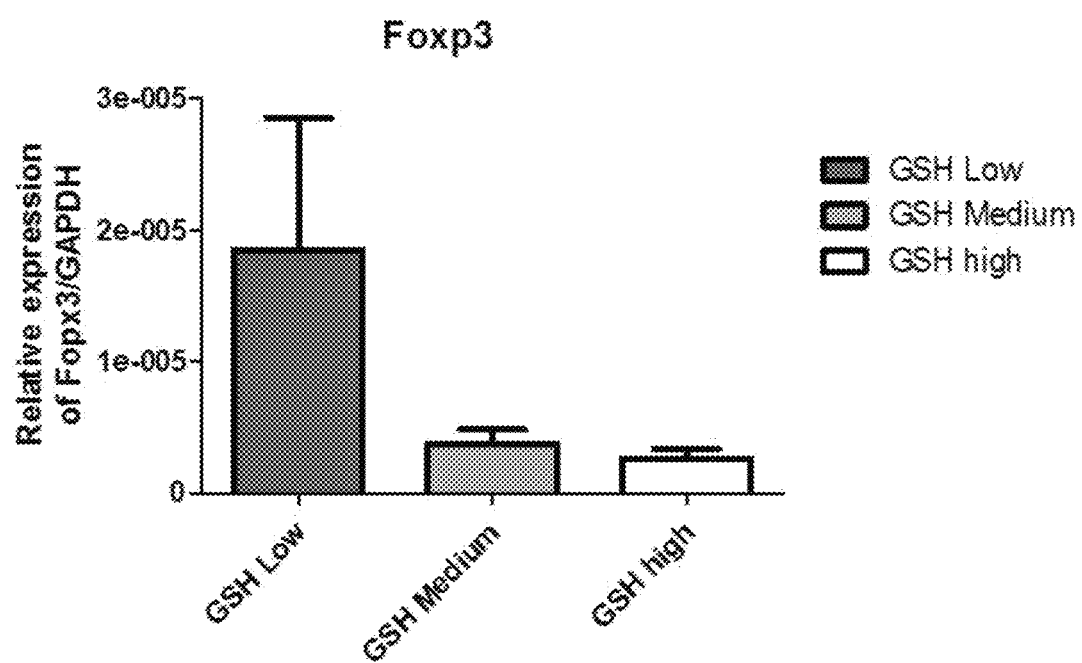
FIG. 7 illustrates the activity of Treg cells in T cells sorted by FreSH-Tracer.

Mouse T lymphocytes were activated using CD3 and CD28 antibodies, and then sorted into three experimental groups according to GSH concentration using FreSH-Tracer. The sorted T lymphocytes were subjected to mRNA extraction using TRIzol (Invitrogen #15596026), the mRNA level of foxp3, which is a Treg cell-specifically expressed transcription factor, was analyzed through RQ-PCR, confirming that the mRNA level of $GSH^{Low}$ was approximately 4-fold higher than $GSH^{High}$ and $GSH^{Mid}$ (FIG. 7). Through this, it can be expected that the ratio of the Treg cells in the T cell population with a high level of GSH will be lower.

Figure 8:
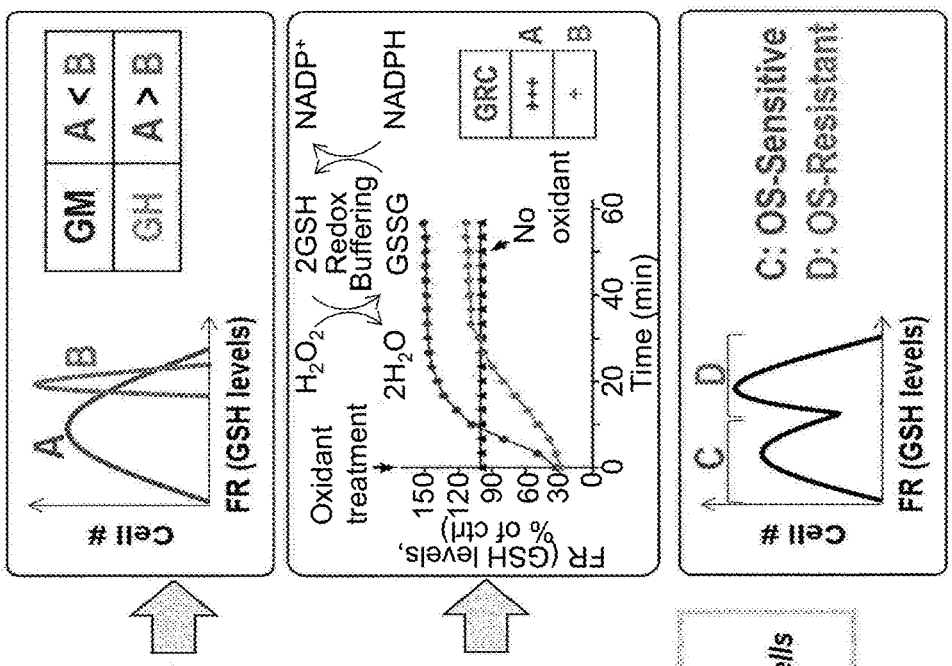
FIG. 8 schematically illustrates four glutathione parameters for evaluating the quality of therapeutic cells, deduced formulas, and the resulting examples.

Example 4: Establishment of Evaluation Parameters for Evaluating Cell Therapeutic Agent Quality Based on FreSH-Tracer To evaluate the quality of therapeutic cells, four evaluation parameters based on a real-time glutathione measurement method using FreSH-Tracer to be described below were developed and analyzed (FIG. 8). The four parameters are a glutathione mean value (or median value; glutathione mean or median level; GM) and glutathione heterogeneity (GH), glutathione regeneration capacity (GRC), and oxidative stress resistance capacity (ORC) of cells, respectively.

As shown in FIG. 8, GM is calculated as the mean or median of cellular FR. In addition, GH is calculated as the coefficient of variation or robust coefficient of variation of cellular FR. GRC refers to a value obtained by real-time monitoring of FR after living cells are treated with an oxidizing agent, as calculated by dividing a value obtained by subtracting AUC of a group treated with 0.1-100 mM N-ethylmaleimide (NEM) from FR AUC of an oxidizing agent (diamide, $H_2O_2$, etc.)-treated group by a value obtained by subtracting the AUC of NEM-treated group from AUC of the untreated control, and multiplying the resulting value by 100. The FR of the NEM-treated group is a value for increasing the sensitivity of a GRC value by treating it as the blank value of the FR of the cells of interest. In addition, to calculate ORC, hUC-MSCs were treated with a 0.5 or 1 μM oxidizing agent such as a glutathione peroxidase 4 (GPX4) inhibitor, RSL3, and cultured at 37° C. for 2 hours. After the removal of an RSL3-containing medium, 15 μM MitoFreSH-Tracer was added per 100 μl, followed by culturing at 37° C. for 1 hour. Here, the medium used in the culture was 10 mM HEPES-containing HBSS(Hanks' balanced salt solution). To remove the MitoFreSH-Tracer from the medium before measurement, the medium was exchanged with fresh 10 mM HEPES-containing HBSS, and a fluorescence image was obtained using a confocal imaging system, Operetta. By comparing GSH levels quantified from control cells not treated with RSL3 or control cells before treated with RSL3, the distribution of GSH expression-changed cells was calculated. Based on the point where the distribution histogram is divided into two peaks, the cells were divided into $GSH^{High}$ cells (right peak) and $GSH^{Low}$ cells (left peak), and then a ratio of corresponding cells was expressed as a percentage (%).

Figure 9A:
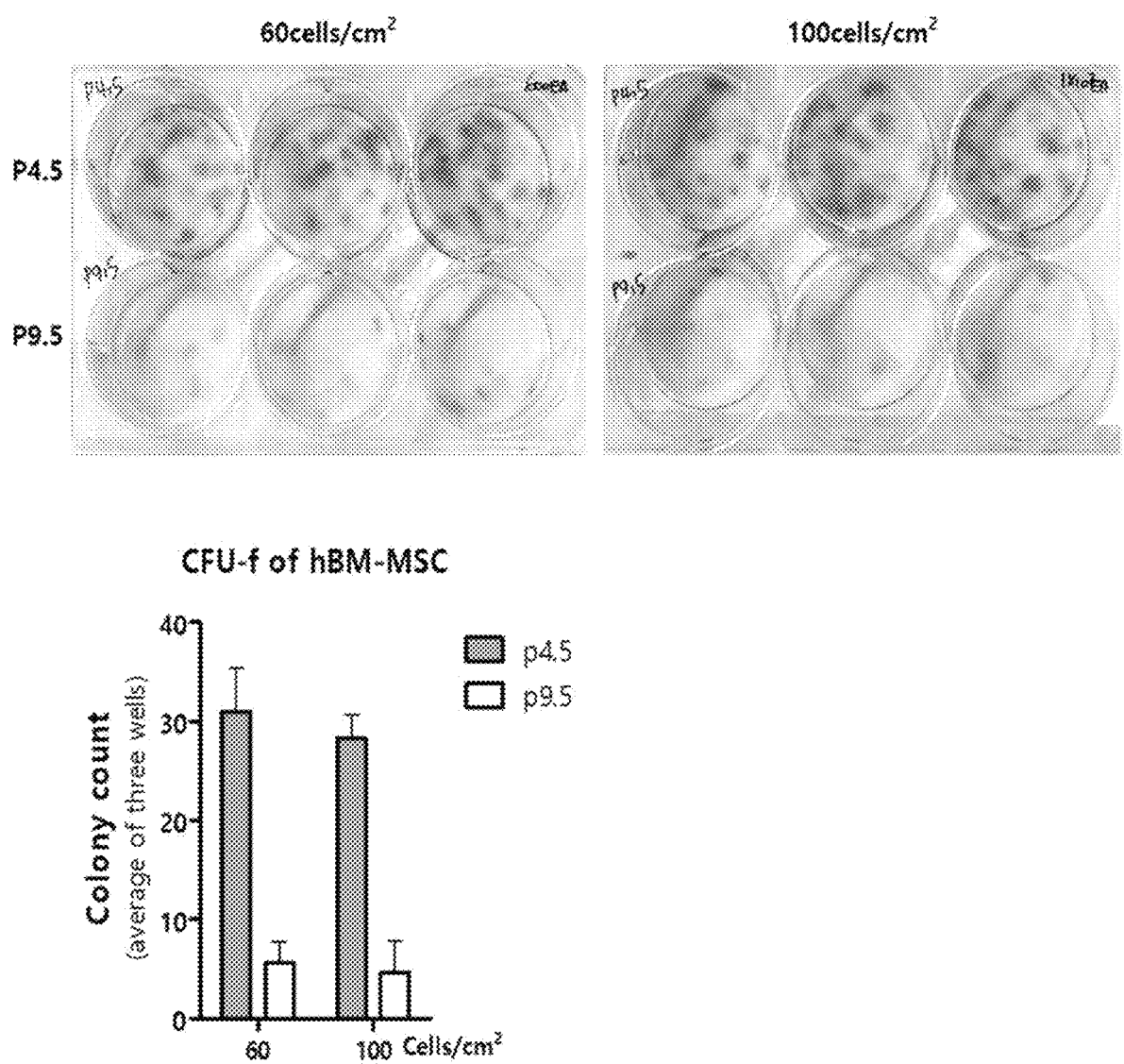
FIG. 9 illustrates a result of CFU-F analysis according to subculture of hBM-MSCs (FIG. 9A) and migration capacity by SDF-1α and PDGF-AA (FIG. 9B).
Figure 9B:
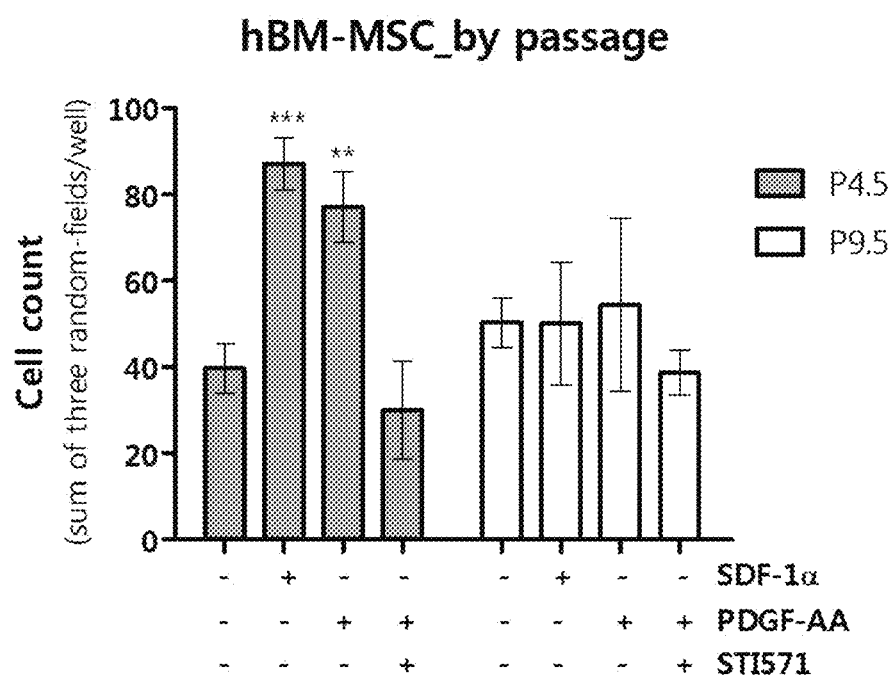
Figure 10A:
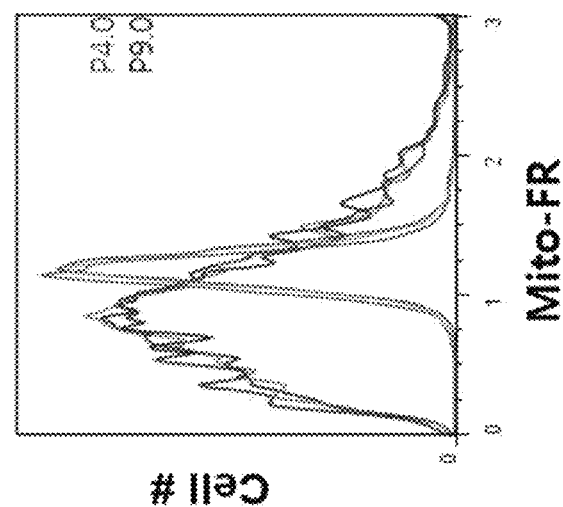
FIGS. 10A to 10C illustrate results of analyzing GM and GH based on FreSH-Tracer, GolgiFreSH-Tracer, or MitoFreSH-Tracer according to subculture of hBM-MSCs.
Figure 10A:
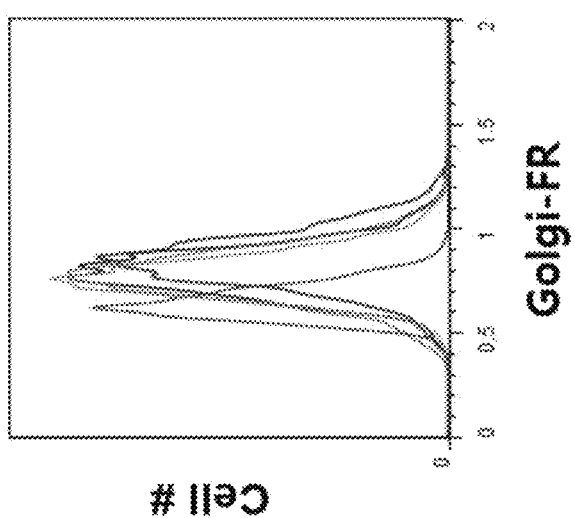
Figure 10A:
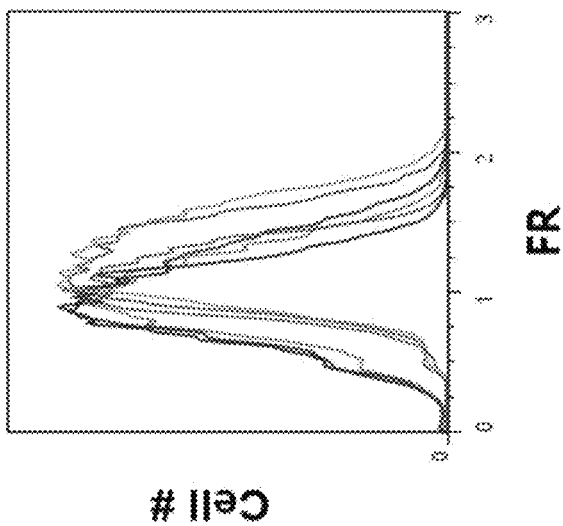
Figure 10B:
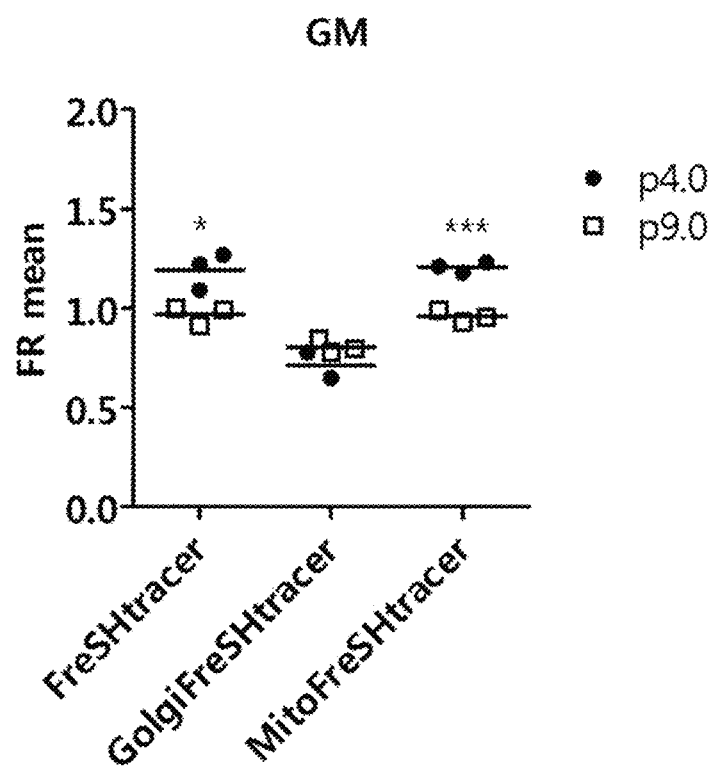
Figure 10C:
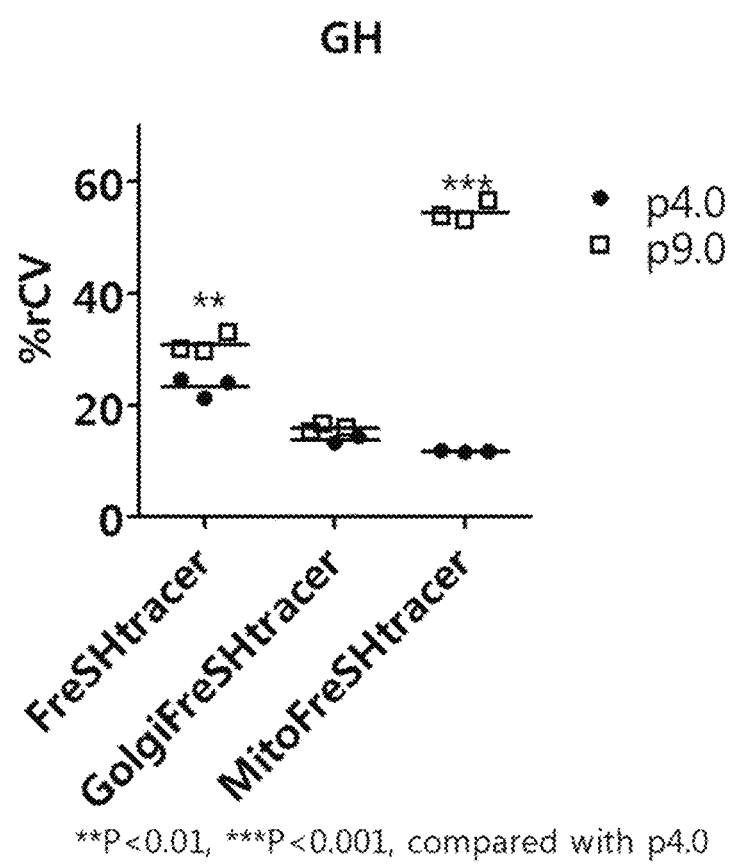
Figure 11:
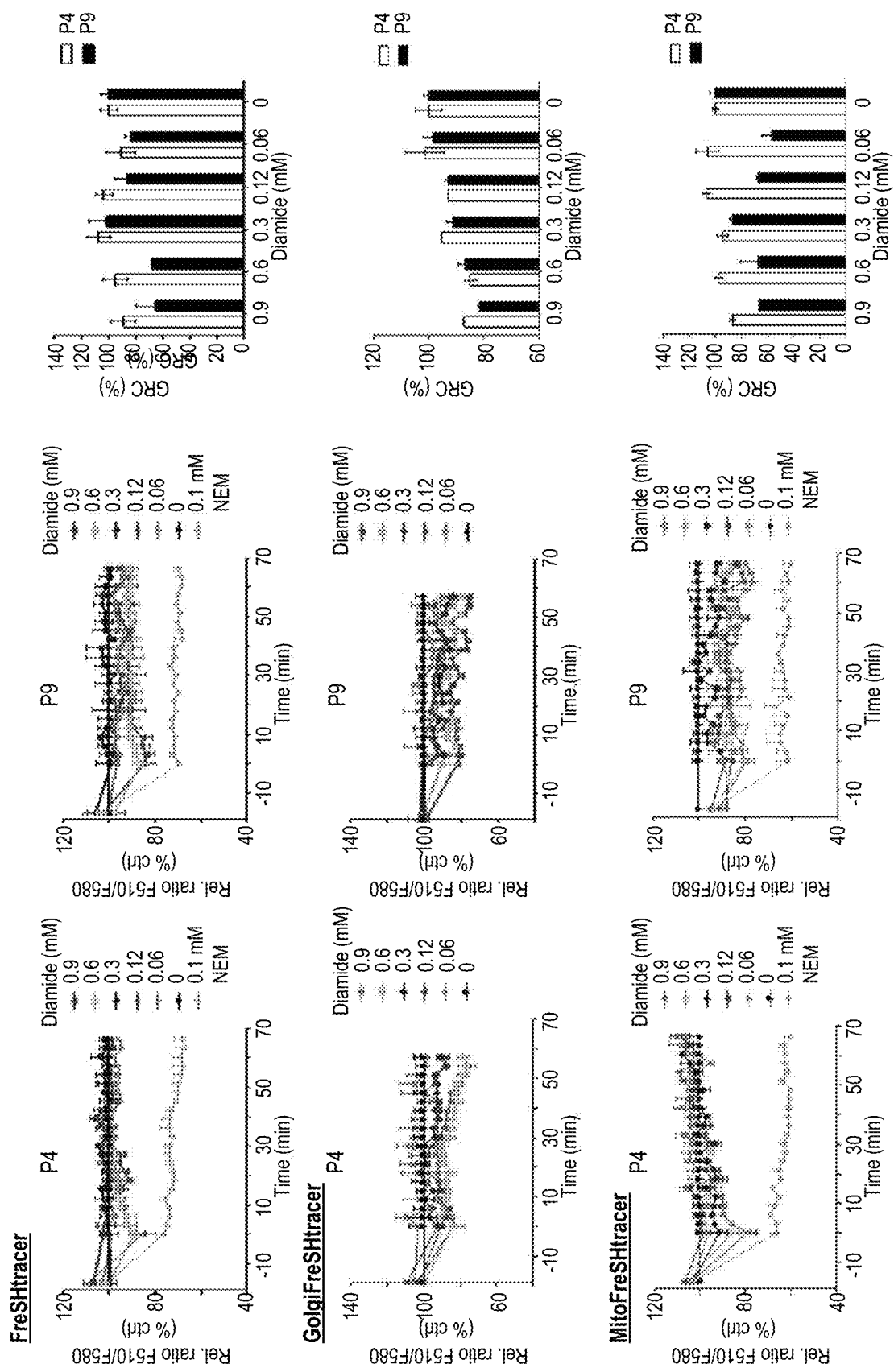
FIG. 11 illustrates results of analyzing GRC based on FreSH-Tracer, GolgiFreSH-Tracer or MitoFreSH-Tracer according to subculture of hBM-MSCs.

To confirm the relationship between the above-described glutathione evaluation parameters and the quality of stem cells, colony-forming unit-fibroblasts (CFU-F) according to the number of passages (P) of hBM-MSCs and migration capacity were analyzed. The analysis result showed that hBM-MSCs of p4.5 exhibited a considerably higher CFU-F (FIG. 9A), and a greater SDF-1α (angiogenic factor) or platelet-derived growth factor-AA (PDGF-AA)-dependent migration capacity than hBM-MSCs of p9.5 (FIG. 9B). Under these conditions, glutathione evaluation parameters of stem cells were comparatively analyzed using FreSH-Tracer for monitoring glutathione in entire cells, and the Golgi complex-specific GolgiFreSH-Tracer and mitochondria-specific MitoFreSH-Tracer (FIG. 10A). In terms of GM, as a passage number was higher, a FR mean value and a Mito-FR mean value were significantly reduced in hBM-MSCs, but there was no significant change in a Golgi-FR mean value (FIG. 10B). In terms of GH, as a passage number was higher, an FR rCV value and a Mito-FR rCV value were significantly increased in hBM-MSCs, but there was no significant change in a Golgi-FR rCV value (FIG. 10C). In terms of GRC, as a passage number was higher, FR-based % GRC and Mito-FR-based % GRC were reduced by treatment of hBM-MSCs with diamide, but there was no change in Golgi-FR-based % GRC (FIG. 11). From these results, it can be demonstrated that the quality of stem cells was proportionally related with FreSH-Tracer or MitoFreSH-Tracer-based GM and GRC, and correlated with FreSH-Tracer or MitoFreSH-Tracer-based GH in an inversely proportional manner. Particularly, it can be confirmed that the MitoFreSH-Tracer-based glutathione evaluation parameters have a higher sensitivity to stem cell quality.

Figure 12:
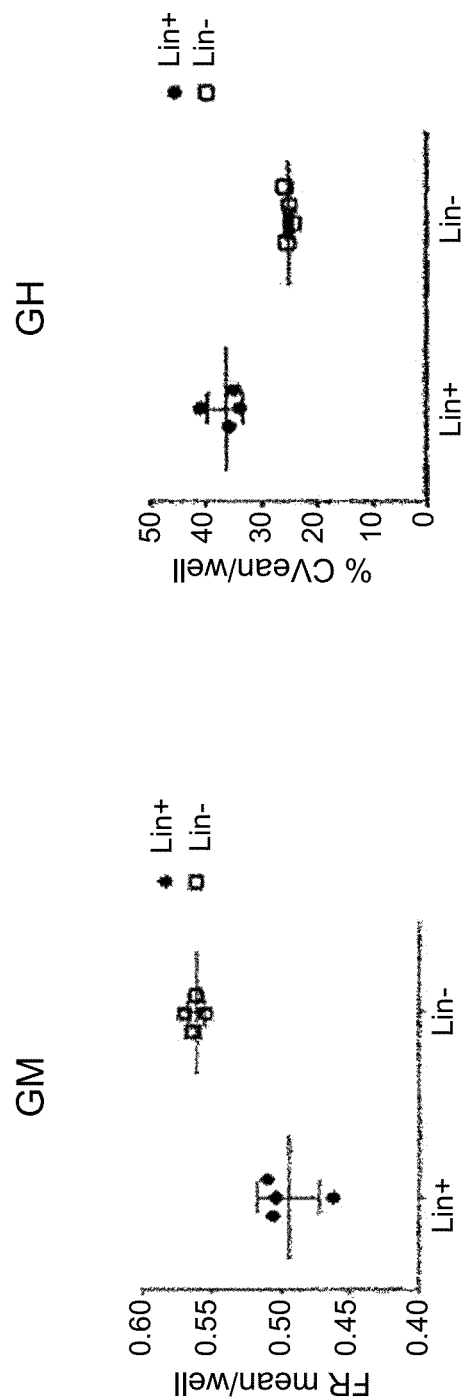
FIG. 12 illustrates results of analyzing GM and GH based on MitoFreSH-Tracer after rat bone marrow cells are isolated according to lineage.

Subsequently, the change of the MitoFreSH-Tracer-based glutathione evaluation parameters according to the degree of the differentiation of bone marrow stem cells were observed. Lineage+ cells and Lin− cells isolated from mice were stained using MitoFreSH-Tracer, and subjected to FR measurement using Operetta (PerkinElmer), and MitoFreSH-Tracer-based glutathione evaluation parameters were confirmed per cell population. As a result, it was confirmed that, compared with differentiated Lineage+ cells, in undifferentiated Lin− cells, mitochondrial GM is high and GH is low (FIG. 12). This means that the stemness of bone marrow cells can be distinguished as a glutathione evaluation parameter.

Figure 13A:
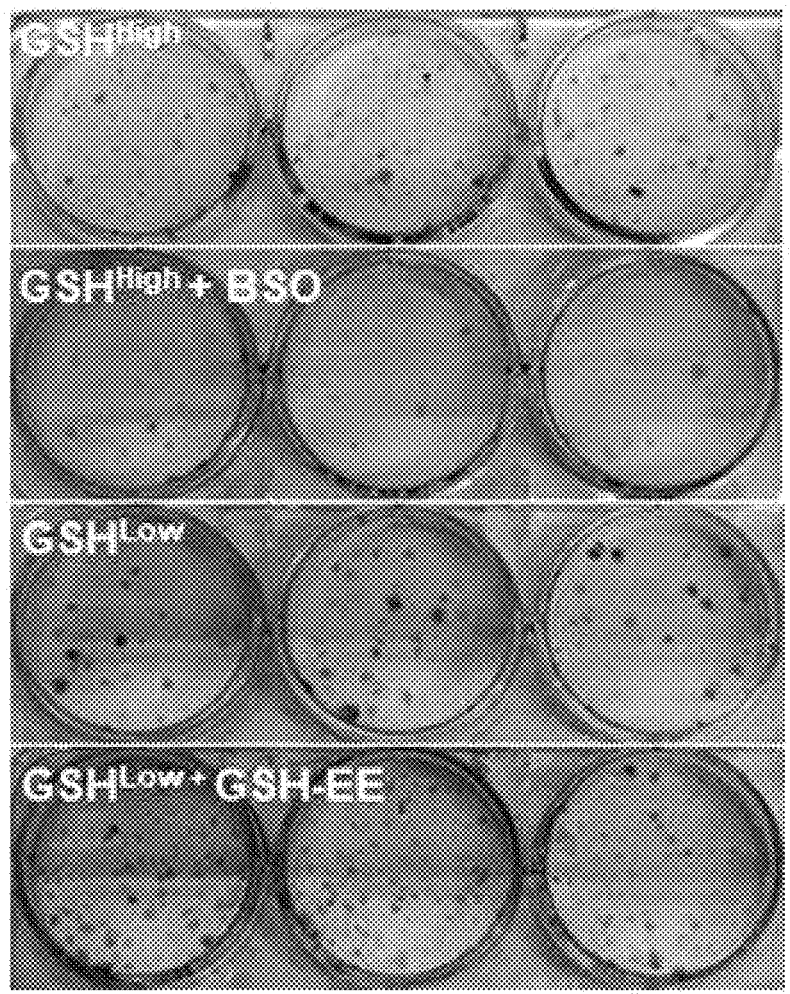
FIG. 13 illustrates results of analyzing CFU-F (FIG. 13A) or a cell migration capacity by PDGF-AA (FIG. 13B) after hES-MSCs sorted by FACS using FreSH-Tracer (FIG. 13A) or hES-MSCs cultured without sorting (FIG. 13B) are treated with BSO or GSH-EE.
Figure 13B:

Example 5: Detection of Material for Enhancing Quality of Cell Therapeutic Agent Using FreSH-Tracer In order to test whether direct control of a GSH level in stem cells leads to changes in cell functions, hES-MSCs sorted by FreSH-Tracer were treated with buthionine sulfoximine (BSO; glutathione synthesis inhibitor) and glutathione ethyl ester (GSH-EE). When GSH was decreased in cells by treating $GSH^{High}$ cells with BSO (80 μM, 24 h), it was confirmed that CFU-F increased, and on the other hand, when GSH was increased by treating $GSH^{Low}$ cells with GSH-EE (1 mM, 2 h), it was confirmed that CFU-F decreased (FIG. 13A). In addition, it was confirmed that, when hES-MSCs which were not sorted by FreSH-Tracer were treated with BSO or GSH-EE, PDGF-AA-induced cell migration capacity was decreased or increased, respectively (FIG. 13B).

Figure 14A:
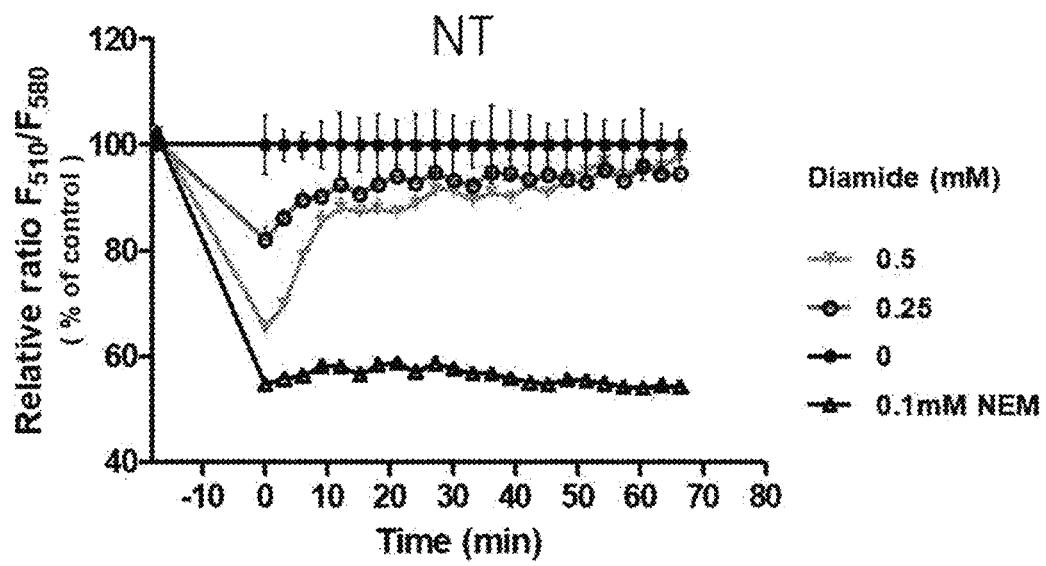
FIGS. 14A to 14C illustrate results of analyzing GRC based on FreSH-Tracer after hUC-MSCs are subcultured three times in a culture medium containing AA2G.
Figure 14B:
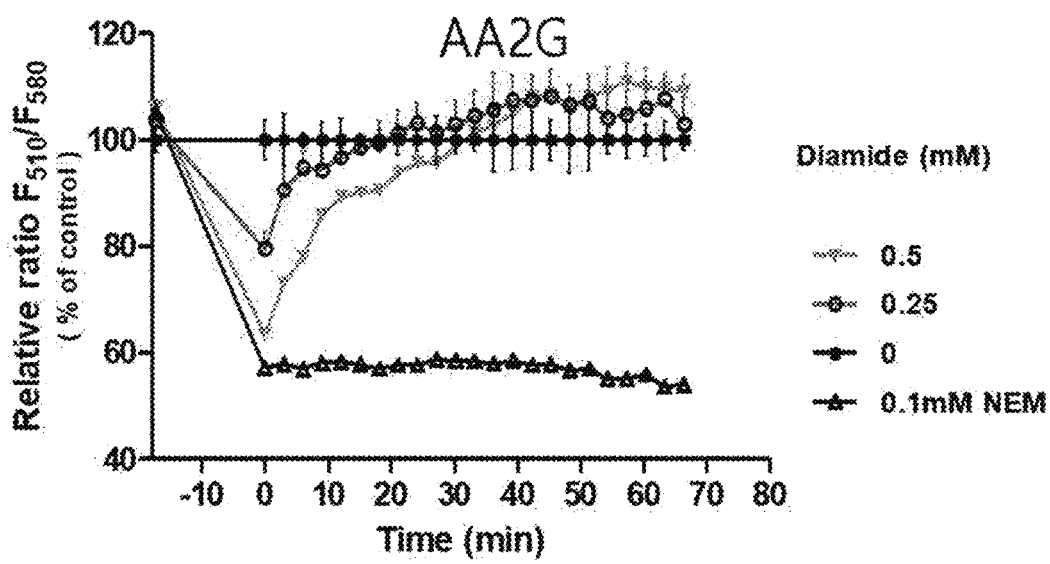
Figure 14C:
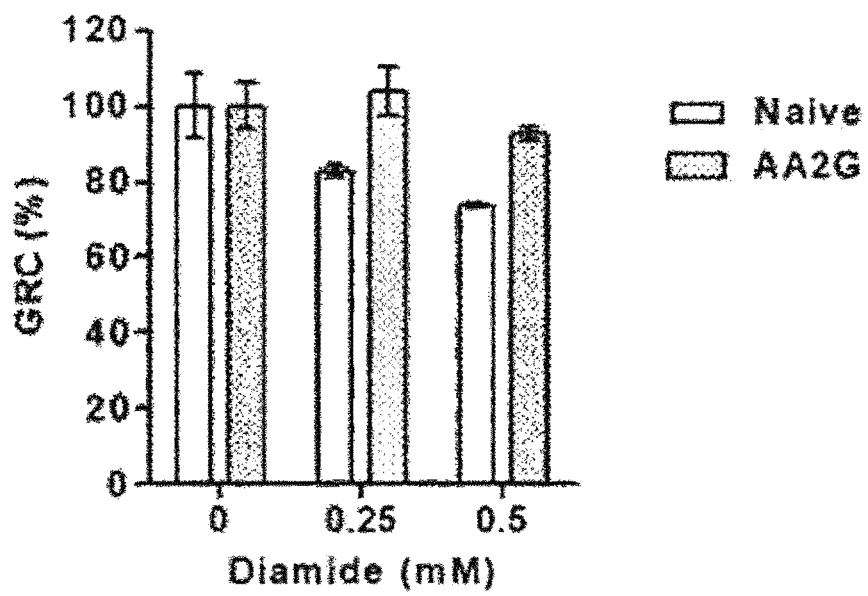

Meanwhile, when hUC-MSCs were subcultured three times in medium containing the antioxidant ascorbic acid 2-glucoside (AA2G, 250 μg/mL), compared with a naive cell group, it was confirmed that FreSH-Tracer-based GRC was increased by treatment with a low concentration of diamide (FIG. 14). Therefore, it was demonstrated that a material for enhancing a glutathione evaluation parameter improves cell functions.

Figure 15A:
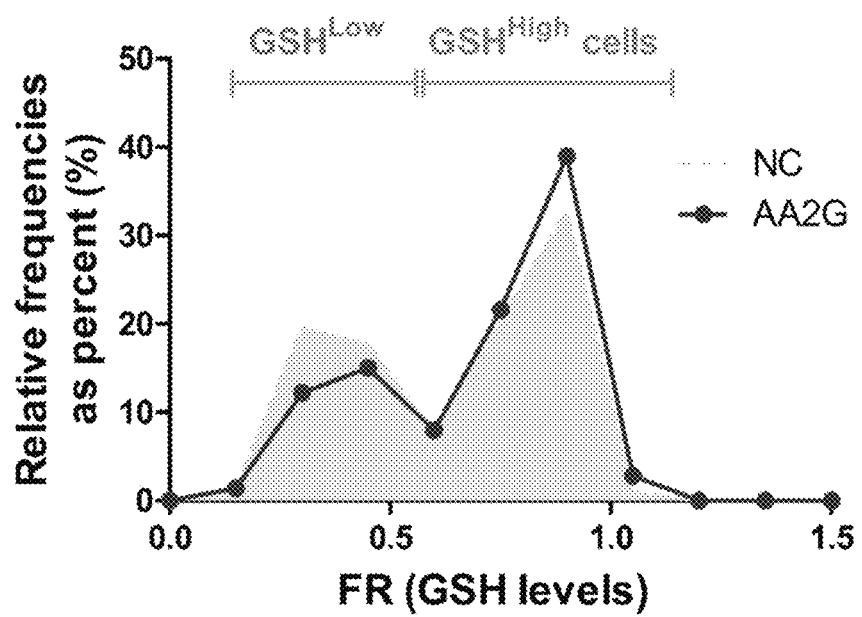
FIGS. 15A and 15B illustrate results of analyzing ORC based on FreSH-Tracer after hUC-MSCs are subcultured three times in a culture medium containing AA2G.
Figure 15B:
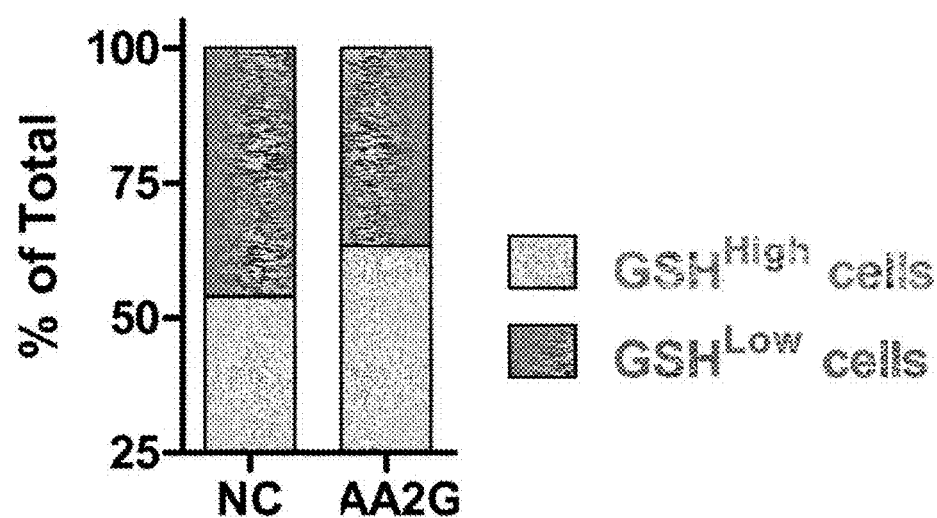

In addition, when hUC-MSCs were subcultured three times in the AA2G (250 μg/mL)-containing medium, compared with the naive cell group (NC), it was confirmed that the FreSH-Tracer-based ORC was higher in $GSH^{High}$ cells (FIGS. 15A and 15B).

Figure 16A:
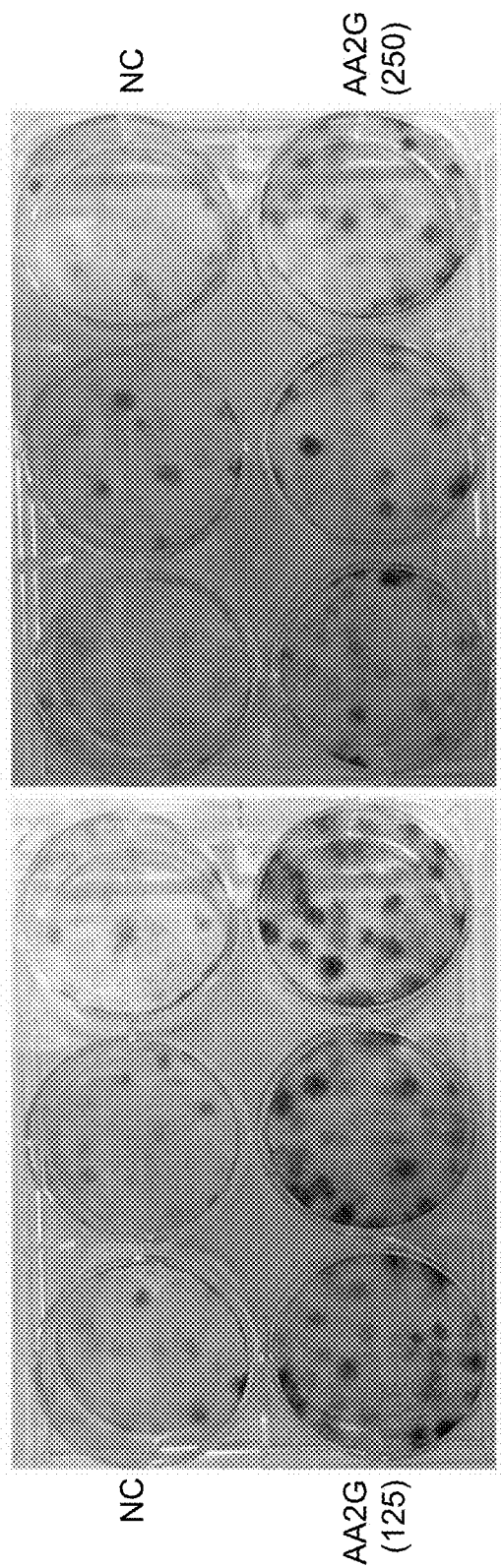
FIG. 16A is image showing the result of a CFU-F assay after hUC-MSCs are treated with 125 μg/mL of AA2G (left image) or 250 μg/mL of AA2G (right image) for three days.
Figure 16B:
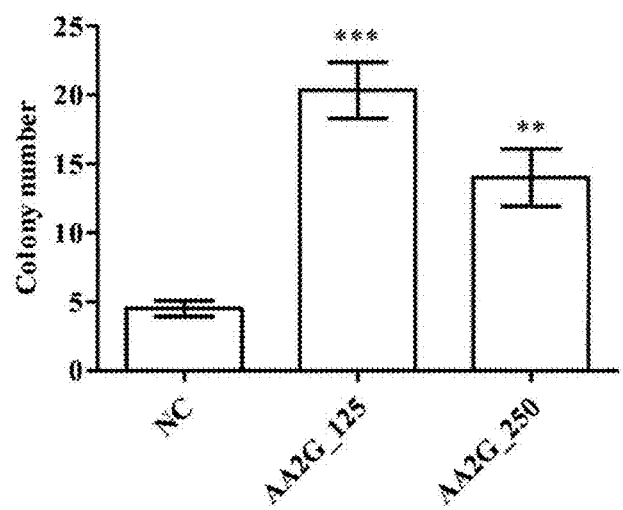
FIG. 16B is a graph showing the result of a CFU-F assay (n=3) after hUC-MSCs are treated with 125 or 250 μg/mL of AA2G for three days.
Figure 17A:
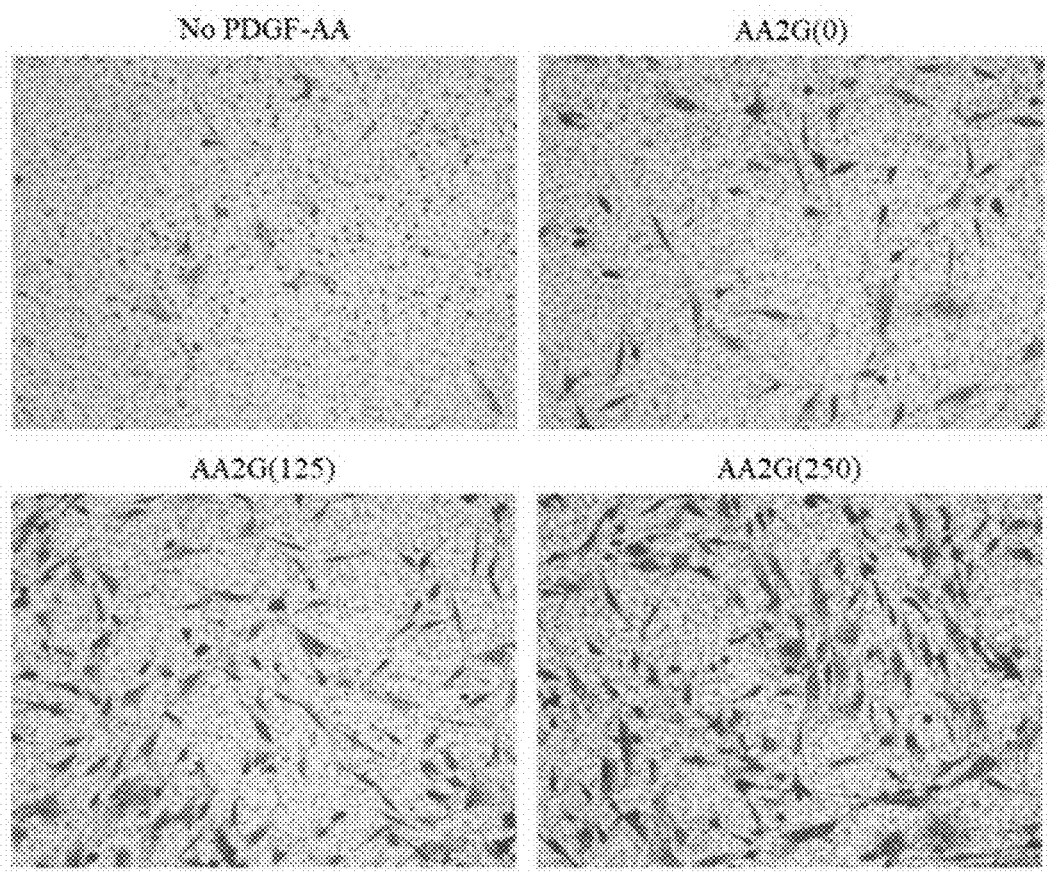
FIG. 17A illustrates images showing migration capacity by PDGF-AA after hUC-MSCs are treated with 125 or 250 μg/mL of AA2G for three days.
Figure 17B:
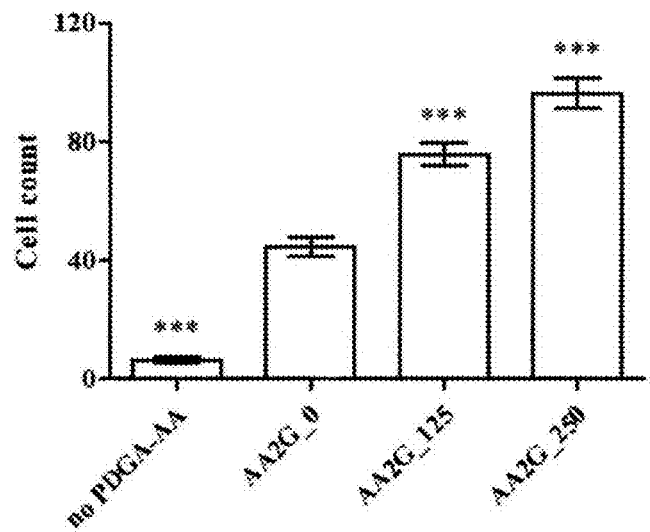
FIG. 17B illustrates a graph showing a result of analyzing migration capacity (n=3) by PDGF-AA after hUC-MSCs are treated with 125 or 250 μg/mL of AA2G for three days.

The inventors observed an effect of the material on stem cells by treating each stem cells with a material for enhancing a glutathione evaluation parameter. When hUC-MSCs were subcultured in a L-AA2G-containing medium, CFU-F, migration capacity, and an anti-inflammatory effect were observed. A CFU-F assay (n=3) was performed by treating hUC-MSCs with 125 or 250 μg/mL of AA2G for three days. As shown in FIGS. 16A and 16B, it was confirmed that, when AA2G was treated, CFU-F increased. In addition, as hUC-MSCs were treated with 125 or 250 μg/mL of AA2G for three days, PDGF-AA-induced migration capacity (n=3) was analyzed. As shown in FIGS. 17A and 17B, it was confirmed that the migration capacity was increased by AA2G treatment. In addition, the reduction in T cell proliferation, a reduction in T cell differentiation, and the promotion of Treg cell differentiation were observed by treating hUC-MSCs with 125 or 250 μg/mL of AA2G for three days.

Figure 18A:
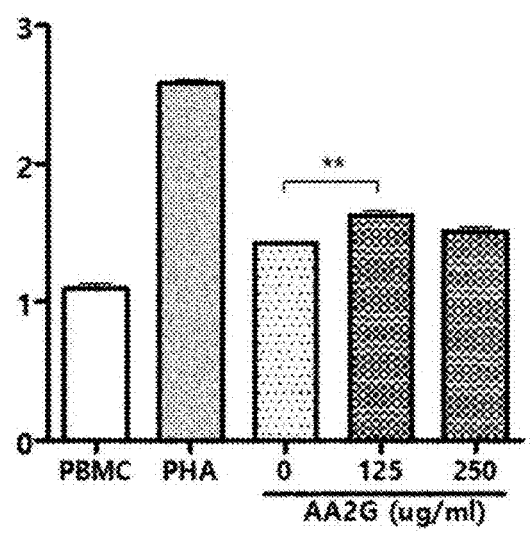
FIG. 18A illustrates a graph showing an effect of reducing the proliferation capacity (n=3) of T cells after hUC-MSCs are treated with 125 or 250 μg/mL of AA2G for three days.
Figure 18B:
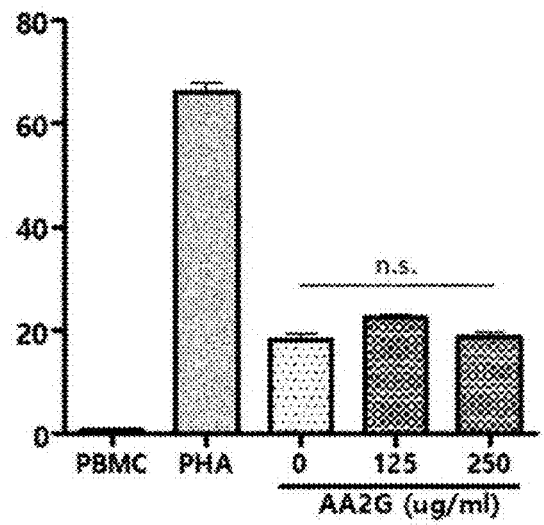
FIG. 18B illustrates a graph showing an effect of reducing the differentiation capacity (n=3) of T cells after hUC-MSCs are treated with 125 or 250 μg/mL of AA2G for three days.
Figure 18C:
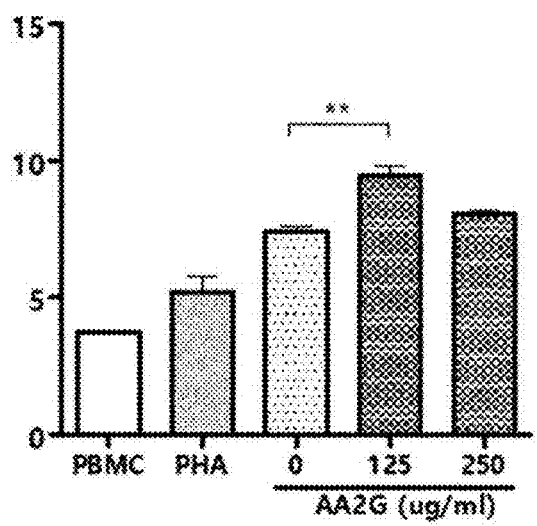
FIG. 18C illustrates a graph showing an effect of promoting the differentiation (n=3) of Treg cells after hUC-MSCs are treated with 125 or 250 μg/mL of AA2G for three days.

As shown in FIGS. 18A to 18C, it was confirmed that an anti-inflammatory effect of stem cells was exhibited by treating AA2G.

Figure 19:
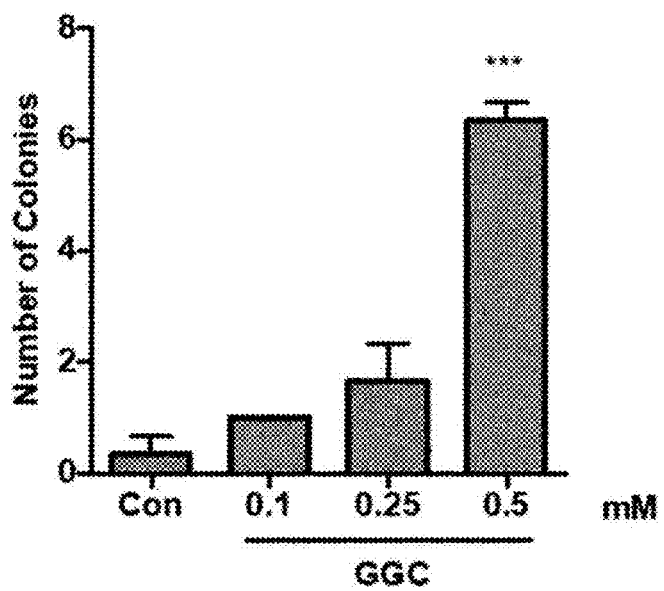
FIG. 19 illustrates a graph showing a result of CFU-F assay (n=3) after hUC-MSCs are treated with 0.1, 0.25 and 0.5 mM γ-glutamyl cysteine (GGC) for 2 hours.
Figure 20A:
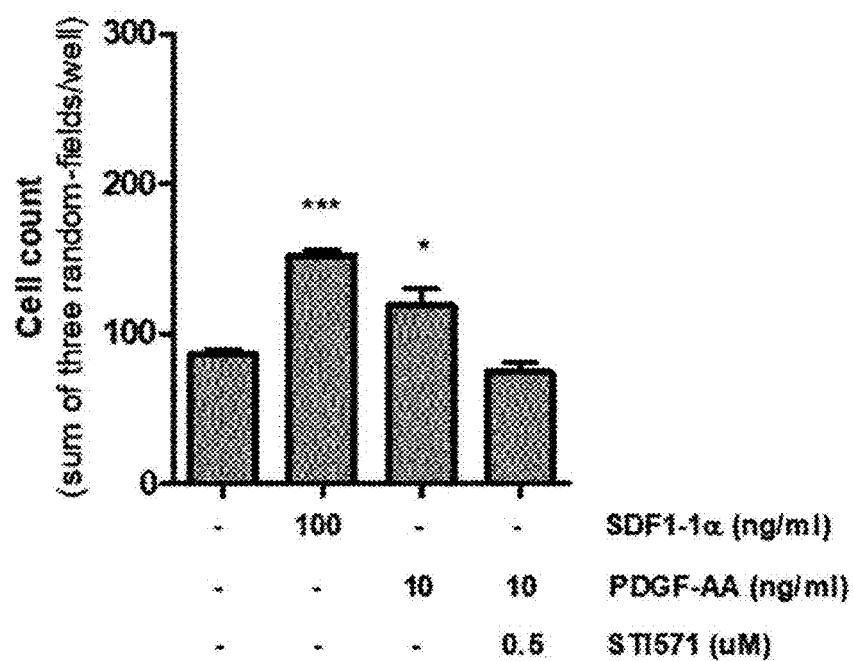
FIG. 20A is a graph showing a result of analyzing migration capacity (n=3) by SDF1α and PDGF-AA without treatment of hUC-MSCs with GGC. STI571 is used as a PDGFR kinase inhibitor.
Figure 20B:
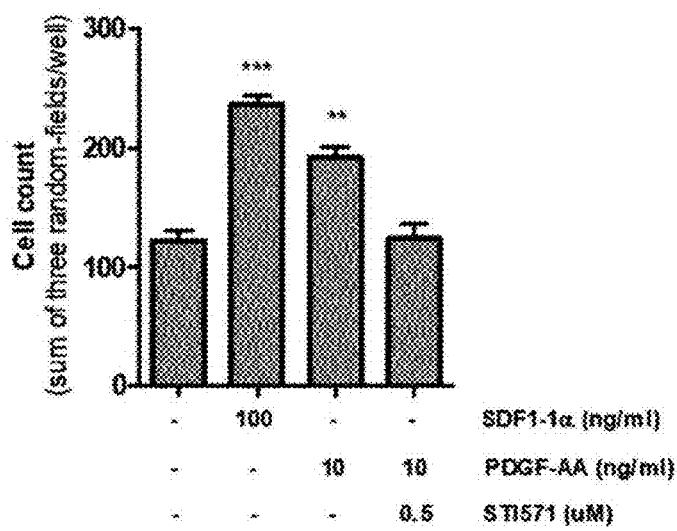
FIG. 20B is a graph showing a result of analyzing migration capacity (n=3) by SDF1α and PDGF-AA after hUC-MSCs are treated with 0.1 mM GGC. STI571 is used as a PDGFR kinase inhibitor.
Figure 20C:
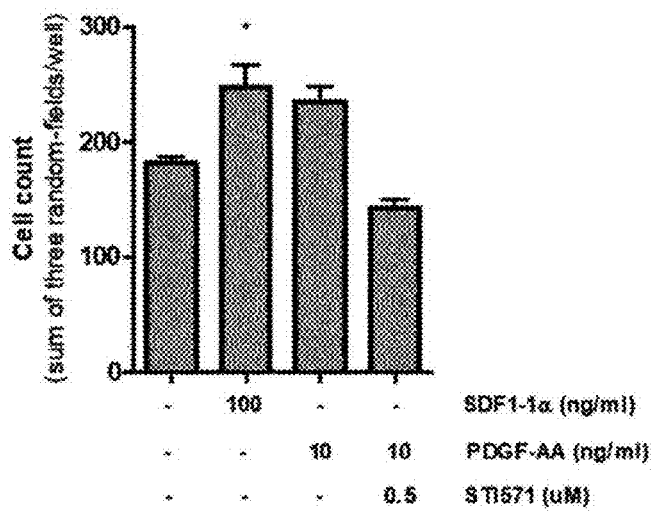
FIG. 20C is a graph showing a result of analyzing migration capacity (n=3) by SDF1α and PDGF-AA after hUC-MSCs are treated with 0.25 mM GGC. STI571 is used as a PDGFR kinase inhibitor.

Meanwhile, hUC-MSCs were cultured with a glutathione precursor such as γ-glutamyl cysteine (GGC, 0.1, 0.25, and 0.5 mM). A CFU-F assay (n=3) was performed by treating hUC-MSCs with each concentration of GGC for 2 hours. As a result, as shown in FIG. 19, it was confirmed that CFU-F increased. In addition, SDF1α and PDGF-AA-induced migration capacities (n=3) were analyzed for hUC-MSCs without treatment with GGC, and SDF1α- and PDGF-AA-induced migration abilities (n=3) were analyzed by treating hUC-MSCs with the increasing concentrations of GGC. STI571 was used as a PDGFR kinase inhibitor. As shown in FIGS. 20A to 20C, it was confirmed that, according to an increase in GGC treatment concentration, SDF1α- and PDGF-AA-induced migration capacities were enhanced.

Figure 21:
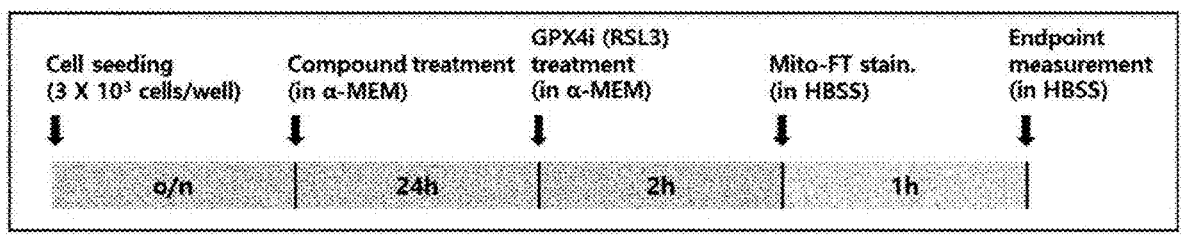
FIG. 21 is a diagram illustrating procedures of an experiment of screening for a material for regulating GSH of cells through GM, GH, and ORC analyses.

In addition, for ORC analysis, as shown in FIG. 21, living cells were prepared, and 3×10$^3$ of the cells were seeded in each well. 10% fetal bovine serum, and 1× penicillin-streptomycin were added to an α-MEM medium. A material for improving a glutathione evaluation parameter was treated. Subsequently, a glutathione peroxidase 4 (GPX4) inhibitor, RSL3, was treated. After 2-hour culture, a RSL3-containing medium was removed, 15 μM MitoFreSH-Tracer was added per 100 μl, followed by culturing at 37° C. for 1 hour. The medium used in the culture was 10 mM HEPES-containing HBSS.

Figure 22A:
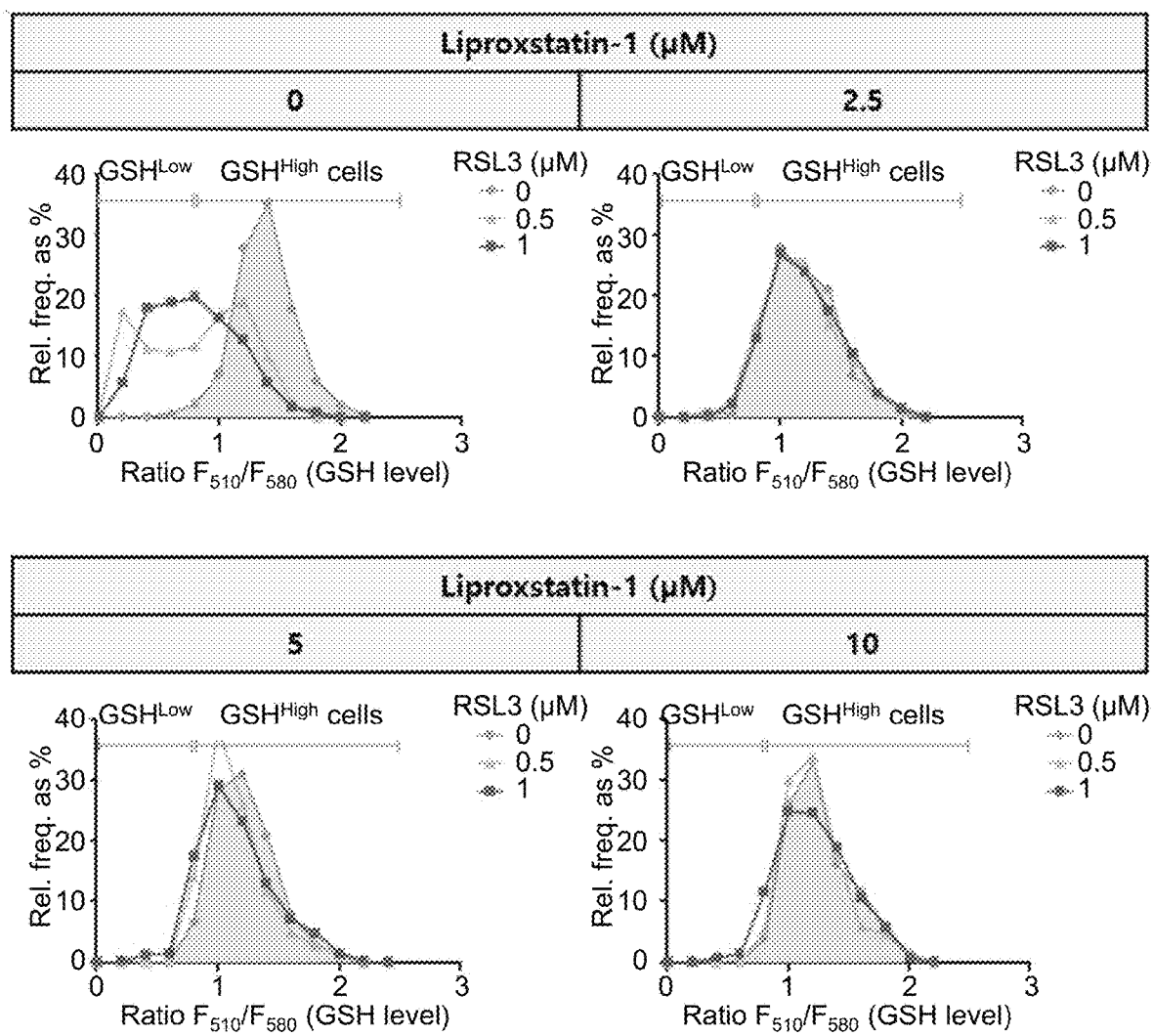
FIGS. 22A and 22B illustrate results of analyzing ORC of liproxstatin-1 in hUC-MSCs.
Figure 22B:
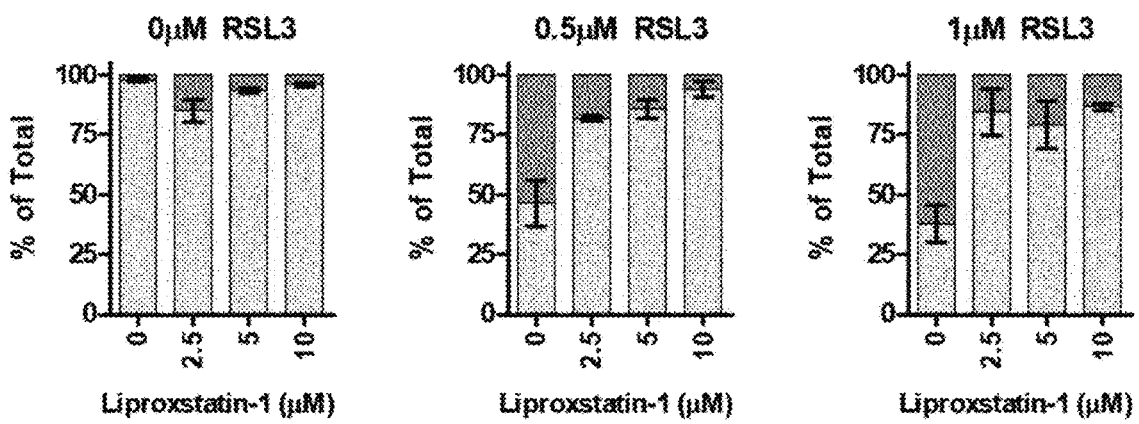
Figure 23A:
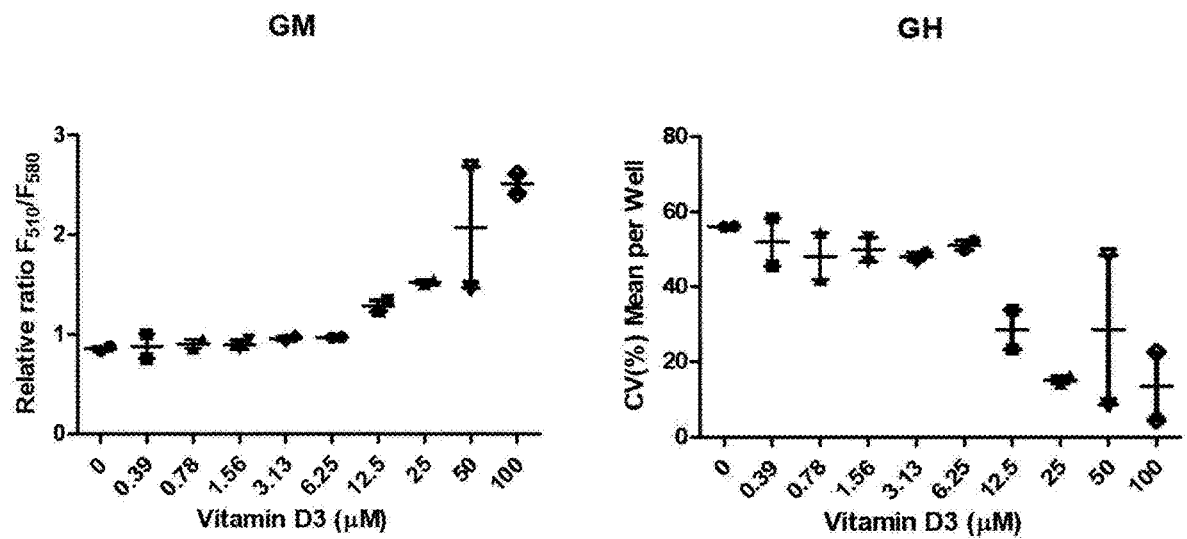
FIGS. 23A to 23C illustrate results of analyzing GM, GH and ORC of vitamin D3 in hUC-MSCs.
Figure 23B:
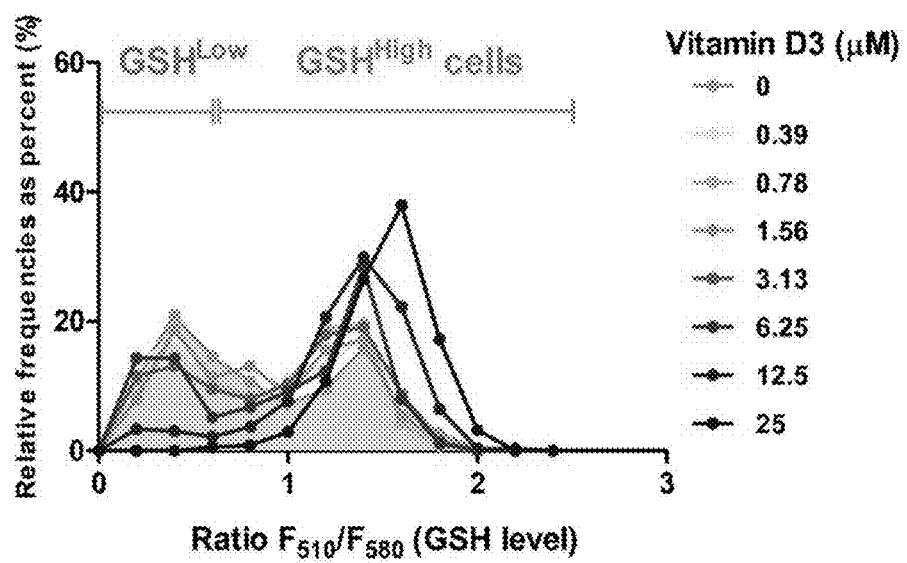
Figure 23C:
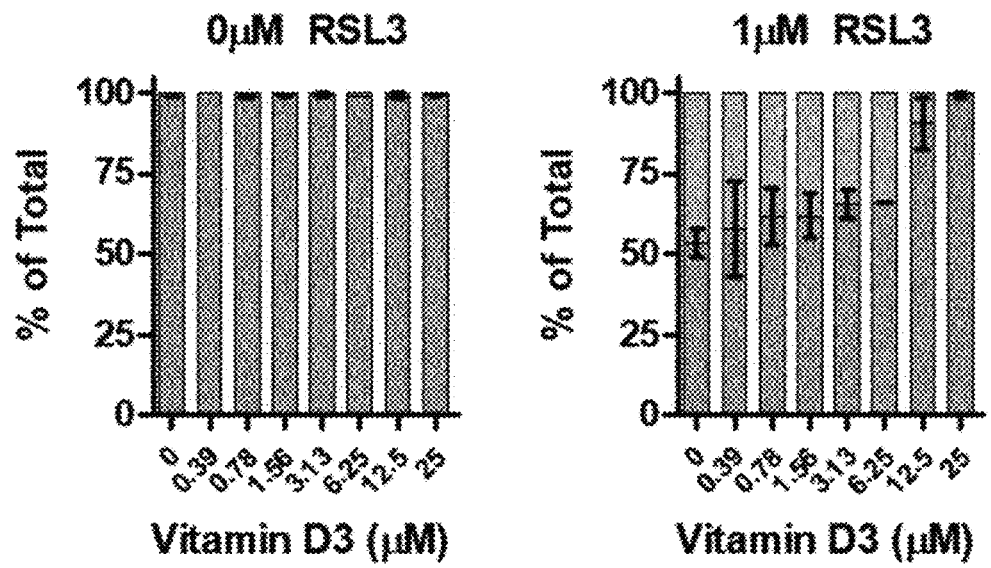
Figure 24:
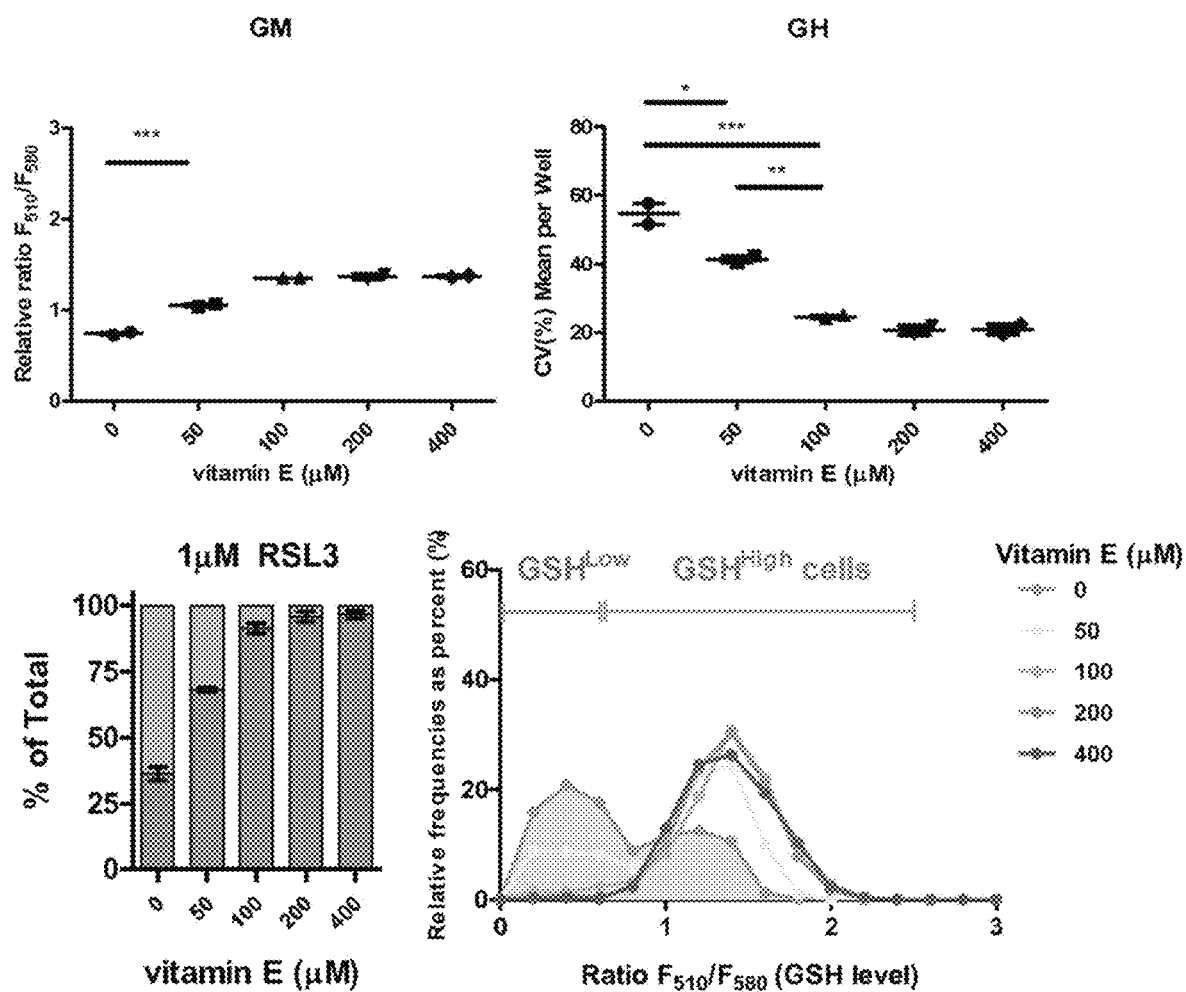
FIG. 24 illustrates results of analyzing GM, GH and ORC of vitamin E in hUC-MSCs.
Figure 25A:
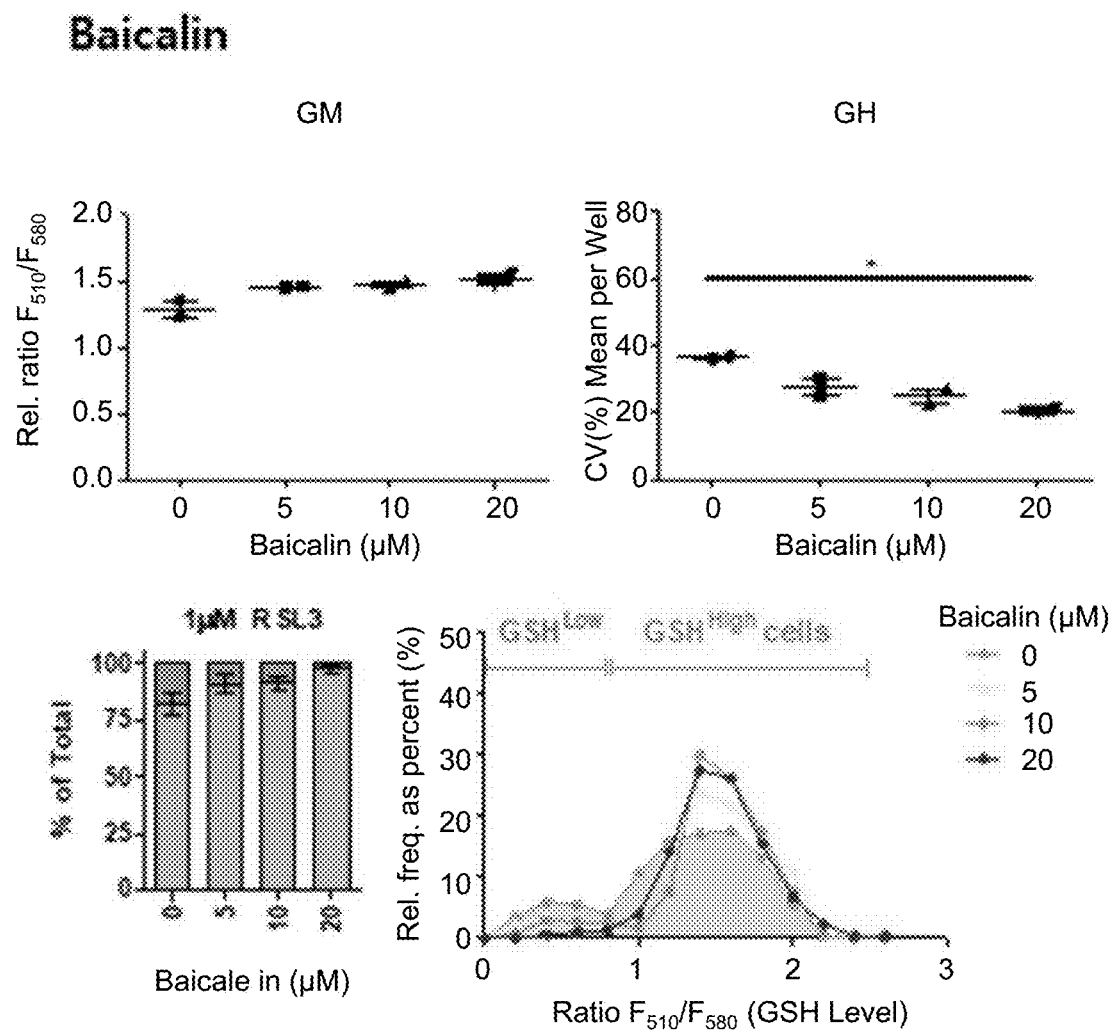
FIGS. 25A to 25E illustrate results of analyzing GM, GH and ORC of a flavonoid in hUC-MSCs, where
Figure 25B:
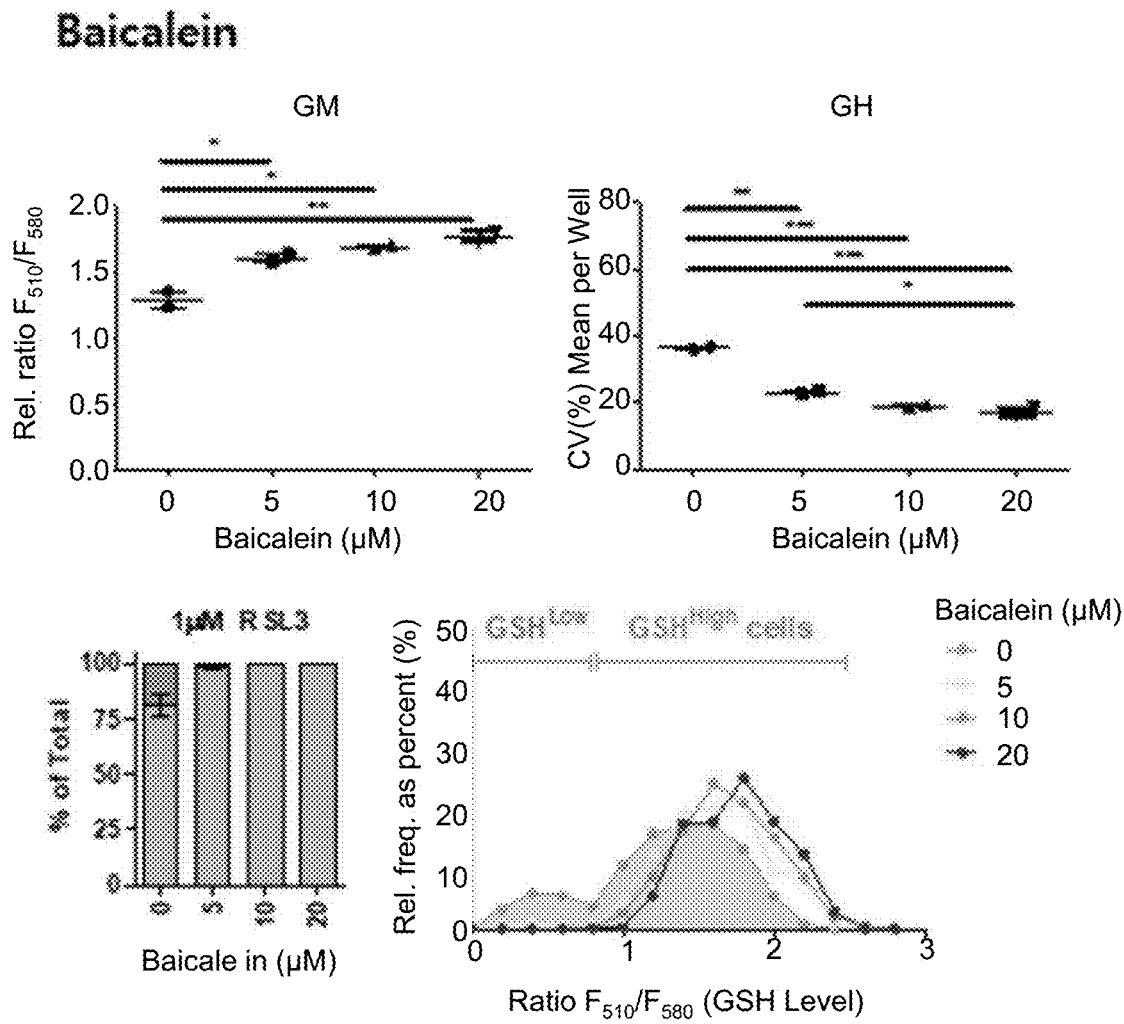
Figure 25C:
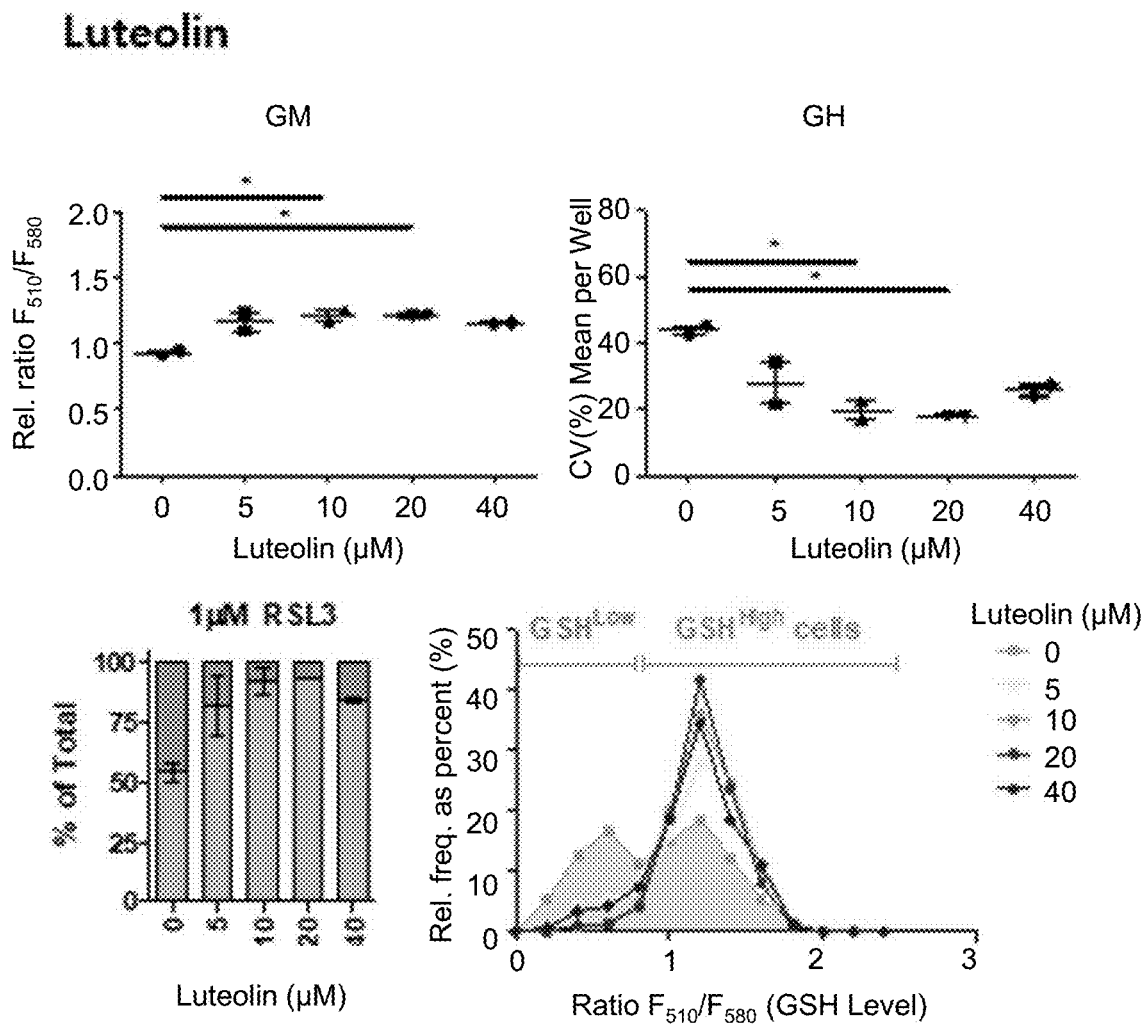
Figure 25D:
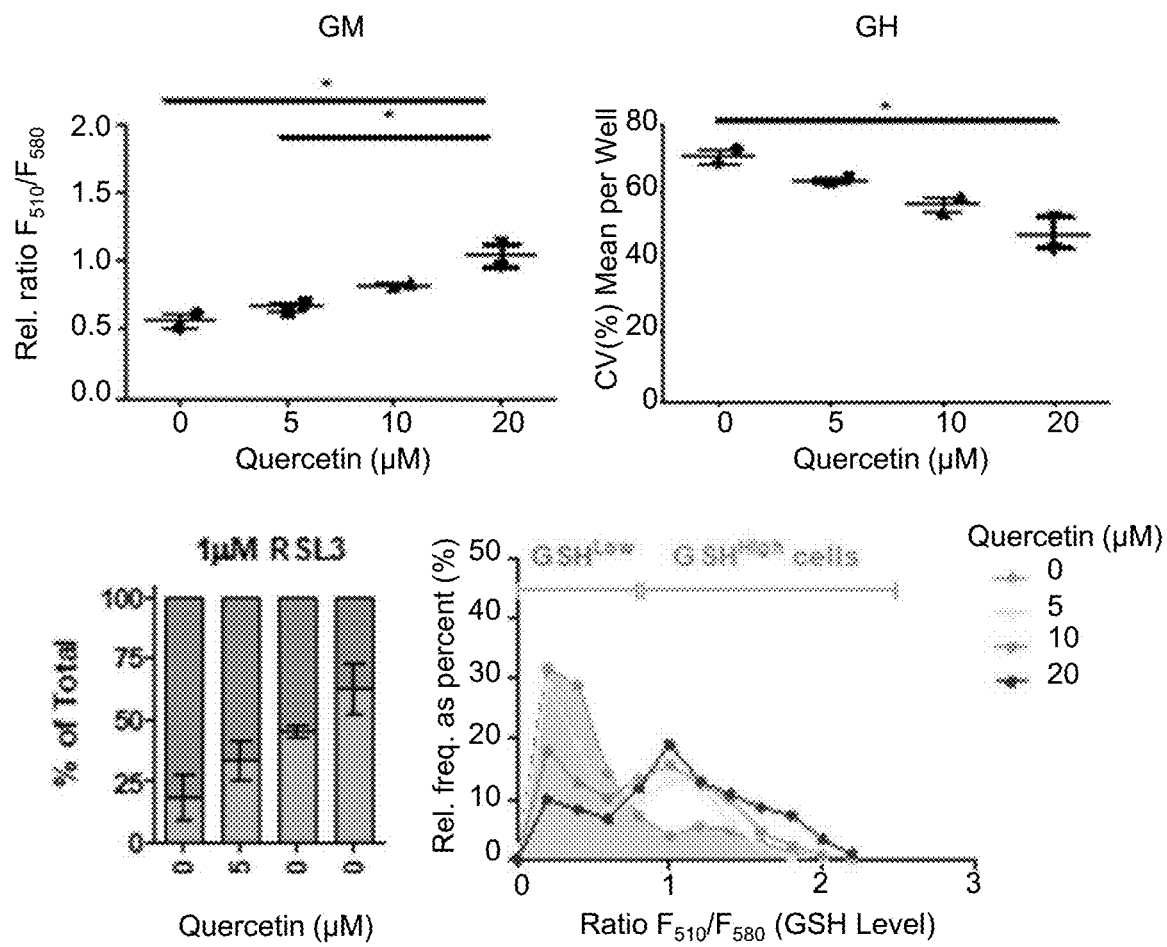
Figure 25E:
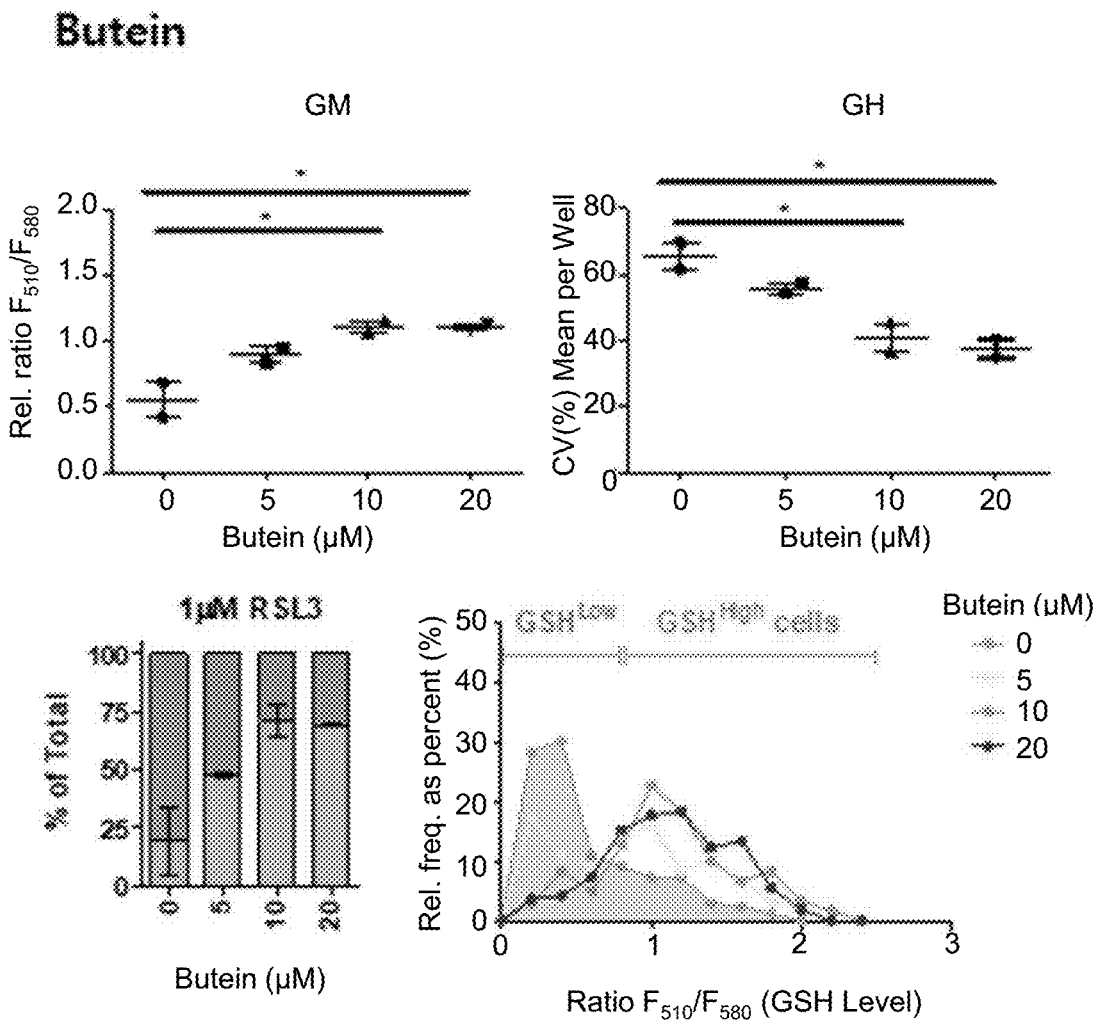
Figure 26A:
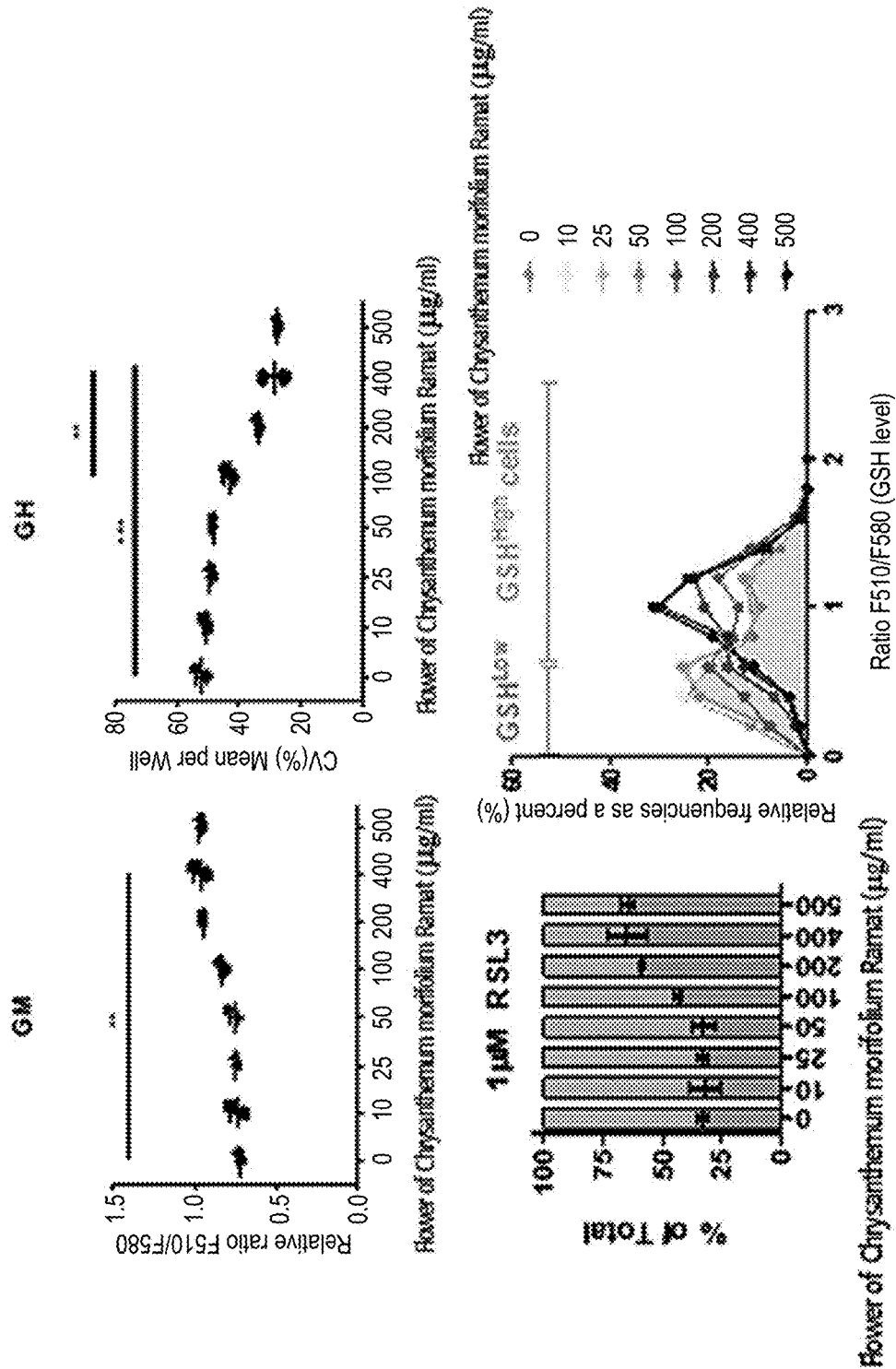
FIGS. 26A to 26F illustrate results of analyzing GM, GH and ORC of plant extracts in hUC-MSCs, where
Figure 26B:
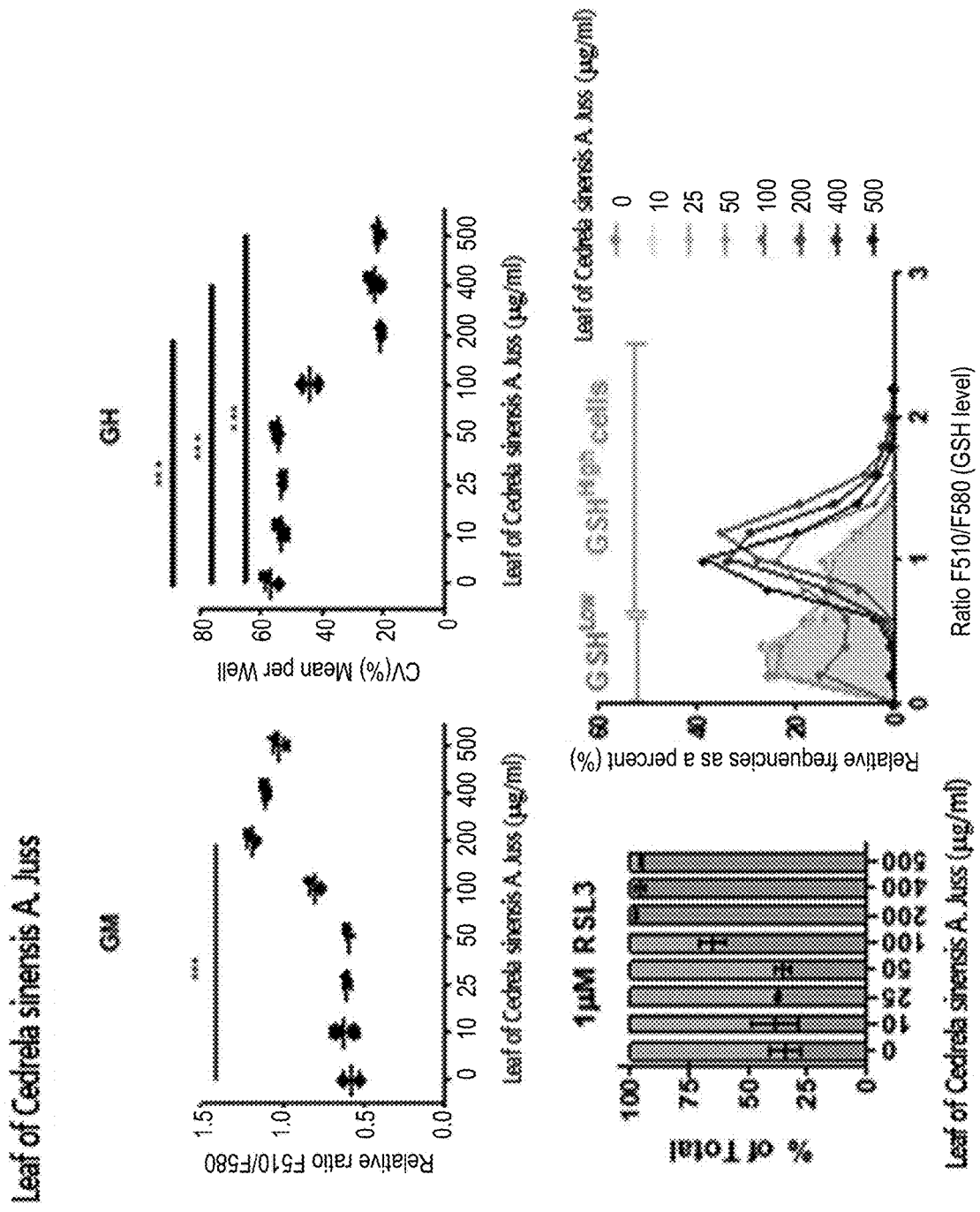
Figure 26C:
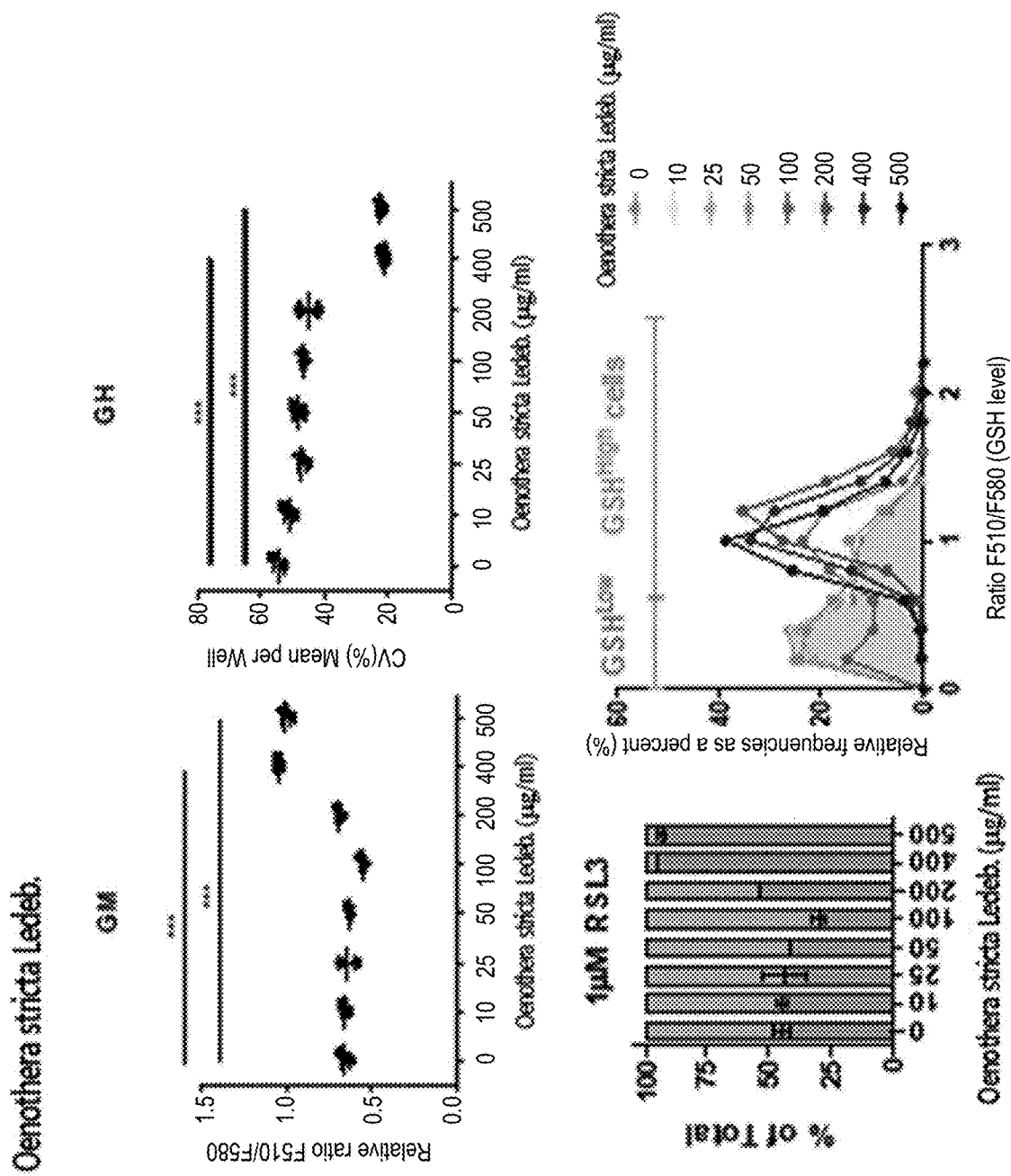
Figure 26D:
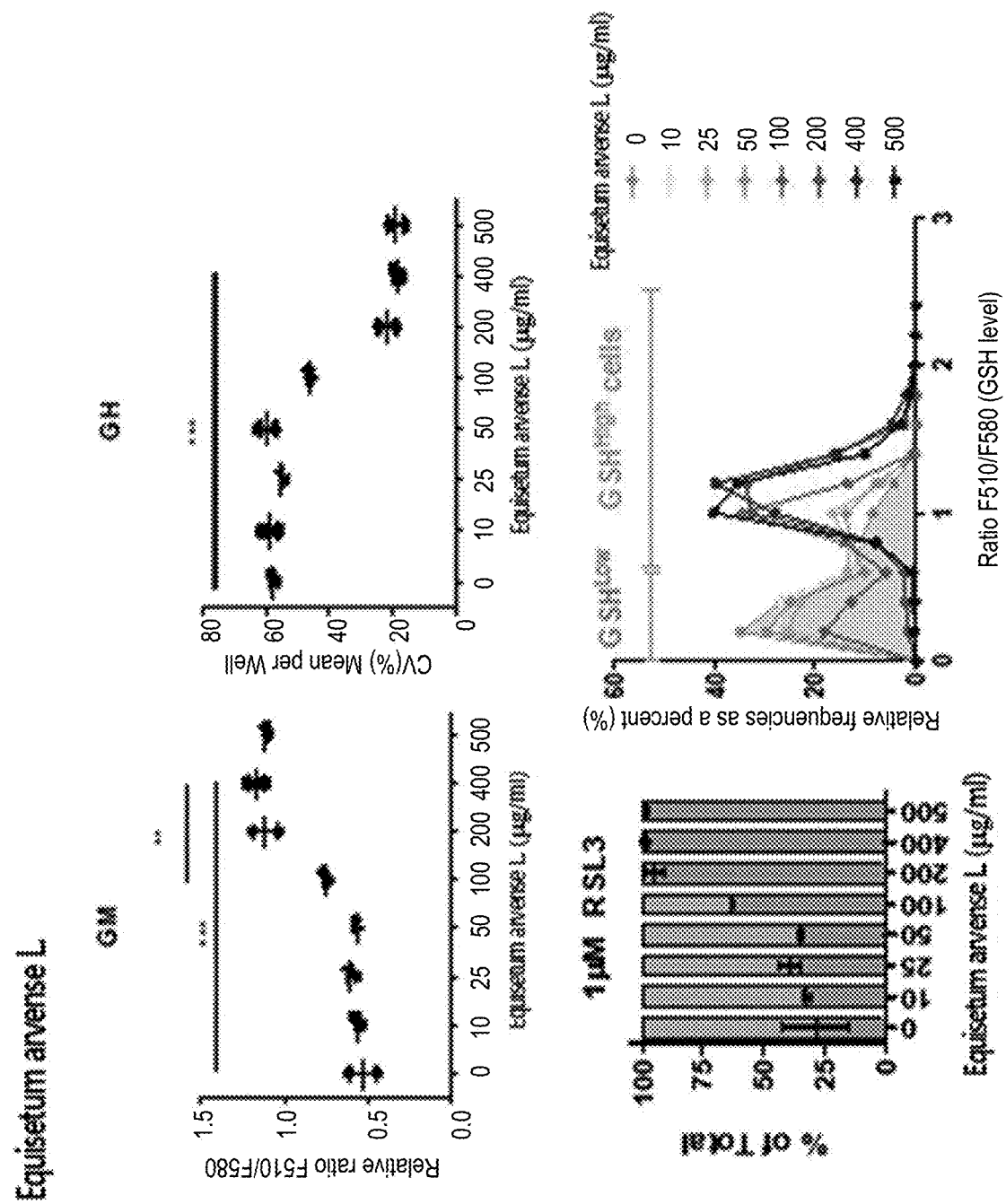
Figure 26E:
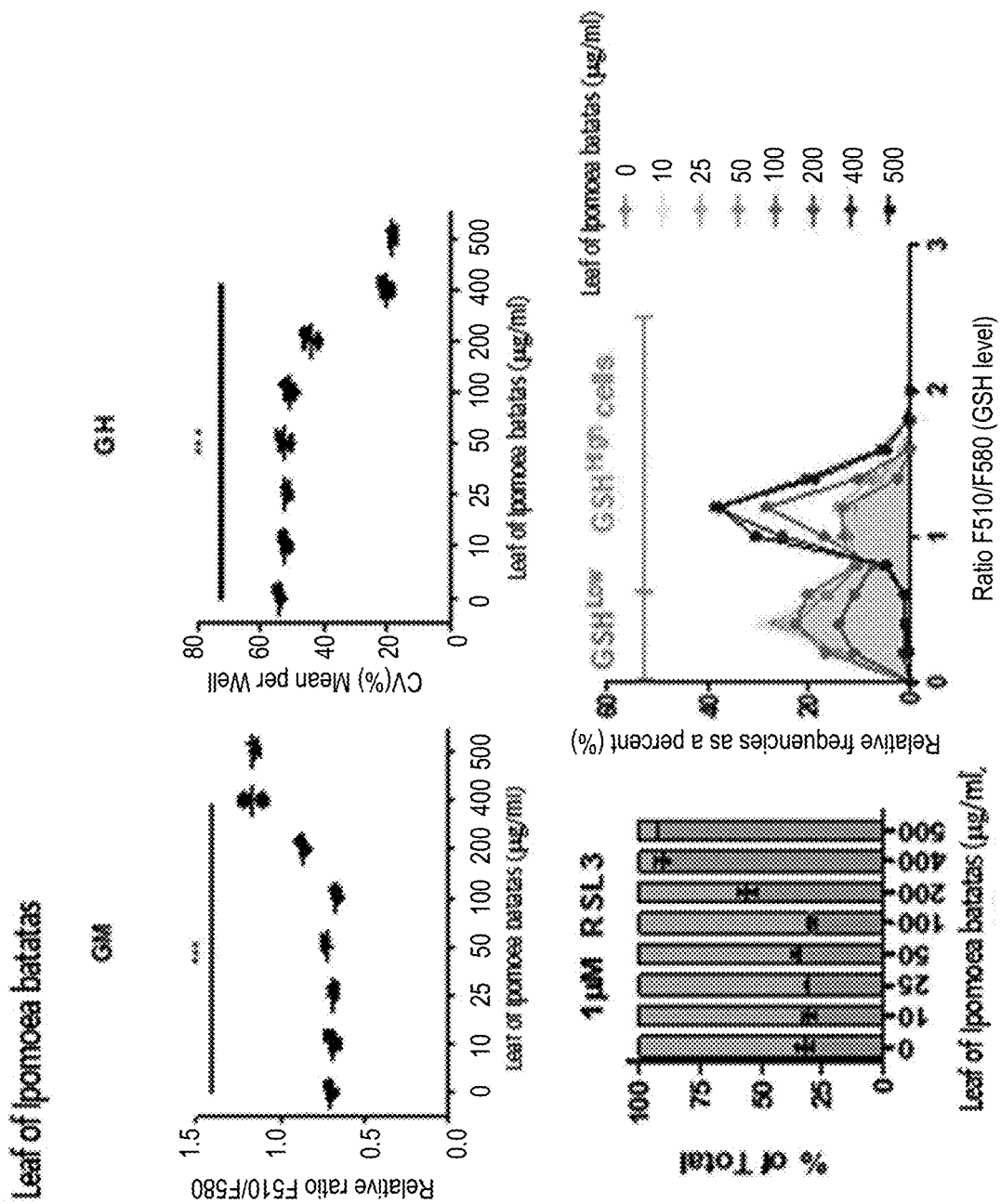
Figure 26F:
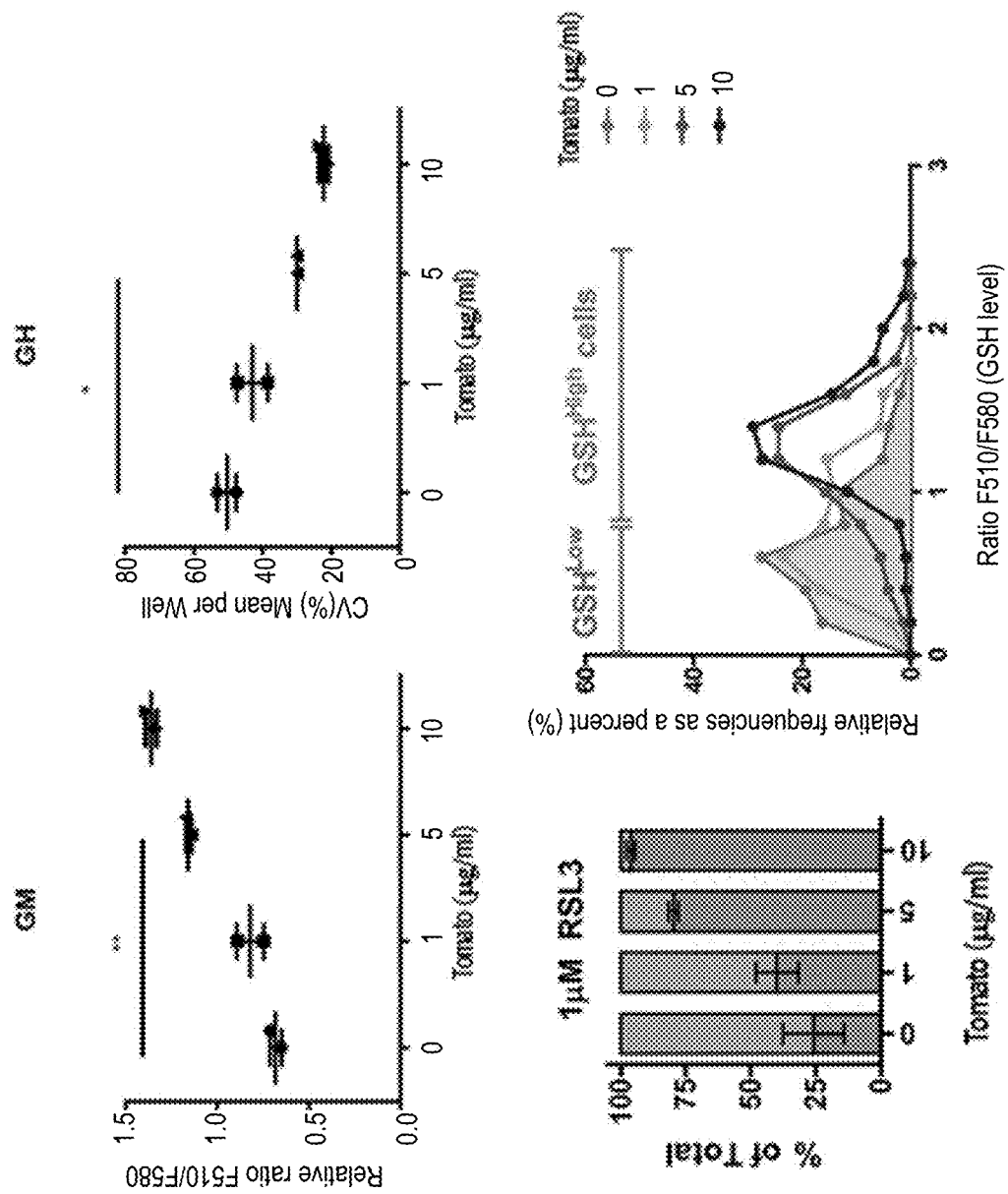

The inventors analyzed ORC by treating hUC-MSCs with a material for improving a glutathione evaluation parameter, such as liproxstatin-1, vitamin D3, vitamin E, flavonoid-type baicalin, baicalein, luteolin, quercetin, butein, or a plant extract such as a flower extract of *Chrysanthemum morifolium* Ramat, a leaf extract of *Cedela sinensis* A. Juss, an extract of *Oenothera stricta* Ledeb., an extract of *Equisetum arvense* L., a leaf extract of *Ipomoea batatas* or a tomato extract (LYCOBEADS®) (see FIGS. 22A to 26F). For example, as shown in FIG. 22A, 0, 2.5, 5 or 10 μM liproxstatin-1 was treated, and 0, 0.5 or 1 μM RSL3 was also treated. It was observed that, even if the quality of the cells is degraded by RSL3, the higher the concentration of liproxstatin-1, the higher the quality of cells. That is, it was confirmed that a ratio of the GSH$^{High}$ cells was increased.

A CFU-F assay (n=3) was performed by treating hUC-MSCs with 0.2, 1, 2, and 4 μM ferrostatin-1 and 0.1, 0.5, 1, and 2 μM liproxstatin-1 for 24 hours. As shown in FIGS. 27, and 28A to 28C, there was no change in anti-inflammatory effect with GGC treatment.

Figure 27:
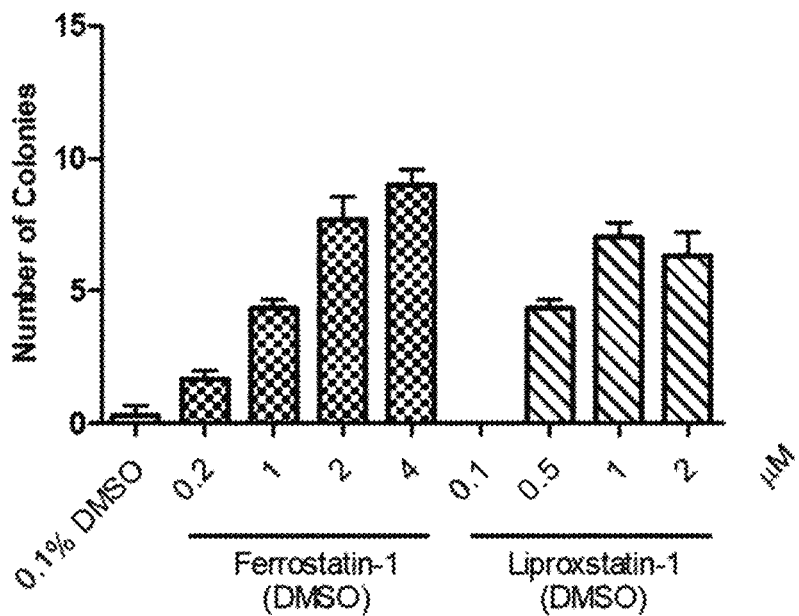
FIG. 27 is a graph showing a result of CFU-F assay (n=3) after hUC-MSCs are treated with 0.2, 1, 2 and 4 μM ferrostatin-1 and 0.1, 0.5, 1 and 2 μM liproxstatin-1 for 24 hours.
Figure 28A:
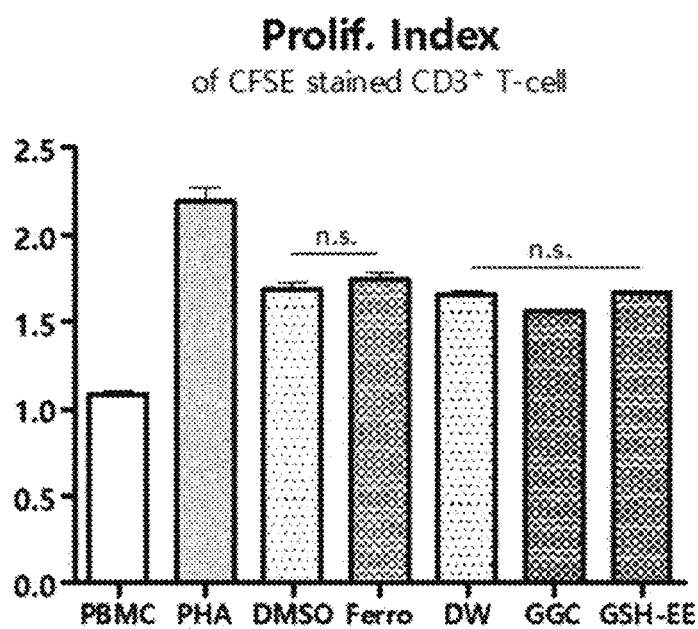
FIG. 28A is a graph showing an effect of reducing the proliferation capacity (n=3) of T cells after hUC-MSCs are treated with 1 μM ferrostatin-1 for 24 hours, or treated with 0.2 mM GGC or 2 mM GSH-EE for 2 hours.
Figure 28B:
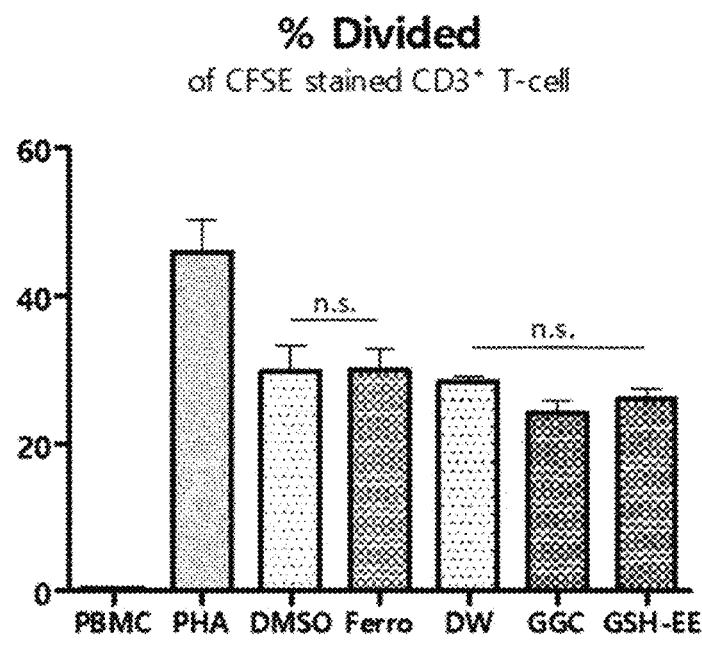
FIG. 28B is a graph showing an effect of reducing the differentiation capacity (n=3) of T cells after hUC-MSCs are treated with 1 μM ferrostatin-1 for 24 hours, or treated with 0.2 mM GGC or 2 mM GSH-EE for 2 hours.
Figure 28C:
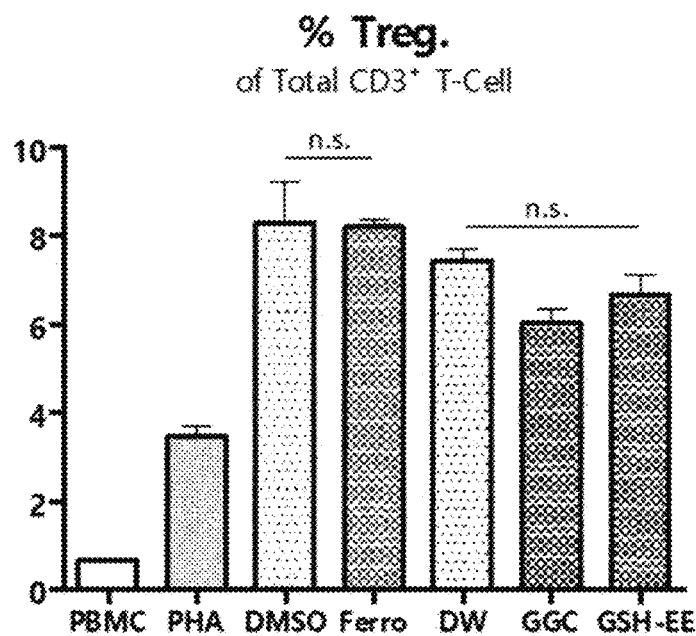
FIG. 28C is a graph showing an effect of promoting the differentiation (n=3) of Treg cells after hUC-MSCs are treated with 1 μM ferrostatin-1 for 24 hours, or treated with 0.2 mM GGC or 2 mM GSH-EE for 2 hours.

In addition, hUC-MSCs were cultured with ferrostatin-1 (0.2, 1, 2 and 4 μM) and liproxstatin-1 (0.1, 0.5, 1 and 2 μM), which control a glutathione level in cells by inhibiting lipid oxidation. As shown in FIG. 27, it can be confirmed that CFU-F was improved. Meanwhile, the hUC-MSCs were treated with 1 μM ferrostatin-1 for 24 hours, 0.2 mM GGC for 2 hours, and 2 mM GSH-EE for 2 hours. As a result, the reduction in T cell proliferation ability and the reduction in T cell differentiation capacity were observed, and promotion of Treg cell differentiation was observed. Materials such as ferrostatin-1 and liproxstatin-1 did not alter an anti-inflammatory effect of the hUC-MSCs as shown in FIGS. 27, and 28A to 28C. This showed that a material for improving a glutathione evaluation parameter can enhance a therapeutic stem cell functions.

Figure 29A:
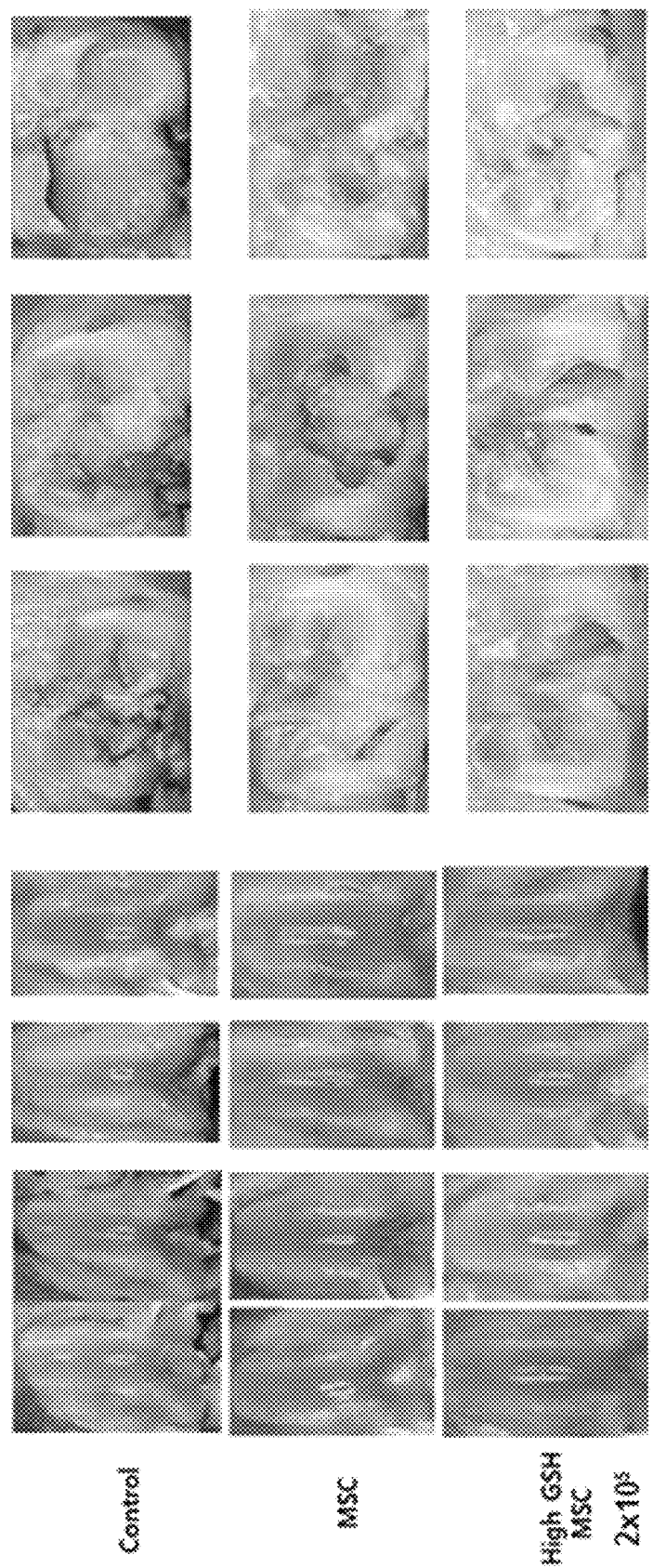
FIG. 29A illustrates images of joint tissues after hES-MSCs ($2\times10^5$) subcultured three times in a culture medium containing AA2G (250 μg/mL) are injected into the joint of a rat, in which osteoarthritis is induced by the rupture of the anterior cruciate ligament (ACL).
Figure 29B:
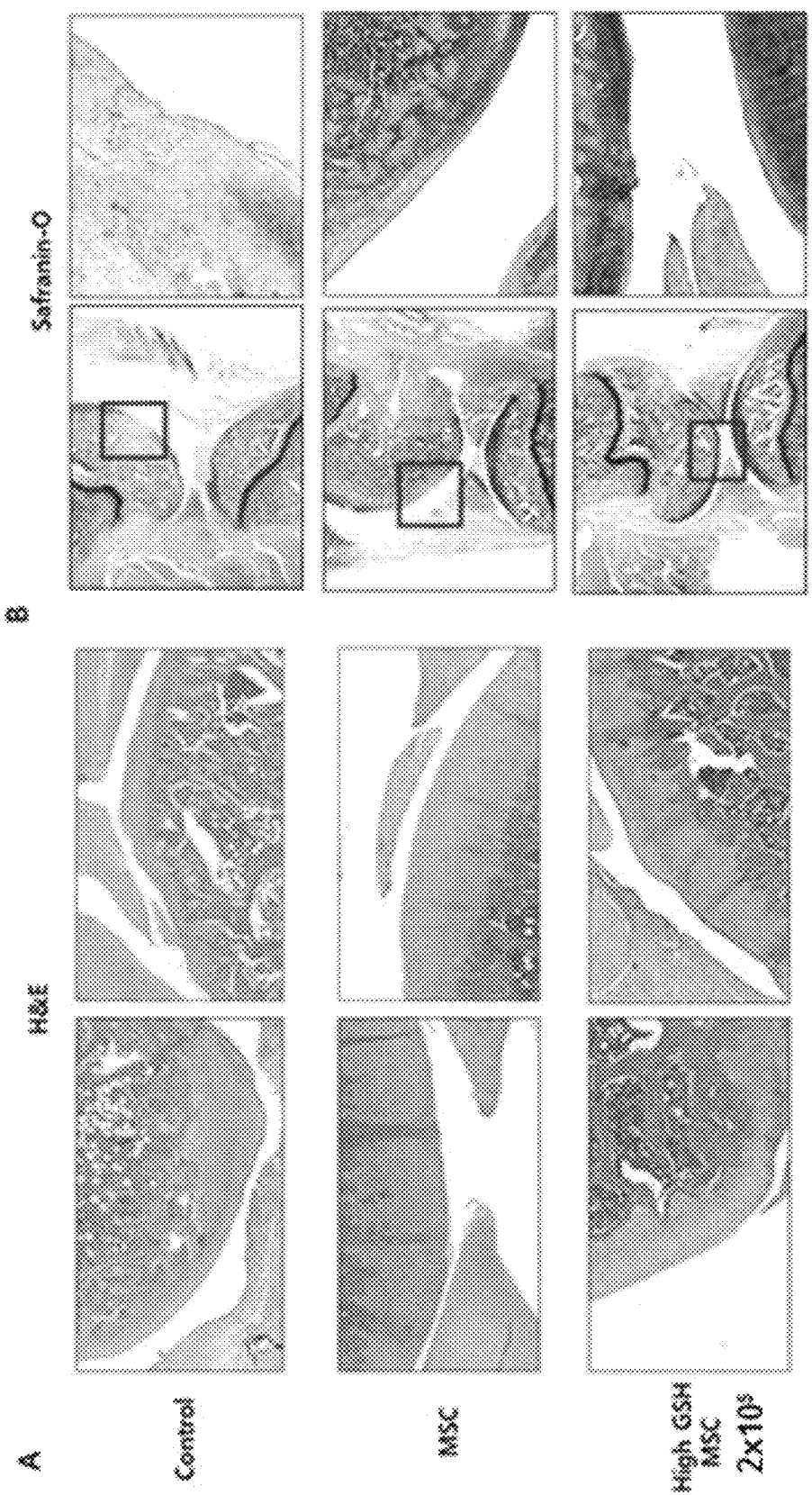
FIG. 29B illustrates images of joint tissues stained with H&E and safranin-O after hES-MSCs ($2\times10^5$) subcultured three times in a culture medium containing AA2G (250 μg/mL) are injected into the joint of a rat, which has an ACL-rupture-induced osteoarthritis.
Figure 29C:
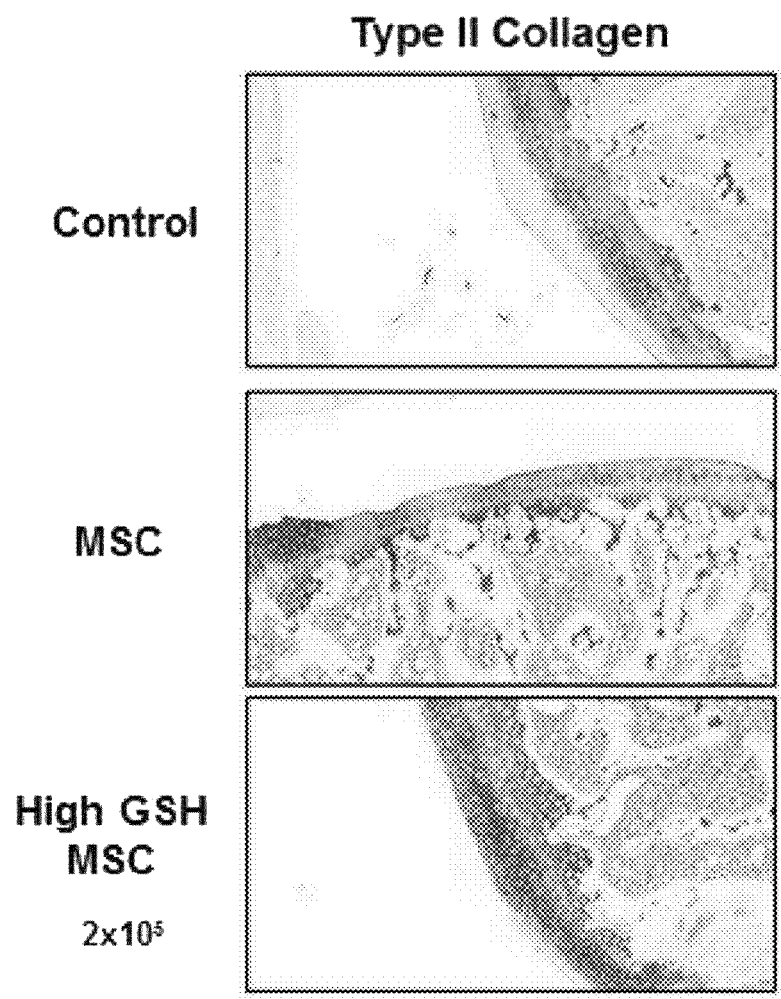
FIG. 29C illustrates images of immuno-stained Type II collagen of joint tissues after hES-MSCs ($2\times10^5$) subcultured three times in a culture medium containing AA2G (250 μg/mL) are injected into the joint of a rat, which has an ACL-rupture-induced osteoarthritis.

In addition, the inventors confirmed a cartilage regeneration effect according to the antioxidation activity of stem cells in an osteoarthritis animal model. An osteoarthritis-induced rat's joint was prepared by rupturing the anterior cruciate ligament (ACL). The hES-MSCs (2×10$^5$) subcultured three times in an AA2G (250 μg/mL)-containing culture medium were injected into the joint. As a result, as shown in FIG. 29A, compared with general stem cells, in transplantation of stem cells with increased antioxidation capacity (high GSH MSC), it can be confirmed that cartilage regeneration efficacy is considerably excellent. In addition, the hES-MSCs (2×10$^5$)-injected joint tissue as described above was prepared, and stained with H&E and safranin-O (FIG. 29B). In addition, the hES-MSCs (2×10$^5$)-injected joint tissue as described above was prepared, and stained with type II collagen (FIG. 29C). It was confirmed that the expression of GAG and Type II collagen was excellent. This showed that a material for improving a glutathione parameter improves the therapeutic efficacy of stem cells.

All data was analyzed using one-way ANOVA or two-way ANOVA with Bonferroni post-hoc tests for non-parametric tests. All analyses were performed with GraphPad Prism 5.0 (GraphPad Software, Canada), and determined to be statistically significant when $p<0.05$ or $p<0.01$.

Example 6: Measurement of GSH Expression Level Using Lipid Oxidizing Agent

After the cultured human umbilical cord-derived mesenchymal stem cells (hUC-MSCs) at passage 4, 7 or 15 were treated with various concentrations of RSL3 and stained with MitoFreSH, the distribution pattern of mitochondrial GSH (mGSH) in the cells was confirmed by histograms using flow cytometry and confocal imaging.

1. Change in mGSH Expression Levels According to RSL3 Concentration and Passage Number 1) Experimental Process <Measurement of GSH Distribution in MSCs Through Flow Cytometry> hUC-MSCs at passage 4, 7 or 15 were prepared, seeded at 70000 cells/well in a 6-well cell culture plate, and cultured at 37° C. for 24 hours. The medium used in the culture was prepared by adding 10% fetal bovine serum and 1× penicillin-streptomycin to α-MEM. After the removal of the medium, a glutathione peroxidase 4 (GPX4) inhibitor, RSL3, was added at a concentration of 0.1/0.5/1 μM, followed by culturing at 37° C. for 1.5 hours. The medium used in the culture was prepared by adding 10% fetal bovine serum and 1× penicillin-streptomycin to α-MEM. After the RSL3-containing medium was removed, 5 μM MitoFreSH-Tracer was added, followed by culturing at 37° C. for 1.5 hours. The medium used in the culture was prepared by adding 10% fetal bovine serum and 1× penicillin-streptomycin to α-MEM. After the MitoFreSH-Tracer-containing medium was removed, the cells were washed with 2 mL of DPBS twice. 250 μL of TrypLE Express was added and reacted at 37° C. for 2.5 minutes, 2% FBS-containing DPBS was added in an equivalent amount to detach the cells from the plate. The cells detached from the plate were transferred to an FACS tube and stored on ice, and a fluorescence level was measured using a flow cytometer.

<Measurement of GSH Distribution Using Fluorescence Imaging> hUC-MSCs at passage 4, 7 or 15 were prepared, seeded at 7000 cells/100 μl per well in a 96-well cell culture plate, and cultured at 37° C. for 24 hours. The medium used in the culture was prepared by adding 10% fetal bovine serum and 1× penicillin-streptomycin to α-MEM. After the removal of the medium, 100 μl of a glutathione peroxidase 4 (GPX4) inhibitor, RSL3, was added at a concentration of 0.1/0.5/1 μM, followed by culturing at 37° C. for 2 hours. The medium used in the culture was prepared by adding 10% fetal bovine serum and 1× penicillin-streptomycin to α-MEM. After the RSL3-containing medium was removed, 15 μM MitoFreSH-Tracer was added per 100 μl, followed by culturing at 37° C. for 1 hour. The medium used in the culture was 10 mM HEPES-containing HBSS. To remove MitoFreSH-Tracer from the medium before measurement, the medium was exchanged with fresh 10 mM HEPES-containing HBSS, and fluorescence images were measured using a confocal imaging system, Operetta.

<Histogram Analysis Method>

A F510/F580 ratio referring to a GSH mean value in cells was calculated by measuring fluorescence values of F510 (fluorescence value when MitoFreSH-Tracer was bound with SH) and F580 (fluorescence value of MitoFreSH-Tracer, which was not bound with SH) in cells and dividing the F510 value by the F580 value. A histogram was expressed with the F510/F580 ratio of the each cells as the X axis and a % amount of cells corresponding to the F510/F580 ratio as the Y axis using the Prism 5 program. Alexa 430/PE (F510/F580) parameters in all samples were analyzed using FlowJo software analyzing flow cytometry, and based on the point where the histogram showing the F510/F580 distribution is divided into two peaks, the cells were divided into $GSH^{High}$ cells (right peak), $GSH^{Low}$ cells (left peak), and then a ratio of corresponding cells was expressed as a percentage (%)

2) Experimental Result

Figure 30:
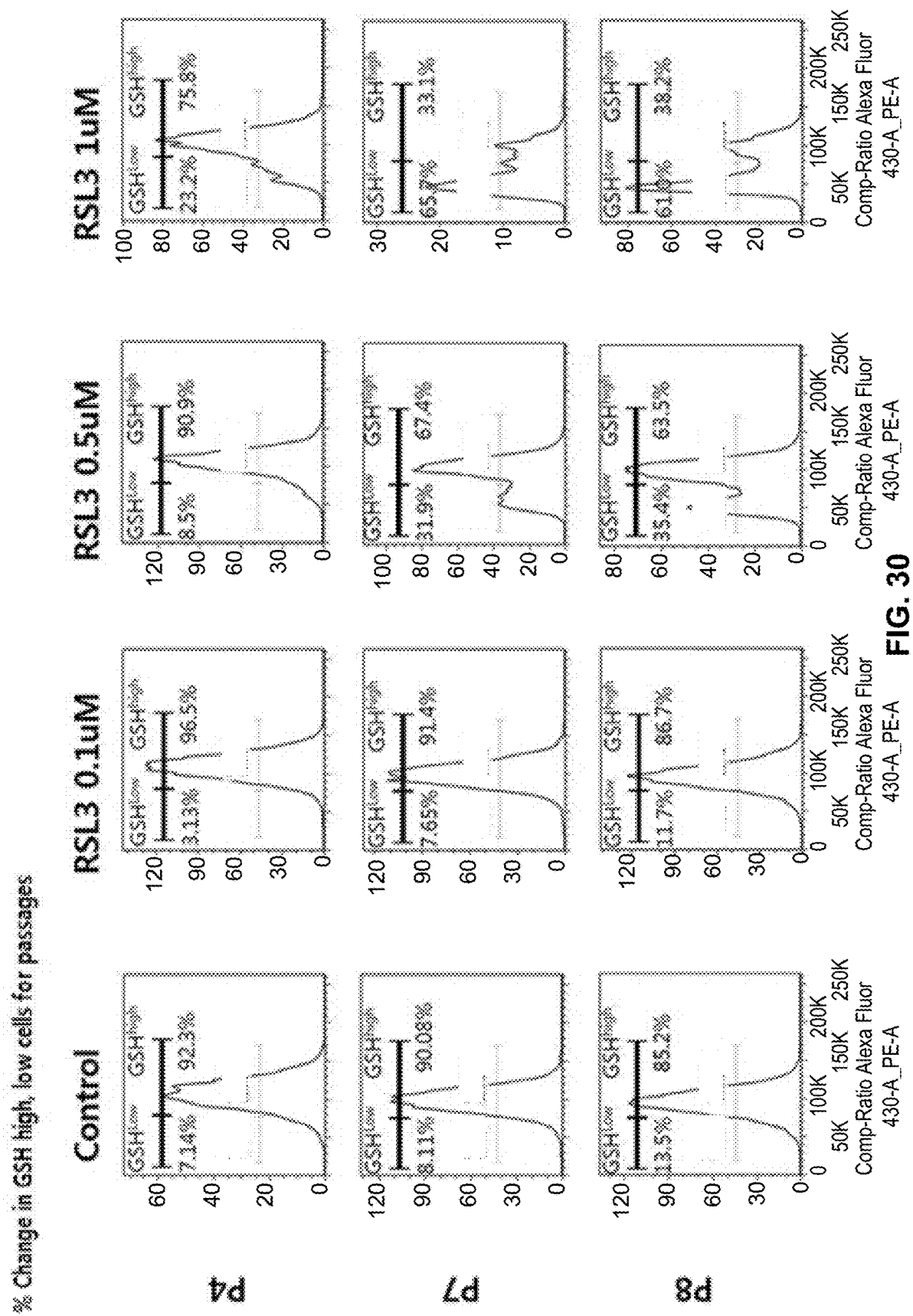
FIG. 30 illustrates histograms obtained by flow cytometry for mGSH expression levels in cells at passage 4, 7 and 15.
Figure 31:
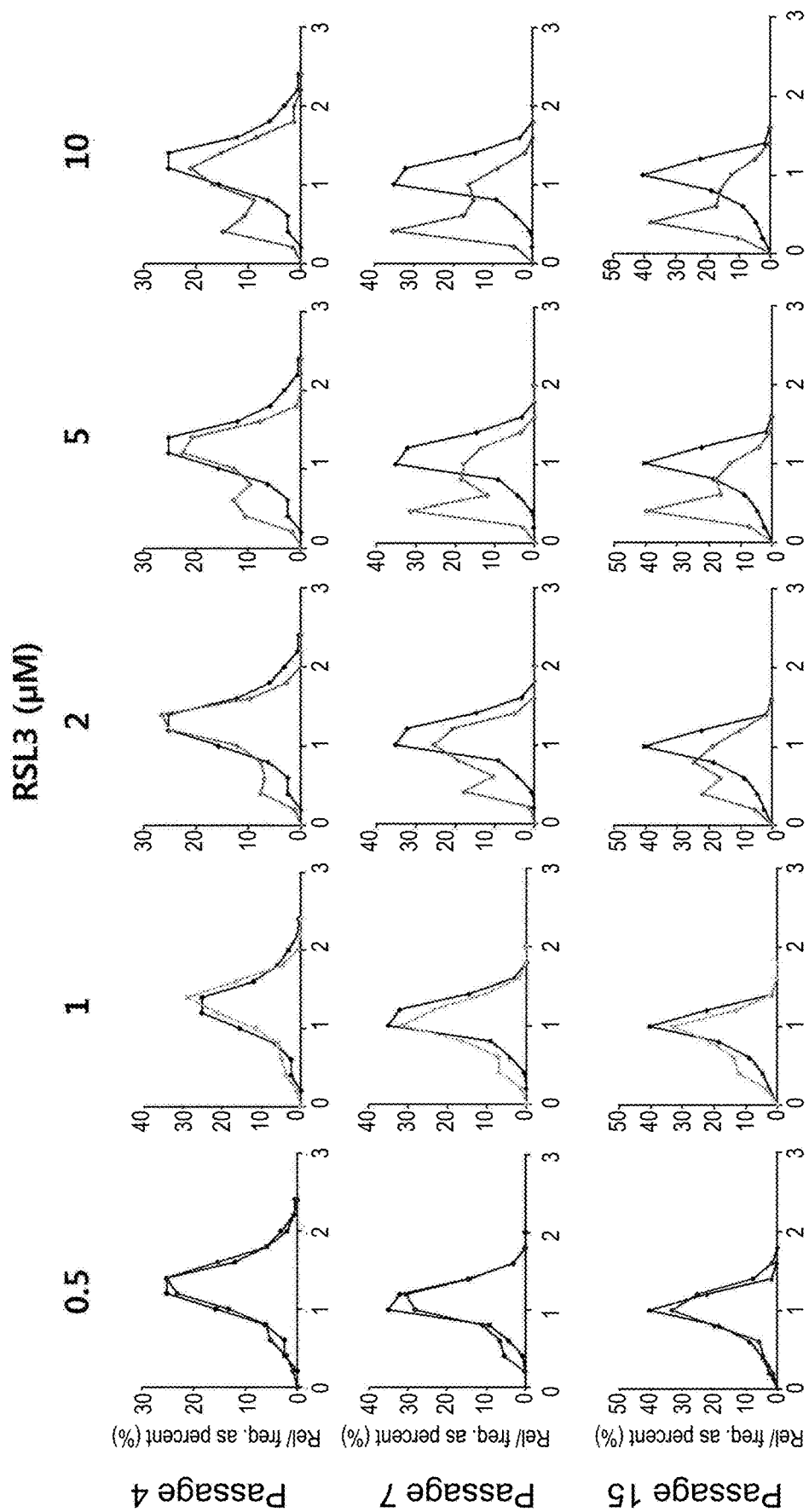
FIG. 31 illustrates histograms obtained by confocal imaging for mGSH expression levels in cells at passage 4, 7 and 15.
Figure 32:
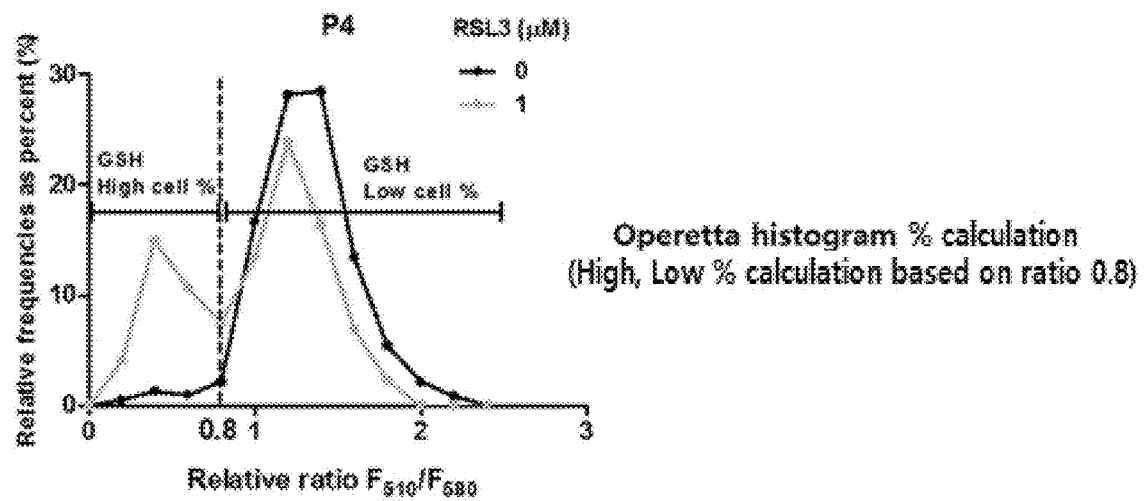
FIG. 32 illustrates distribution patterns of mGSH$^{High}$ cells and mGSH$^{Low}$ cells according to a passages number of stem cells and an RSL3 concentration.
Figure 32:
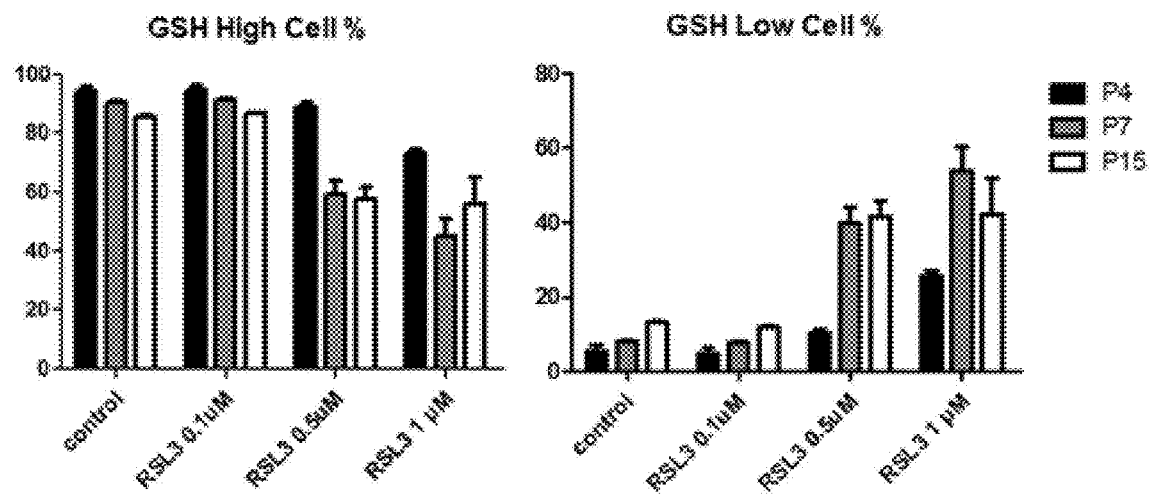
Figure 32:
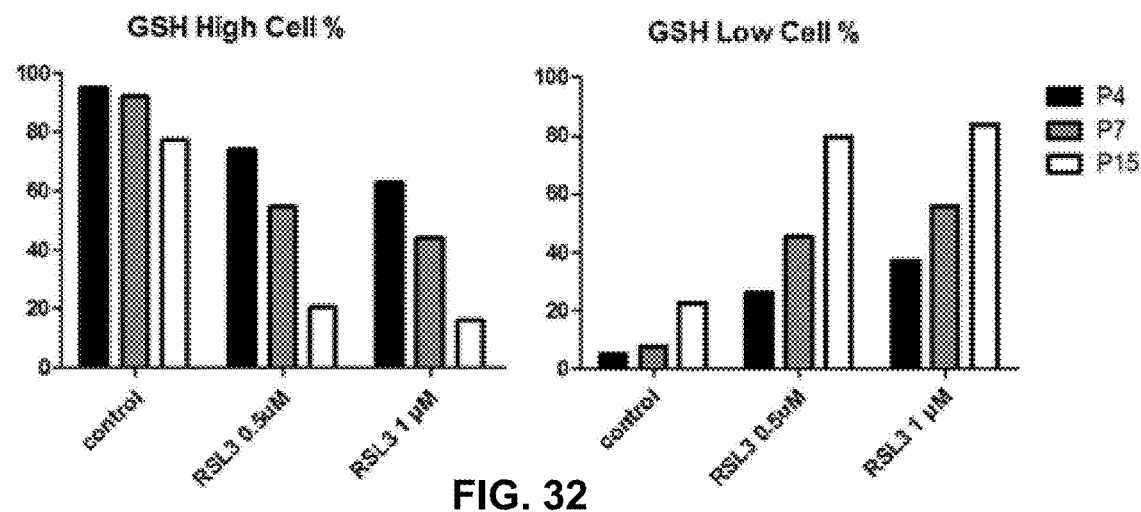

When all of the cultured hUC-MSCs at passage 4, 7 or 15 were not treated with RSL3, although almost the same pattern of mGSH distribution was shown, it can be confirmed that a group in which mGSH levels were reduced depending on an RSL3 concentration and a passage number was observed (FIGS. 30, 31, and 32).

As the passage number increases, the cells are known to undergo antioxidative stress, and many studies have demonstrated that these cells underwent cell senescence, and the functions of stem cells was deteriorated. Based on the studies, it can be estimated that in cells in which antioxidation capacity was deteriorated under a condition of lipid oxidative stress caused by RSL3, compared with cells in which antioxidation capacity was not deteriorated, mGSH levels cannot be normally maintained.

Figure 33:
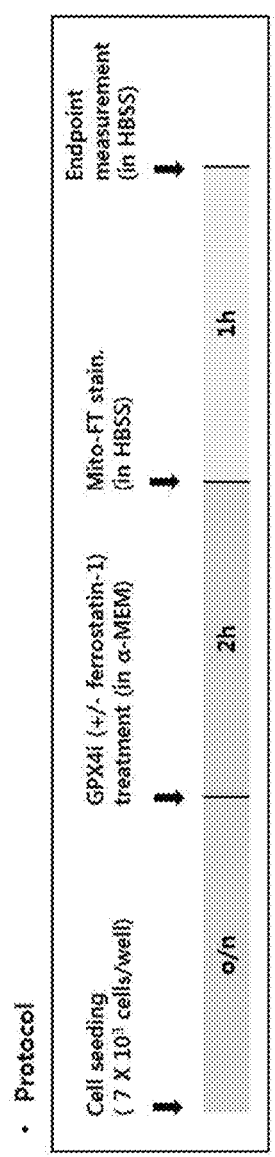
FIG. 33 illustrates the lipid oxide dependency of effect of treatment of MSCs with RSL3, confirmed through ferrostatin-1 treatment.
Figure 33:
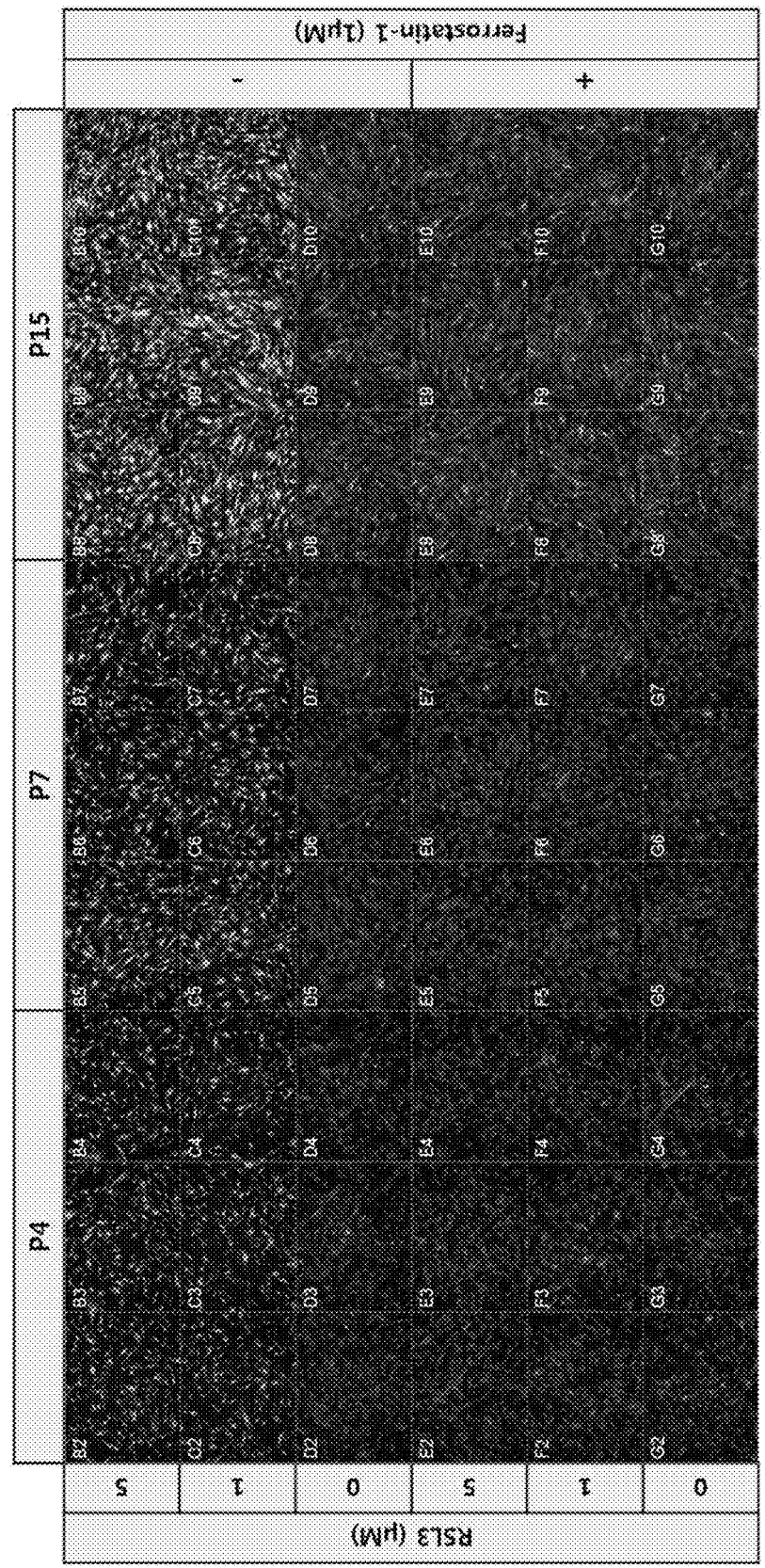

In FIG. 33, green cells as shown in cell fluorescence images are cells that maintain mGSH, and yellow cells are cells that are decreased in mGSH. It can be observed that the higher the passage number, the higher ratio of the yellow cells, and even in the same cells, the yellow cells were observed to be larger and wider than the green cells. In addition, when Ferrostatin-1 was treated, the effect of RSL3 disappeared, and this suggests that the effect is dependent on lipid oxidative stress (FIG. 33).

2. Change in mGSH Expression Level in Human Dermal Fibroblasts

Figure 35:
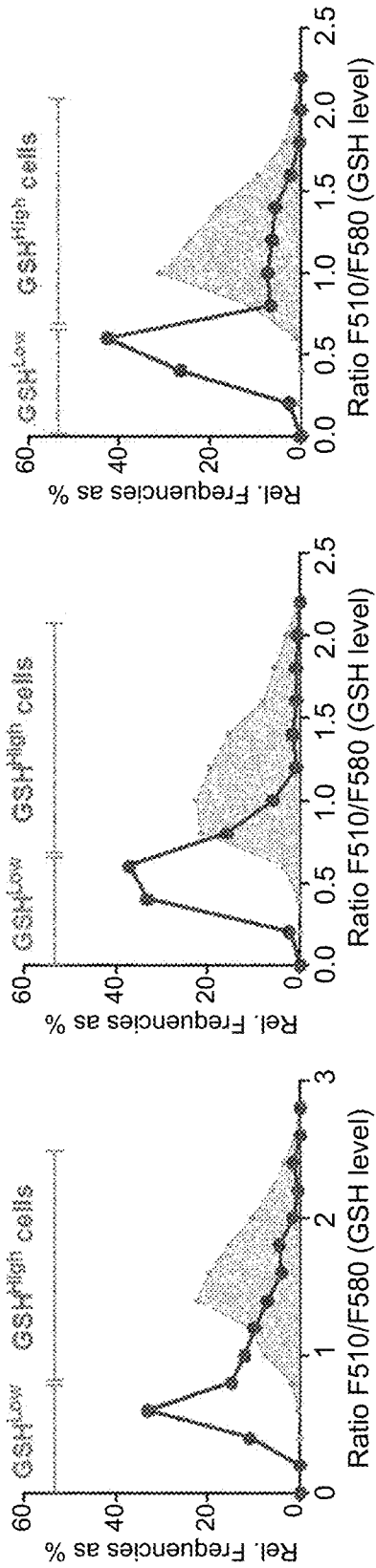
FIG. 35 illustrates distribution patterns of mGSH$^{High}$ and mGSH$^{Low}$ cells according to a passages number for fibroblasts.

As described in the experiment for MSCs, human dermal fibroblasts subcultured several times were treated with RSL3 and the cells were stained with MitoFreSH-Tracer, and a ratio between cells maintaining mGSH and cells not maintaining mGSH was represented as a percentage through confocal imaging. This result, like the result of MSCs, shows that, as the subculture continued, the proportion of cells in which mGSH decreases by treatment with RSL3 increased (FIG. 35).

3. Relationship Between mGSH Expression Level and CD146 Expression Level

1) Experimental Process

To confirm whether the stem cell function of cells in which an mGSH level decreased is deteriorated under lipid oxidative stress caused by RSL3 treatment, an expression level of CD146, which is a cell surface protein known to be highly expressed in stem cells of high quality according to conventional literature, was confirmed through flow cytometry.

The cells were stained by the same method as a method of measuring a mitochondria GSH level through the flow cytometry as described above, and detached from the plate using trypsin. The detached cells were treated with an antibody for flow cytometry with respect to CD146 to which a fluorescent material BUV395 was bound at 4° C. for 30 minutes, and washed with PBS. Using a flow cytometer, F510 and F580 fluorescence values for measuring a GSH level and a BUV395 fluorescence value for measuring CD146 expression were measured. Afterward, based on the point at which the histogram showing the F510/F580 distribution was divided into two peaks, the cells were divided into $GSH^{High}$ cells (right peak) and $GSH^{Low}$ cells (left peak) using FlowJo software, and a CD146-positive ratio of the corresponding cells is represented as a percentage (%).

2) Experimental Result

Figure 34:
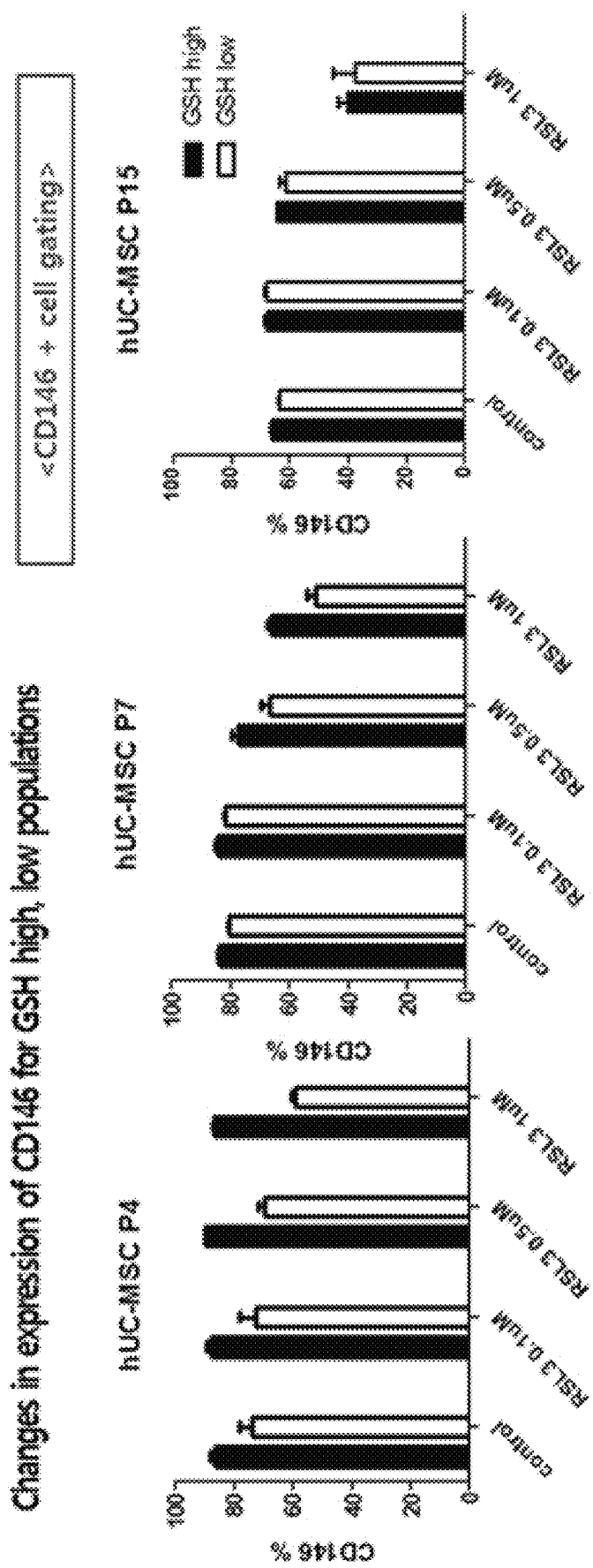
FIG. 34 illustrates a result of comparing CD146 surface expression of mGSH$^{High}$ and mGSH$^{Low}$ cells after RLS3 treatment.

After RSL3 treatment, by staining both MitoFreSH and the CD146 antibody and comparing CD146 surface expression levels in $mGSH^{high}$ and $mGSH^{Low}$ cells, compared with a CD146 mGSH level-maintaining group, it was confirmed that a CD146-positive ratio is lowered by approximately 25% in a P4 hUC-MSC group in which an mGSH level is lowered by RSL3 (FIG. 34). This was similar to a CD146-positive ratio of P15 stem cells. Since P7 has no difference in CD146-positive ratio from P4, the quality of two types of cells could not be distinguished by a such method of evaluating the quality of cells using the ratio of the expression of the surface protein, but the quality thereof could also be seperately evaluated by cell type using the method of the present invention as described in FIG. 32.

Hereinabove, specific parts of the present invention have been described in detail. However, it will be apparent to those of ordinary skill in the art that such detailed descriptions are just exemplary embodiments, and thus it is obvious that the scope of the present invention is not limited thereto. Therefore, the actual range of the present invention will be defined by the accompanying claims and equivalents thereof.

REFERENCES

1. E. ROBBINS et al., J Exp Med. 1970 Jun. 1; 131(6): 1211-22.
2. Georgakopoulou E A et al., Aging (Albany NY), 2013 January; 5(1):37-50.
3. Thomas Kuilman et al., Genes Dev. 2010 Nov. 15; 24(22):2463-79.
4. Jean-Philippe Copp' et al., Annu Rev Pathol. 2010; 5:99-118.

INDUSTRIAL APPLICABILITY

According to the present invention, by using FreSH-Tracer and evaluation parameters according to the present invention in real-time monitoring of an intracellular GSH level in living stem cells and differentiation of cells according to a GSH level, the quality of a cell therapeutic agent may be evaluated, and its quality may be improved.

The invention claimed is:

1. A method of improving the quality of cells, comprising:
isolating desired cells;
measuring a glutathione (GSH) level in the isolated cells;
determining cell quality according to the GSH level,
  wherein the determination of cell quality according to the GSH level is performed based on one or more GSH evaluation parameters selected from the group consisting of:
    i) glutathione regeneration capacity (GRC) of the isolated cells, wherein GRC is a value obtained by real-time monitoring of FR or F510 after the isolated cells are treated with an oxidizing agent, and is calculated by dividing a value obtained by subtracting a second area under the curve (AUC) of a group of the isolated cells treated with a second oxidizing agent from a first AUC of a group of the isolated cells treated with a first oxidizing agent by a value obtained by subtracting the second AUC of the group of the isolated cells treated with the second oxidizing agent from a third AUC of a naive control and multiplying the resulting value by 100, wherein FR is an fluorescence emission ratio of a fluorescence emission value at 510 nm (F510) to a fluorescence emission value at 580 nm (F580); and
    ii) oxidative stress resistance capacity (ORC) of the isolated cells, wherein ORC is a value of cell counts with a variation in GSH expression, obtained by comparing a GSH level quantified after the isolated cells are treated with a first oxidizing agent with a GSH level quantified in control cells which are not treated with an oxidizing agent or in control cells which have not yet been treated with an oxidizing agent; and
adding a material capable of improving the one or more GSH evaluation parameters into the isolated cells, wherein the material is any one or more selected from the group consisting of glutathione ethyl ester, ascorbic acid 2-glucoside, glutathione, N-acetylcysteine, 2-mercaptoethanol, dithiothreitol (DTT), cysteine, γ-glutamyl cysteine (GGC), GGC esters, oxo-4-thiazolidinecarboxylic acid (OTC), L-2-oxo-4-thiazolidinecarboxylic acid, lipoic acid, Ferrostatin-1, Liproxstatin-1, vitamin D3, 1-alpha, 25-dihydroxy VitD3, vitamin E, coenzyme Q10, and an iron or copper ion chelator selected from the group consisting of deferoxamine, deferiprone and deferasirox, baicalin, baicalein, luteolin, quercetin, butein, flower extracts of *Chrysanthemum morifolium* Ramat, leaf extracts of *Cedela sinensis* A. Juss, extracts of *Oenothera stricta* Ledeb., extracts of *Equisetum arvense* L., leaf extracts of *Ipomoea batatas*, tomato extracts, and homocysteine.

2. The method according to claim 1, wherein the improvement of cell quality is achieved by raising GRC or reducing, in an ORC measurement, a ratio of the isolated cells which have been treated with an oxidizing agent and thus exhibit decreased GSH as compared with cells not treated with an oxidizing agent.

3. The method according to claim 1, further comprising:
measuring a GSH level before the addition of the material capable of improving the one or more GSH evaluation parameters.

4. The method according to claim 3, further comprising:
checking, by measuring a GSH level, whether a GSH level has been improved after the addition of the material capable of improving the one or more GSH evaluation parameters.

5. The method according to claim 1, wherein the desired cells are:
any one type of stem cells selected from the group consisting of adult stem cells, embryonic stem cells and induced pluripotent stem cells;
any one type of immune cells selected from the group consisting of dendritic cells, natural killer cells, T cells, B cells, regulatory T cells (Treg cells), natural killer T cells, innate lymphoid cells, macrophages, granulocytes, chimeric antigen receptor-T (CAR-T) cells, lymphokine-activated killer (LAK) cells and cytokine induced killer (CIK) cells;
any one type of somatic cells selected from the group consisting of fibroblasts, chondrocytes, synovial cells, keratinocytes, adipocytes, osteoblasts, osteoclasts and peripheral blood mononuclear cells;
any one type of cell line used in production of a protein agent and selected from the group consisting of CHO cells, NS0 cells, Sp2/0 cells, BHK cells, C127 cells, HEK293 cells, HT-1080 cells, and PER.C6 cells; or
any one type of a human microbiome selected from the group consisting of microorganisms originating from the mouth, nasal cavity, lung, skin, gastric intestinal tract and urinary tract of a human or animal.

6. The method according to claim 5, wherein the T cells are not regulatory T cells (Treg cells).

7. The method according to claim 1, wherein the first oxidizing agent is selected from the group consisting of:
hydroperoxides; thiol oxidizing agents; glutathione reductase inhibitors; thioredoxin inhibitors; mitochondrial electron transport chain inhibitors; NADPH oxidase activators; gpx4 inhibitors; system $x^-_c$ inhibitors; inducers for reducing GPX4 protein and CoQ10 levels; lipid peroxidation inducers; glutamate-cysteine ligase (GCL) inhibitors; GSH reduction inducers; DPI2, cisplatin, cysteinase, statin, iron ammonium citrate, trigonelline, carbon tetrachloride, silica-based nanoparticles, and specific heat plasma.

8. The method according to claim 1, wherein the first oxidizing agent is selected from the group consisting of:
$H_2O_2$, tert-butyl peroxide, diamide, GSSG (oxidized GSH), 5,5'-dithiobis(2-nitrobenzoic acid), maleimide, N-ethyl maleimide, 4-maleimidobutyric acid, 3-maleimidopropionic acid, iodoacetamide, bis-chloroethylnitrozourea; PX-12, antimycin A, rotenone, oligomycin, carbonyl cyanide m-chlorophenyl hydrazine, phorbol 12-myristate 13-acetate, 1S,3R-RAS-selective lethal 3 (1S,3R-RSL3), DPI19, DPI18, DPI17, DPI13, DPI12, DPI10 (ML210), DPI7 (ML162), altretamine; erastin, sulfasalazine, sorafenib, glutamate, piperazine erastin, imidazole ketone erastin, an erastin analog, ferroptosis inducer 56 (FIN56), caspase-independent lethal 56 (CIL56) and endoperoxide ($FINO_2$), buthionine-(S,R)-sulfoximine, diethyl maleate, DPI2, cisplatin, cysteinase, statin, iron ammonium citrate, trigonelline, carbon tetrachloride, silica-based nanoparticles and specific heat plasma.

9. The method according to claim 1, wherein the second oxidizing agent includes maleimide, 4-maleimidobutyric acid, 3-maleimidopropionic acid, ethylmaleimide, N-ethylmaleimide, iodoacetamide, 5,5'-dithiobis(2-nitrobenzoic acid), or iodoacetamidopropionic acid.

* * * * *

SEQUENCE LISTING

<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 1
tgtgactgcc caagatgaag acc                                               23

<210> SEQ ID NO 2
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 2
ttgggtatct caggcatctc cttc                                              24

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
gaactgaaag ctctccacct ccag                                              24

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 4
aaaggacatg gagaacacca cttg                                              24

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 5
agcacctgct tgtttggaag gg                                                22

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
acacaacagg aagctggata cgg                                               23

<210> SEQ ID NO 7
<211> LENGTH: 23
<212> TYPE: DNA
<213> ORGANISM: Artificial Sequence

```
<220> FEATURE:
<223> OTHER INFORMATION: Synthetic oligonucleotide

<400> SEQUENCE: 7
ggcagaccag catgacagat ttc                                              23

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 8
agatgtagag cgggcctttg ag                                               22
```